(12) United States Patent  
Simmons et al.

(10) Patent No.: US 9,291,591 B2
(45) Date of Patent: Mar. 22, 2016

(54) UNIVERSAL TEST STRIP PORT

(71) Applicant: Abbott Diabetes Care Inc., Alameda, CA (US)

(72) Inventors: Matthew Simmons, Pleasanton, CA (US); John R. Galasso, St. Helena, CA (US); Gary Ashley Stafford, Hayward, CA (US); Cherie Bulala, Berkeley, CA (US); Christopher Myles, Alameda, CA (US); Philip Justus Wunderle, III, El Cerrito, CA (US); Bonita Song, Oakland, CA (US); Richard G. Ries, Livermore, CA (US); Morvarid G. Shafie, Concord, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 0 days.

(21) Appl. No.: 14/481,594

(22) Filed: Sep. 9, 2014

(65) Prior Publication Data

US 2014/0374277 A1 Dec. 25, 2014

Related U.S. Application Data

(63) Continuation of application No. 12/695,947, filed on Jan. 28, 2010, now Pat. No. 8,828,330.

(51) Int. Cl.
| | |
|---|---|
| *G01N 31/22* | (2006.01) |
| *G01N 27/327* | (2006.01) |
| *A61B 5/145* | (2006.01) |
| *G01N 33/487* | (2006.01) |
| *A61B 5/1473* | (2006.01) |
| *A61M 5/172* | (2006.01) |

(52) U.S. Cl.
CPC ............ *G01N 27/327* (2013.01); *A61B 5/1473* (2013.01); *A61B 5/14532* (2013.01); *A61M 5/1723* (2013.01); *G01N 33/48785* (2013.01); *A61B 2560/045* (2013.01); *A61B 2562/0295* (2013.01)

(58) Field of Classification Search
CPC .......................... G01N 33/50; A61B 2560/045
See application file for complete search history.

(56) References Cited

U.S. PATENT DOCUMENTS

| | | | |
|---|---|---|---|
| 4,545,382 A | 10/1985 | Higgins et al. | |
| 4,711,245 A | 12/1987 | Higgins et al. | |
| 5,262,035 A | 11/1993 | Gregg et al. | |
| 5,262,305 A | 11/1993 | Heller et al. | |
| 5,264,014 A | 11/1993 | Lannefors et al. | |
| 5,320,715 A | 6/1994 | Berg | |
| 5,356,786 A | 10/1994 | Heller et al. | |
| 5,509,410 A | 4/1996 | Hill et al. | |

(Continued)

FOREIGN PATENT DOCUMENTS

| | | |
|---|---|---|
| JP | 2003114213 | 4/2003 |
| JP | 2003217741 | 7/2003 |

(Continued)

*Primary Examiner* — Jyoti Nagpaul
(74) *Attorney, Agent, or Firm* — Edward J. Baba; Shweta Chandra; Bozicevic, Field & Francis LLP

(57) ABSTRACT

The present disclosure provides a sensor port configured to receive a plurality of analyte sensors having different sizes, shapes and/or electrode configurations. Also provided are analyte meters, analyte monitoring devices and/or systems and drug delivery devices and/or systems utilizing the disclosed sensor ports.

26 Claims, 24 Drawing Sheets

(56) References Cited

U.S. PATENT DOCUMENTS

| | | | |
|---|---|---|---|
| 5,536,249 A | 7/1996 | Castellano et al. | |
| 5,593,852 A | 1/1997 | Heller et al. | |
| 5,601,435 A | 2/1997 | Quy | |
| 5,628,890 A | 5/1997 | Carter et al. | |
| 5,820,551 A | 10/1998 | Hill et al. | |
| 5,822,715 A | 10/1998 | Worthington et al. | |
| 5,899,855 A | 5/1999 | Brown | |
| 5,918,603 A | 7/1999 | Brown | |
| 5,925,021 A | 7/1999 | Castellano et al. | |
| 6,071,391 A | 6/2000 | Gotoh et al. | |
| 6,120,676 A | 9/2000 | Heller et al. | |
| 6,121,009 A | 9/2000 | Heller et al. | |
| 6,143,164 A | 11/2000 | Heller et al. | |
| 6,144,837 A | 11/2000 | Quy | |
| 6,161,095 A | 12/2000 | Brown | |
| 6,175,752 B1 | 1/2001 | Say et al. | |
| 6,270,455 B1 | 8/2001 | Brown | |
| 6,281,006 B1 | 8/2001 | Heller et al. | |
| 6,284,478 B1 | 9/2001 | Heller et al. | |
| 6,299,757 B1 | 10/2001 | Feldman et al. | |
| 6,338,790 B1 | 1/2002 | Feldman et al. | |
| 6,377,894 B1 | 4/2002 | Deweese et al. | |
| 6,461,496 B1 | 10/2002 | Feldman et al. | |
| 6,503,381 B1 | 1/2003 | Gotoh et al. | |
| 6,514,460 B1 | 2/2003 | Fendrock | |
| 6,514,718 B2 | 2/2003 | Heller et al. | |
| 6,526,298 B1 | 2/2003 | Khalil et al. | |
| 6,540,891 B1 | 4/2003 | Stewart et al. | |
| 6,560,471 B1 | 5/2003 | Heller et al. | |
| 6,591,125 B1 | 7/2003 | Buse et al. | |
| 6,592,745 B1 | 7/2003 | Feldman et al. | |
| 6,600,997 B2 | 7/2003 | Deweese et al. | |
| 6,616,819 B1 * | 9/2003 | Liamos et al. | 204/403.02 |
| 6,618,934 B1 | 9/2003 | Feldman et al. | |
| 6,676,816 B2 | 1/2004 | Mao et al. | |
| 6,730,200 B1 | 5/2004 | Stewart et al. | |
| 6,736,957 B1 | 5/2004 | Forrow et al. | |
| 6,746,582 B2 | 6/2004 | Heller et al. | |
| 6,749,740 B2 | 6/2004 | Liamos et al. | |
| 6,764,581 B1 | 7/2004 | Forrow et al. | |
| 6,773,671 B1 | 8/2004 | Lewis et al. | |
| 6,881,551 B2 | 4/2005 | Heller et al. | |
| 6,893,545 B2 | 5/2005 | Gotoh et al. | |
| 6,942,518 B2 | 9/2005 | Liamos et al. | |
| 7,041,468 B2 | 5/2006 | Drucker et al. | |
| 7,167,818 B2 | 1/2007 | Brown | |
| 7,214,542 B2 | 5/2007 | Hutchinson | |
| 7,299,082 B2 | 11/2007 | Feldman et al. | |
| 8,226,891 B2 * | 7/2012 | Sloan et al. | 422/82.02 |
| 2004/0186365 A1 | 9/2004 | Jin et al. | |
| 2004/0254434 A1 | 12/2004 | Goodnow et al. | |
| 2005/0009126 A1 | 1/2005 | Andrews et al. | |
| 2005/0256382 A1 | 11/2005 | Eisenmann et al. | |
| 2005/0258050 A1 | 11/2005 | Harding | |
| 2006/0025662 A1 | 2/2006 | Buse et al. | |
| 2006/0091006 A1 | 5/2006 | Wang et al. | |
| 2006/0224141 A1 | 10/2006 | Rush et al. | |
| 2007/0015286 A1 | 1/2007 | Neel et al. | |
| 2007/0068807 A1 | 3/2007 | Feldman et al. | |
| 2007/0095661 A1 | 5/2007 | Wang et al. | |
| 2007/0108048 A1 | 5/2007 | Wang et al. | |
| 2007/0123782 A1 | 5/2007 | Connolly et al. | |
| 2007/0153355 A1 | 7/2007 | Huang et al. | |
| 2007/0199818 A1 | 8/2007 | Petyt et al. | |
| 2008/0066305 A1 | 3/2008 | Wang et al. | |
| 2008/0099332 A1 | 5/2008 | Scott et al. | |
| 2008/0102441 A1 | 5/2008 | Chen et al. | |
| 2008/0114280 A1 | 5/2008 | Stafford et al. | |
| 2008/0119702 A1 | 5/2008 | Reggiardo et al. | |
| 2008/0119709 A1 | 5/2008 | Wang et al. | |
| 2008/0119710 A1 | 5/2008 | Reggiardo et al. | |
| 2008/0148873 A1 | 6/2008 | Wang et al. | |
| 2008/0234559 A1 | 9/2008 | Arbogast et al. | |
| 2008/0267823 A1 | 10/2008 | Wang et al. | |
| 2008/0319296 A1 | 12/2008 | Bernstein et al. | |
| 2009/0054749 A1 | 2/2009 | He et al. | |
| 2009/0095625 A1 | 4/2009 | Forrow | |
| 2009/0105570 A1 | 4/2009 | Sloan et al. | |
| 2009/0128325 A1 | 5/2009 | Ivanov et al. | |
| 2009/0177142 A1 | 7/2009 | Bloomquist et al. | |
| 2009/0214384 A1 | 8/2009 | Wang et al. | |
| 2009/0255811 A1 | 10/2009 | Forrow et al. | |
| 2009/0294277 A1 | 12/2009 | Thomas et al. | |
| 2010/0064800 A1 | 3/2010 | Stafford et al. | |
| 2010/0152561 A1 | 6/2010 | Goodnow et al. | |
| 2010/0198034 A1 | 8/2010 | Thomas et al. | |
| 2010/0213057 A1 | 8/2010 | Feldman et al. | |
| 2010/0324392 A1 | 12/2010 | Yee et al. | |
| 2010/0325868 A1 | 12/2010 | Wang et al. | |
| 2010/0326842 A1 | 12/2010 | Mazza et al. | |
| 2011/0040246 A1 | 2/2011 | Galasso | |

FOREIGN PATENT DOCUMENTS

| | | |
|---|---|---|
| JP | 2004063197 | 2/2004 |
| JP | 2004101514 | 4/2004 |
| JP | 2007134076 | 5/2007 |
| JP | 2009178367 | 8/2009 |
| JP | 2009544039 | 12/2009 |
| JP | 2009544065 | 12/2009 |

* cited by examiner

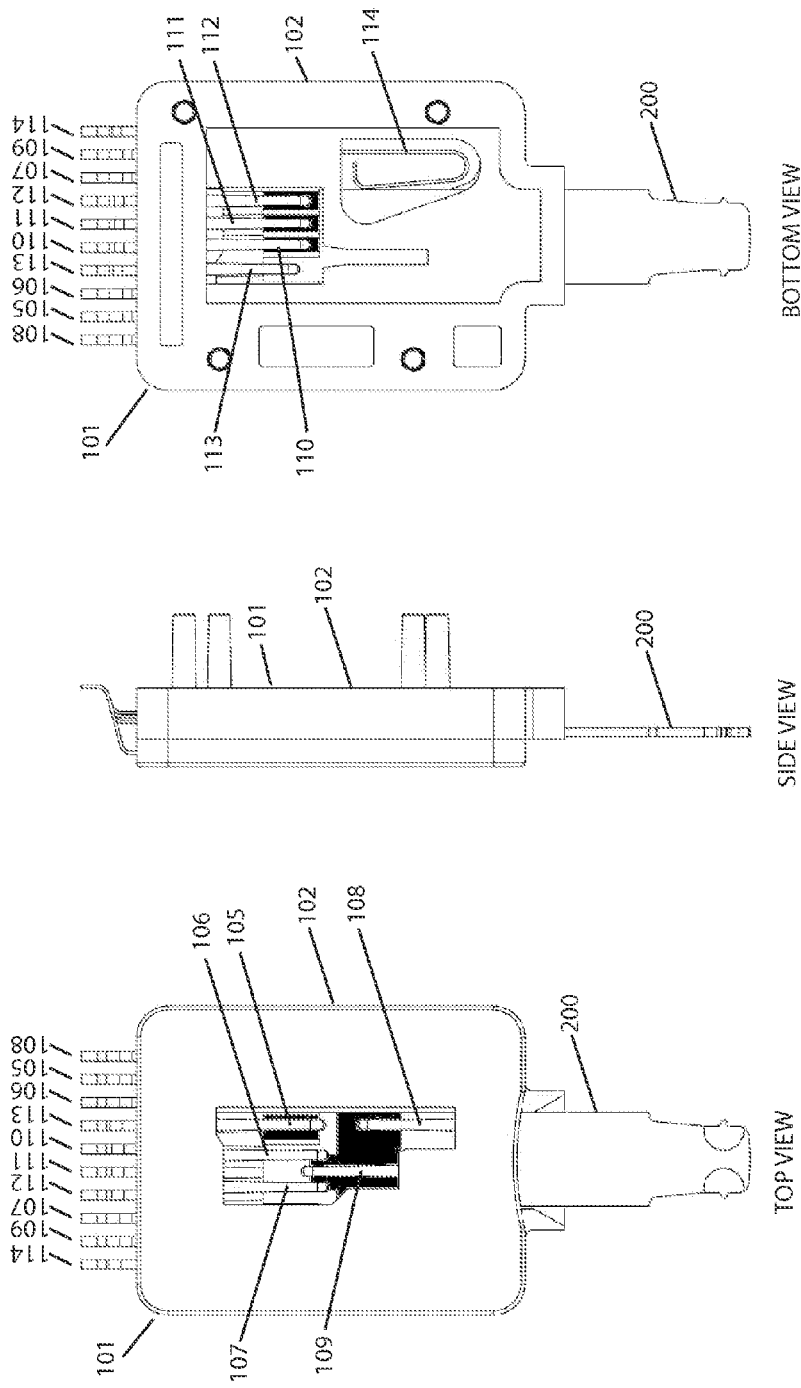

SECTION A-A

DETAIL B

DETAIL U

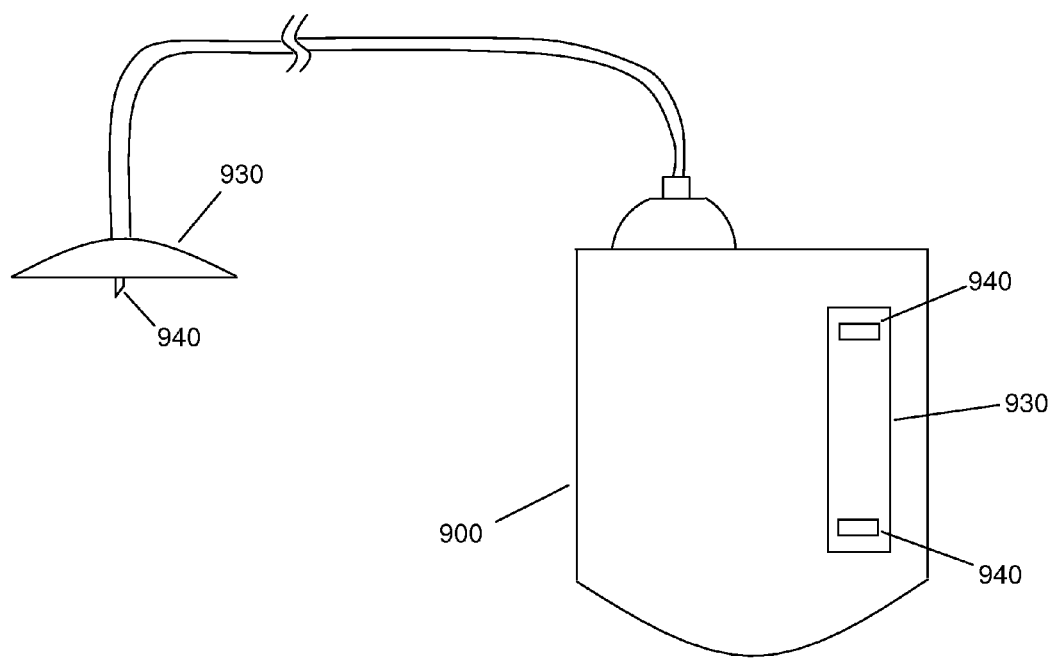
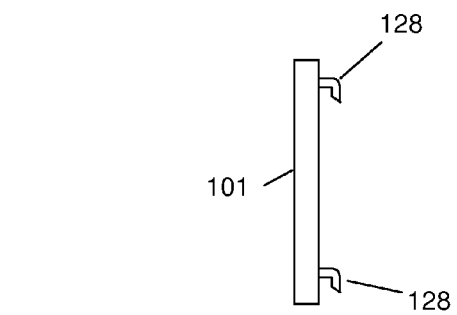
FIG. 21B

UNIVERSAL TEST STRIP PORT

CROSS-REFERENCE TO RELATED APPLICATIONS

This application is a continuation of U.S. patent application Ser. No. 12/695,947, filed on Jan. 28, 2010, the disclosure of which is herein incorporated by reference.

BACKGROUND

Analytical sensors and meters are often used in chemistry and medicine to determine the presence and/or concentration of a biological analyte of interest. For example, such analytical sensors and meters are used to monitor glucose and/or ketone levels in diabetic patients.

Many currently available analyte meters are configured such that a sensor is inserted into a sensor port of the analyte meter during the testing process. As a variety of sensor configurations are currently available, it would be desirable and useful to develop a sensor port and meter capable of receiving analyte sensors having a variety of configurations.

SUMMARY OF THE INVENTION

The present disclosure provides a sensor port configured to receive a plurality of analyte sensors having different sizes, shapes and/or electrode configurations. Also provided are analyte meters, analyte monitoring devices and/or systems and drug delivery devices and/or systems utilizing the disclosed sensor ports. These and other objects, features and advantages of the present disclosure will become more fully apparent from the following detailed description of the embodiments, the appended claims and the accompanying drawings.

In a first aspect of the present disclosure, a sensor port is provided which includes a sensor port housing and a plurality of sensor port contacts positioned in the sensor port housing, wherein the sensor port is configured to receive a first analyte sensor having an opposing electrode configuration and a second analyte sensor having a co-planar electrode configuration.

In one embodiment of the first aspect, the first analyte sensor is a glucose sensor and the second analyte sensor is a ketone sensor.

In another embodiment of the first aspect, both the first and second analyte sensors are glucose sensors.

In another embodiment of the first aspect, the sensor port includes a communication unit.

In another embodiment of the first aspect, the sensor port includes a communication unit, and the communication unit is configured to provide two-way communication between the sensor port and a device and/or network external to the sensor port.

In another embodiment of the first aspect, the sensor port includes a communication unit, and the communication unit is configured to provide two-way communication between the sensor port and a network external to the sensor port.

In another embodiment of the first aspect, the sensor port includes a communication unit, the communication unit is configured to provide two-way communication between the sensor port and a network external to the sensor port, and the network is a computer network.

In another embodiment of the first aspect, the sensor port includes a communication unit, and the communication unit includes a Universal Serial Bus (USB) connector.

In another embodiment of the first aspect, the sensor port includes a communication unit, and the communication unit is configured to provide wireless communication between the sensor port and an external device and/or network.

In another embodiment of the first aspect, the sensor port includes a communication unit, the communication unit is configured to provide wireless communication between the sensor port and an external device and/or network, and the communication unit utilizes a wireless communication protocol selected from a radio frequency (RF) protocol and an infrared (IR) protocol.

In another embodiment of the first aspect, the sensor port includes a communication unit, the communication unit is configured to provide wireless communication between the sensor port and an external device, the external device includes a Radio-Frequency Identification (RFID) tag, and the communication unit utilizes an RF wireless communication protocol to communicate with the Radio-Frequency Identification (RFID) tag.

In another embodiment of the first aspect, the sensor port includes a communication unit, the communication unit is configured to provide wireless communication between the sensor port and an external device and/or network, and the communication unit utilizes a wireless communication protocol selected from ZigBee®, WiFi®, Bluetooth®, code division multiple access (CDMA) and Global System for Mobile communications (GSM).

In another embodiment of the first aspect, the sensor port includes a communication unit, and the communication unit is configured to provide wireless communication between the sensor port and an external device.

In another embodiment of the first aspect, the sensor port includes a communication unit, the communication unit is configured to provide wireless communication between the sensor port and an external device, and the external device is a medication delivery device or an implanted or partially implanted analyte sensor.

In another embodiment of the first aspect, the sensor port includes a communication unit, the communication unit is configured to provide wireless communication between the sensor port and an external device, and the external device is an insulin pump.

In another embodiment of the first aspect, the sensor port is configured to receive analyte sensors having different widths.

In another embodiment of the first aspect, the sensor port is configured to receive analyte sensors having different widths, and the sensor port includes a side wall and a biasing mechanism configured to position the analyte sensors against the sidewall during insertion of the analyte sensors.

In another embodiment of the first aspect, the sensor port is configured to receive analyte sensors having different widths, and the first analyte sensor has a width which is greater than that of the second analyte sensor.

In another embodiment of the first aspect, the sensor port is configured to receive analyte sensors having different widths, and the first analyte sensor has a width which is less than that of the second analyte sensor.

In another embodiment of the first aspect, the sensor port includes an analyte sensor ejector slidably engaged therewith.

In another embodiment of the first aspect, the sensor port includes at least four sensor port contacts configured to contact the first analyte sensor upon insertion of the first analyte sensor into the sensor port and at least three sensor port contacts configured to contact the second analyte sensor upon insertion of the second analyte sensor into the sensor port.

In another embodiment of the first aspect, the sensor port includes at least seven different sensor port contacts, including at least four sensor port contacts configured to contact the first analyte sensor upon insertion of the first analyte sensor into the sensor port and at least three sensor port contacts configured to contact the second analyte sensor upon insertion of the second analyte sensor into the sensor port.

In another embodiment of the first aspect, the sensor port includes at least nine different sensor port contacts, including at least four sensor port contacts configured to contact the first analyte sensor upon insertion of the first analyte sensor into the sensor port and at least three sensor port contacts configured to contact the second analyte sensor upon insertion of the second analyte sensor into the sensor port.

In another embodiment of the first aspect, the sensor port includes at least four sensor port contacts configured to contact the first analyte sensor upon insertion of the first analyte sensor into the sensor port, at least three sensor port contacts configured to contact the second analyte sensor upon insertion of the second analyte sensor into the sensor port, a top portion and a bottom portion engaged with the top portion.

In another embodiment of the first aspect, the sensor port includes at least four sensor port contacts configured to contact the first analyte sensor upon insertion of the first analyte sensor into the sensor port, at least three sensor port contacts configured to contact the second analyte sensor upon insertion of the second analyte sensor into the sensor port, a top portion and a bottom portion engaged with the top portion, wherein one of the at least four sensor port contacts is attached to the top portion of the sensor port and three of the at least four sensor port contacts are attached to the bottom portion of the sensor port.

In another embodiment of the first aspect, the sensor port includes at least four sensor port contacts configured to contact the first analyte sensor upon insertion of the first analyte sensor into the sensor port, at least three sensor port contacts configured to contact the second analyte sensor upon insertion of the second analyte sensor into the sensor port, a top portion and a bottom portion engaged with the top portion, wherein the at least three sensor port contacts are attached to the top portion of the sensor port.

In another embodiment of the first aspect, the sensor port includes at least four sensor port contacts configured to contact the first analyte sensor upon insertion of the first analyte sensor into the sensor port, at least three sensor port contacts configured to contact the second analyte sensor upon insertion of the second analyte sensor into the sensor port, a top portion, a bottom portion engaged with the top portion, and a protective protrusion extending from the top portion of the sensor port into the interior of the sensor port.

In a second aspect of the present disclosure, a sensor port is provided which includes a sensor port housing and a plurality of sensor port contacts positioned in the sensor port housing, wherein the sensor port is configured to receive a first analyte sensor having a first width and a second analyte sensor having a second width, wherein the first and second widths are different.

In one embodiment of the second aspect, the sensor port includes a side wall and a biasing mechanism configured to position the analyte sensors against the sidewall during insertion of the analyte sensors.

In another embodiment of the second aspect, the first analyte sensor has a width which is greater than that of the second analyte sensor.

In another embodiment of the second aspect, the first analyte sensor has a width which is less than that of the second analyte sensor.

In a third aspect of the present disclosure, an analyte meter is provided which includes an analyte meter housing; a sensor port coupled to the analyte meter housing, wherein the sensor port includes a sensor port housing and a plurality of sensor port contacts positioned in the sensor port housing, and wherein the sensor port is configured to receive a first analyte sensor having an opposing electrode configuration and a second analyte sensor having a co-planar electrode configuration; and a processing unit coupled to the analyte meter housing, wherein the processing unit is configured to receive from the first and second analyte sensors one or more signals indicative of an analyte concentration in a sample and thereby determine the analyte concentration in the sample.

In one embodiment of the third aspect, the first analyte sensor is a glucose sensor and the second analyte sensor is a ketone sensor.

In another embodiment of the third aspect, both the first and second analyte sensors are glucose sensors.

In another embodiment of the third aspect, the analyte meter includes a communication unit.

In another embodiment of the third aspect, the analyte meter includes a communication unit, and the communication unit is configured to provide two-way communication between the analyte meter and a device and/or network external to the analyte meter.

In another embodiment of the third aspect, the analyte meter includes a communication unit, and the communication unit is configured to provide two-way communication between the analyte meter and a network external to the analyte meter.

In another embodiment of the third aspect, the analyte meter includes a communication unit, the communication unit is configured to provide two-way communication between the analyte meter and a network external to the analyte meter, and the network is a computer network.

In another embodiment of the third aspect, the analyte meter includes a communication unit, and the communication unit includes a Universal Serial Bus (USB) connector.

In another embodiment of the third aspect, the analyte meter includes a communication unit, and the communication unit is configured to provide wireless communication between the analyte meter and an external device and/or network.

In another embodiment of the third aspect, the analyte meter includes a communication unit, the communication unit is configured to provide wireless communication between the analyte meter and an external device and/or network, and the communication unit utilizes a wireless communication protocol selected from a radio frequency (RF) protocol and an infrared (IR) protocol.

In another embodiment of the third aspect, the sensor port includes a communication unit, the communication unit is configured to provide wireless communication between the sensor port and an external device, the external device includes a Radio-Frequency Identification (RFID) tag, and the communication unit utilizes an RF wireless communication protocol to communicate with the Radio-Frequency Identification (RFID) tag.

In another embodiment of the third aspect, the analyte meter includes a communication unit, the communication unit is configured to provide wireless communication between the analyte meter and an external device and/or network, and the communication unit utilizes a wireless communication protocol selected from ZigBee®, WiFi®, Bluetooth®, code division multiple access (CDMA) and Global System for Mobile communications (GSM).

In another embodiment of the third aspect, the analyte meter includes a communication unit, and the communication unit is configured to provide wireless communication between the analyte meter and an external device.

In another embodiment of the third aspect, the analyte meter includes a communication unit, the communication unit is configured to provide wireless communication between the analyte meter and an external device, and the external device is a medication delivery device or an implanted or partially implanted analyte sensor.

In another embodiment of the third aspect, the analyte meter includes a communication unit, the communication unit is configured to provide wireless communication between the analyte meter and an external device, and the external device is an insulin pump.

In another embodiment of the third aspect, the analyte meter includes a display unit in communication with the processing unit.

In another embodiment of the third aspect, the analyte meter includes a display unit in communication with the processing unit, and the display unit includes a touch screen.

In another embodiment of the third aspect, the analyte meter includes a display unit in communication with the processing unit, and the display unit includes a liquid crystal display (LCD).

In another embodiment of the third aspect, the sensor port is configured to receive analyte sensors having different widths.

In another embodiment of the third aspect, the sensor port is configured to receive analyte sensors having different widths, and the sensor port includes a side wall and a biasing mechanism configured to position the analyte sensors against the sidewall during insertion of the analyte sensors.

In another embodiment of the third aspect, the sensor port is configured to receive analyte sensors having different widths, and the first analyte sensor has a width which is greater than that of the second analyte sensor.

In another embodiment of the third aspect, the sensor port is configured to receive analyte sensors having different widths, and the first analyte sensor has a width which is less than that of the second analyte sensor.

In another embodiment of the third aspect, the sensor port includes an analyte sensor ejector slidably engaged therewith.

In another embodiment of the third aspect, the sensor port includes at least four sensor port contacts configured to contact the first analyte sensor upon insertion of the first analyte sensor into the sensor port and at least three sensor port contacts configured to contact the second analyte sensor upon insertion of the second analyte sensor into the sensor port.

In another embodiment of the third aspect, the sensor port includes at least seven different sensor port contacts, including four sensor port contacts configured to contact the first analyte sensor upon insertion of the first analyte sensor into the sensor port and at least three sensor port contacts configured to contact the second analyte sensor upon insertion of the second analyte sensor into the sensor port.

In another embodiment of the third aspect, the sensor port includes at least nine different sensor port contacts, including four sensor port contacts configured to contact the first analyte sensor upon insertion of the first analyte sensor into the sensor port and at least three sensor port contacts configured to contact the second analyte sensor upon insertion of the second analyte sensor into the sensor port.

In another embodiment of the third aspect, the sensor port includes at least four sensor port contacts configured to contact the first analyte sensor upon insertion of the first analyte sensor into the sensor port, at least three sensor port contacts configured to contact the second analyte sensor upon insertion of the second analyte sensor into the sensor port, a top portion and a bottom portion engaged with the top portion.

In another embodiment of the third aspect, the sensor port includes at least four sensor port contacts configured to contact the first analyte sensor upon insertion of the first analyte sensor into the sensor port, at least three sensor port contacts configured to contact the second analyte sensor upon insertion of the second analyte sensor into the sensor port, a top portion and a bottom portion engaged with the top portion, wherein one of the at least four sensor port contacts is attached to the top portion of the sensor port and three of the at least four sensor port contacts are attached to the bottom portion of the sensor port.

In another embodiment of the third aspect, the sensor port includes at least four sensor port contacts configured to contact the first analyte sensor upon insertion of the first analyte sensor into the sensor port, at least three sensor port contacts configured to contact the second analyte sensor upon insertion of the second analyte sensor into the sensor port, a top portion and a bottom portion engaged with the top portion, wherein the at least three sensor port contacts are attached to the top portion of the sensor port.

In another embodiment of the third aspect, the sensor port includes at least four sensor port contacts configured to contact the first analyte sensor upon insertion of the first analyte sensor into the sensor port, at least three sensor port contacts configured to contact the second analyte sensor upon insertion of the second analyte sensor into the sensor port, a top portion and a bottom portion engaged with the top portion, wherein the sensor port includes a protective protrusion extending from the top portion of the sensor port into the interior of the sensor port.

In a fourth aspect of the present disclosure, an analyte meter is provided which includes an analyte meter housing; a sensor port coupled to the analyte meter housing, wherein the sensor port includes a sensor port housing and a plurality of sensor port contacts positioned in the sensor port housing, and wherein the sensor port is configured to receive a first analyte sensor having a first width and a second analyte sensor having a second width, wherein the first and second widths are different; and a processing unit coupled to the analyte meter housing, wherein the processing unit is configured to receive from the first and second analyte sensors one or more signals indicative of an analyte concentration in a sample and thereby determine the analyte concentration in the sample.

In one embodiment of the fourth aspect, the sensor port includes a side wall and a biasing mechanism configured to position the analyte sensors against the sidewall during insertion of the analyte sensors.

In another embodiment of the fourth aspect, the first analyte sensor has a width which is greater than that of the second analyte sensor.

In another embodiment of the fourth aspect, the first analyte sensor has a width which is less than that of the second analyte sensor.

In a fifth aspect of the present disclosure, a medical device is provided which includes a medical device housing and a sensor port coupled to the medical device housing, wherein the sensor port includes a sensor port housing and a plurality of sensor port contacts positioned in the sensor port housing, wherein the sensor port is configured to receive a first analyte sensor having an opposing electrode configuration and a second analyte sensor having a co-planar electrode configuration.

In one embodiment of the fifth aspect, the medical device is a medication delivery device.

In another embodiment of the fifth aspect, the medication delivery device is an insulin pump.

In another embodiment of the fifth aspect, the medical device is an analyte meter.

In a sixth aspect of the present disclosure, a medical device is provided which include a medical device housing and a sensor port coupled to the medical device housing, wherein the sensor port includes a sensor port housing and a plurality of sensor port contacts positioned in the sensor port housing, and wherein the sensor port is configured to receive a first analyte sensor having a first width and a second analyte sensor having a second width, wherein the first and second widths are different.

In one embodiment of the sixth aspect, the sensor port includes a side wall and a biasing mechanism configured to position the analyte sensors against the sidewall during insertion of the analyte sensors.

In another embodiment of the sixth aspect, the first analyte sensor has a width which is greater than that of the second analyte sensor.

In another embodiment of the sixth aspect, the first analyte sensor has a width which is less than that of the second analyte sensor.

It should be noted that two or more of the embodiments described herein, including those described above, may be combined to produce one or more additional embodiments which include the combined features of the individual embodiments.

BRIEF DESCRIPTION OF THE DRAWINGS

The disclosure is best understood from the following detailed description when read in conjunction with the accompanying drawings. It is emphasized that, according to common practice, the various features of the drawings are not necessarily to-scale. The dimensions of the various features are arbitrarily expanded or reduced for clarity. Included in the drawings are the following figures:

FIG. 3A, FIG. 3B and FIG. 3C show top, side and bottom views respectively of an embodiment of a sensor port according to the present disclosure with an analyte sensor inserted therein, wherein the analyte sensor has an opposing electrode configuration;

As shown in FIG. 16, each of the Input Unit, Display Unit, Data Storage Unit and Communication Unit can be integrated into the housing of the analyte meter. In some embodiments, one or more of the Input Unit, Display Unit, Data Storage Unit and Communication Unit are provided as a separate modular hardware unit capable of releasably engaging with the housing of the analyte meter to form an integrated unit. In other embodiments, one or more of the Input Unit, Display Unit, Data Storage Unit and Communication Unit are provided as a separate device or as a component of a separate device which is configured to communicate with the analyte meter and thus transfer data between the device or component and the processing unit of the analyte meter. In some embodiments, the Display Unit and the Input Unit are integrated into a single unit, e.g., a touch screen display. FIG. 16 also depicts a variety of optional devices and/or systems one or more of which can be configured to communicate with the analyte meter, e.g., a medication delivery device and/or system, a portable processing device, a computer, a network, an internet, and an analyte monitoring device and/or system;

FIG. 21B shows a rear view (top) of the medication delivery device shown in FIG. 21B and a side view (bottom) of the sensor port shown in FIG. 21A;

Figure 1:
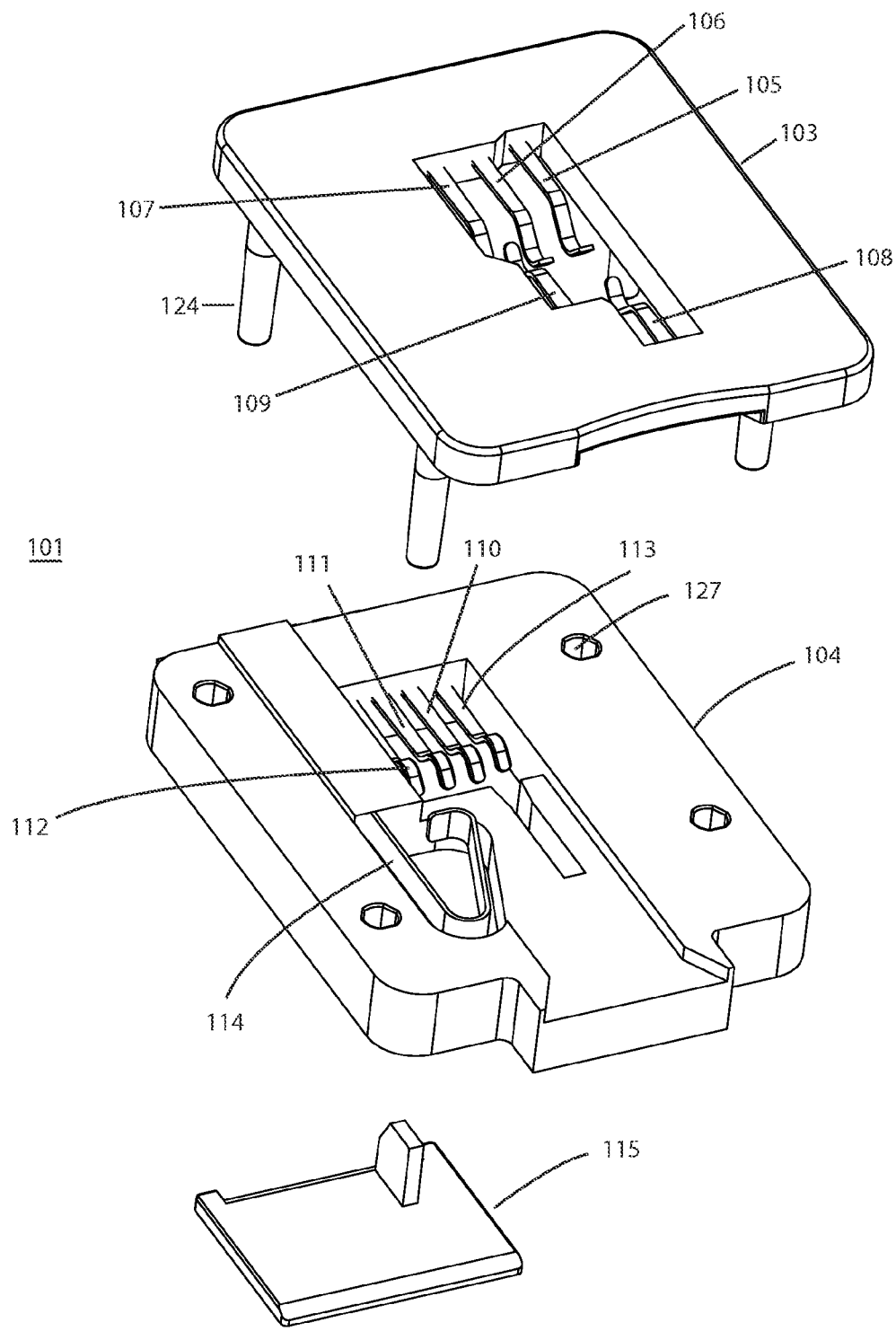
FIG. 1 shows an exploded view of an embodiment of a sensor port according to the present disclosure.
Figure 2B:
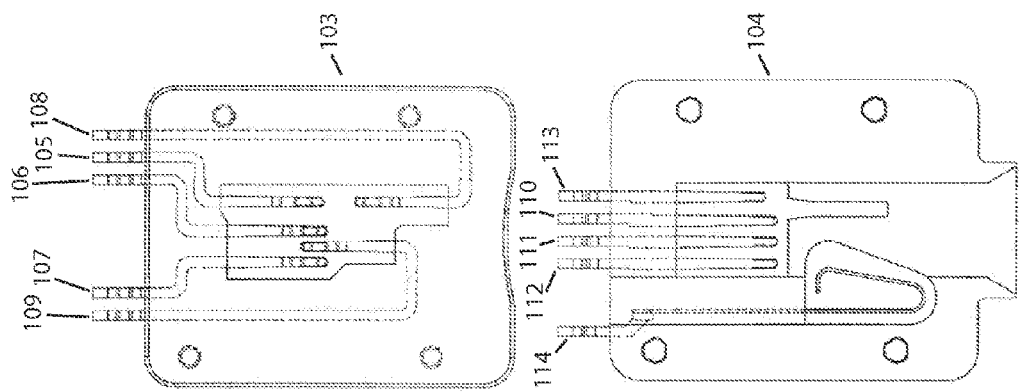
FIG. 2B shows a top view of the top and bottom portions of an embodiment of a sensor port according to the present disclosure.
Figure 2A:
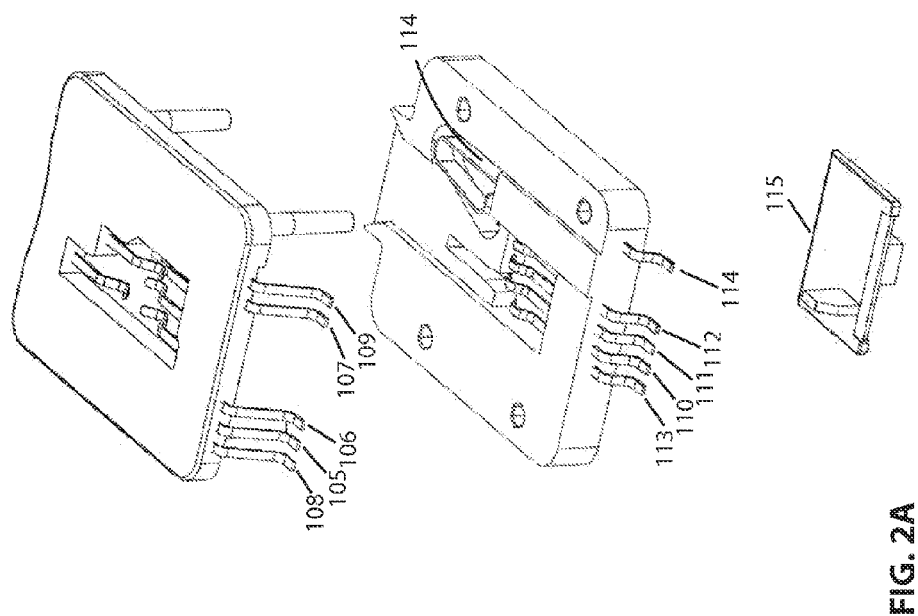
FIG. 2A shows another exploded view of an embodiment of a sensor port according to the present disclosure.

Before the present invention is further described, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

As used herein and in the appended claims, the singular forms "a," "and," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. All publications mentioned herein are incorporated herein by reference to disclose and describe the methods and/or materials in connection with which the publications are cited.

DETAILED DESCRIPTION

Sensor Ports

The present disclosure provides sensor ports configured to receive a plurality of analyte sensors having different electrode configurations and/or different sizes and/or shapes. These sensor ports find use in a variety of devices, including, e.g., analyte meters, analyte monitoring devices and/or systems (e.g., an integrated device in communication with an implanted or partially implanted analyte monitoring device) and drug delivery systems and/or devices. The sensor ports provide an electrical connection between an analyte sensor and a device which includes the sensor port configured to receive the analyte sensor.

Sensor Port Configured to Receive Analyte Sensors Having Opposing and Co-Planar Electrode Configurations In some embodiments, a sensor port according to the present disclosure is configured such that it is capable of receiving at least two different types of analyte sensors, e.g., a first type having an opposing electrode configuration and a second type having a co-planar electrode configuration. As used in the context of the analyte sensors described herein, the term "opposing electrode configuration" means that at least one of the electrodes of the analyte sensor is positioned in opposition to another electrode of the analyte sensor, e.g., by being positioned on opposing substrates of the analyte sensor. As used in the context of the analyte sensors described herein, the term "co-planar electrode configuration" means that all of the electrodes of the analyte sensor are positioned in the same horizontal plane, e.g., by all electrodes being positioned on a common substrate of the analyte sensor. Thus, in some embodiments, a sensor port according to the present disclosure may be used to receive the first type of analyte sensor at a first time point and the same sensor port may be used to receive the second type of analyte sensor at a second time point. In some embodiments, the analytes measured using the first and second types of analyte sensors are the same. In other embodiments, the analytes measured using the first and second types of analyte sensors are different, e.g., glucose and ketone.

In one embodiment, as illustrated in FIG. 1, FIGS. 2A-2B, FIGS. 3A-3C, and FIGS. 4A-4C, a sensor port 101 includes a sensor port housing 102 and is configured to receive a first analyte sensor 200 having an opposing electrode configuration and a second analyte sensor 300 having a co-planar electrode configuration.

In some embodiments, sensor port housing 102 is a two-part structure, having a top portion 103 and a bottom portion 104 (See, e.g., FIG. 1) which engage to form sensor port housing 102. Top portion 103 and bottom portion 104 may engage via a variety of different engagement mechanisms. For example, the figures set forth herein depict an embodiment in which connection stilts 124 are inserted through connection stilt receiving holes 127 to engage top portion 103 with bottom portion 104. Secured by top portion 103 and bottom portion 104 are various sensor port contacts that provide electrical connection between an inserted analyte sensor (e.g., analyte sensor 200 or 300) and a device including sensor port 101, e.g., an analyte meter 100 (See, e.g., FIG. 13).

Any suitable conductive material or combination of conductive materials known in the art may be utilized for the sensor port contacts, e.g., tempered phosphor bronze (e.g., UNS C51000—5% Sn, UNS C52100—8% Sn, and UNS C52400—10% Sn), beryllium copper (e.g., UNS C17000, UNS 17200, and UNS 17300) titanium, nickel, stainless steel, platinum, carbon, gold, etc., provided the material is sufficiently conductive to allow transfer of an electrical signal from one or more electrodes of an inserted analyte sensor. While the above refers to a two-part housing structure, it should be noted that in other embodiments housing 102 may be formed as a single structural unit, e.g., injection molded as a single structural unit.

An exemplary configuration for the various sensor port contacts of sensor port 101 is now described with reference to FIG. 1, FIGS. 2A-2B, FIGS. 3A-3C, and FIGS. 4A-4C. Top portion 103 includes sensor port contacts 105, 106, 107, 108 and 109. Bottom portion 104 includes sensor port contacts 110, 111, 112 and 113. In one embodiment, sensor port contacts 105—113 are configured and positioned in sensor port 101 such that sensor port contacts 105, 110, 111 and 112 contact electrode contacts present on an analyte sensor having an opposing electrode configuration when the analyte test strip is inserted into sensor port 101 (See, e.g., FIGS. 3A-3C) and sensor port contacts 105, 106 and 107 contact electrode contacts present on an analyte sensor having a co-planar electrode configuration (See, e.g., FIGS. 4A-4C) when the analyte sensor is inserted into sensor port 101. Thus, in some embodiments, at least one sensor port contact, e.g., sensor port contact 105, is configured to contact an electrode contact of a first analyte sensor having an opposing electrode configuration and an electrode contact of a second analyte sensor having a co-planar electrode configuration.

It should be noted that in some embodiments the relative positioning of "top portion" 103 and "bottom portion" 104 could be reversed to produce a bottom mount design in which portion 104 includes sensor port contacts 105, 106, 107, 108 and 109; and portion 103 includes sensor port contacts 110, 111, 112 and 113.

Figure 14:
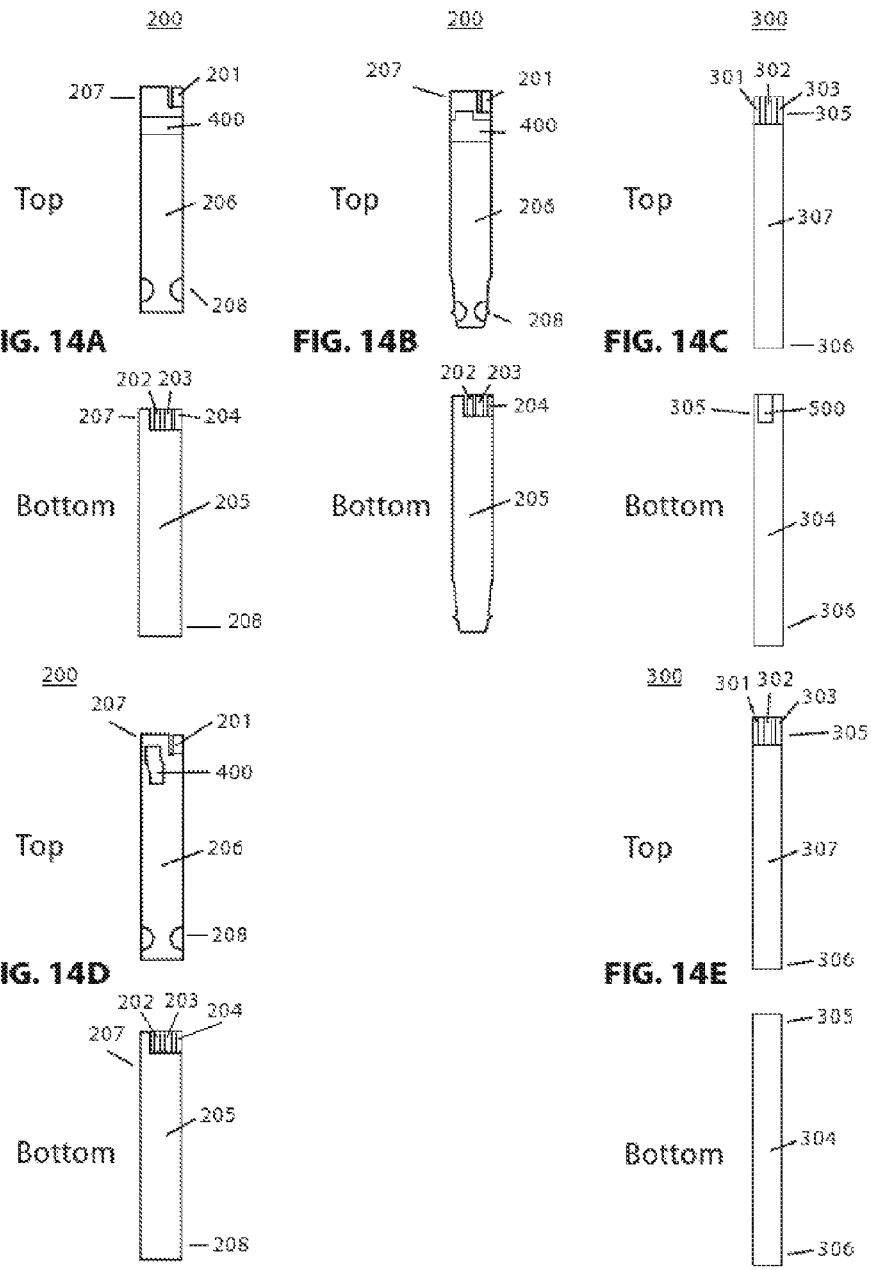
FIG. 14A shows a top and bottom view of an analyte sensor having an opposing electrode structure.
FIG. 14B shows a top and bottom view of an analyte sensor having an opposing electrode structure.
FIG. 14C shows a top and bottom view of an analyte sensor having a co-planar electrode configuration.
FIG. 14D shows a top and bottom view of an analyte sensor having an opposing electrode configuration.
FIG. 14E shows a top and bottom view an analyte sensor having a co-planar electrode configuration.

Examples of suitable analyte sensors, e.g., test strips, having opposing or co-planar electrode configurations are depicted in FIGS. 14A-14E. As shown in FIG. 14A, an analyte sensor 200 has an opposing electrode configuration with electrode contact 201 positioned on a first substrate 205, electrode contacts 202, 203 and 204 positioned on a second substrate 206, wherein the first and second substrates are separated by a spacer (not shown). Additional embodiments of analyte sensors 200 are shown in FIG. 14B and FIG. 14D. Analyte sensors of this type include analyte test strips available from Abbott Diabetes Care Inc., Alameda, Calif., e.g., FreeStyle® and FreeStyle Lite® glucose monitoring test strips. As shown in FIGS. 14C and 14E, analyte sensors 300 have a co-planar electrode configuration with electrode contacts 301, 302 and 303 positioned on a substrate 304. Analyte sensors of this type include analyte test strips available from Abbott Diabetes Care Inc., Alameda, Calif., e.g., Precision Extra® and Precision XceedPro® glucose and ketone monitoring test strips.

In one embodiment, with reference to FIGS. 3A-3C and 14B, the sensor port 101 is configured such that upon insertion of analyte sensor 200 into sensor port 101, electrode contact 201 comes into contact with sensor port contact 105; electrode contact 202 comes into contact with sensor port contact 110; electrode contact 203 comes into contact with sensor port contact 111; and electrode contact 204 comes into contact with sensor port contact 112. With reference to FIGS. 4A-4C and 14C, sensor port 101 is also configured such that upon insertion of analyte sensor 300 into sensor port 101, electrode contact 301 comes into contact with sensor port contact 107; electrode contact 302 comes into contact with sensor port contact 106; and electrode contact 303 comes into contact with sensor port contact 105. Thus, a sensor port capable of receiving both analyte sensors having an opposing electrode configuration and analyte sensors having a co-planar electrode configuration is provided.

Additional Sensor Port Contacts

In some embodiments, a sensor port 101 according to the present disclosure will include additional sensor port contacts which provide additional functionality to a device which includes the sensor port 101.

Turn-on Monitor Contact(s)

The sensor ports disclosed herein can include one or more sensor port contacts which function as turn-on monitor contact(s). In one embodiment, sensor port 101 includes optional sensor port contacts 108 and 109 as depicted in FIGS. 3A-3C, which function as turn-on monitor contacts. Turn-on monitor contacts 108 and 109 are configured to contact a corresponding turn-on monitor 400 present on an analyte sensor, e.g., an analyte sensor 200 as shown in FIG. 14B. In combination with the turn-on monitor 400, the turn-on monitor contacts 108 and 109 facilitate certain functions of a device which includes a sensor port 101, e.g. an analyte meter 100. For example, in one embodiment, turn-on monitor contacts 108 and 109 are designed to facilitate detection of an analyte sensor 200 by analyte meter 100 upon insertion of analyte sensor 200 into sensor port 101. In one embodiment, such detection results in activation of analyte meter 100 for testing, i.e., turn-on monitor 400 facilitates a "turn-on" function of analyte meter 100 in the absence of further action by the user such as manipulation of a switch on the analyte meter.

It should be noted that while the configuration shown for turn-on monitor contacts 108 and 109 in FIGS. 3A-3C is such that they contact a turn-on monitor 400 having the shape and/or configuration shown in FIG. 14B, such a configuration is merely exemplary, and the configuration of the turn-on monitor contacts can be varied to accommodate turn-on monitors having a variety of different shapes and or configurations as discussed in more detail below. For example, in one embodiment, turn-on monitor contacts 108 and 109 are configured such that they both contact a turn-on monitor 400 having the shape and/or configuration shown in FIG. 14A.

Assay Determination Contacts

Figure 4C:
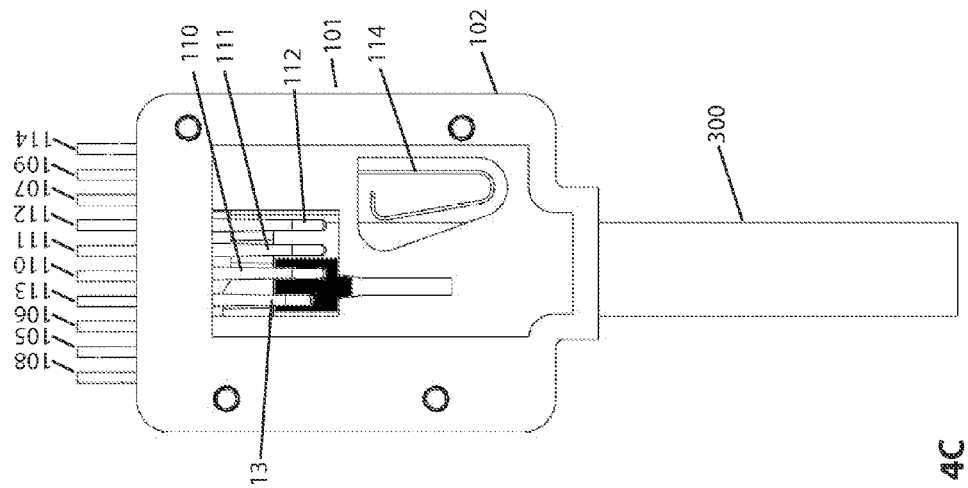
FIG. 4A, FIG. 4B and FIG. 4C show top, side and bottom views respectively of an embodiment of a sensor port according to the present disclosure with an analyte sensor inserted therein, wherein the analyte sensor has a co-planar electrode configuration.
Figure 4B:
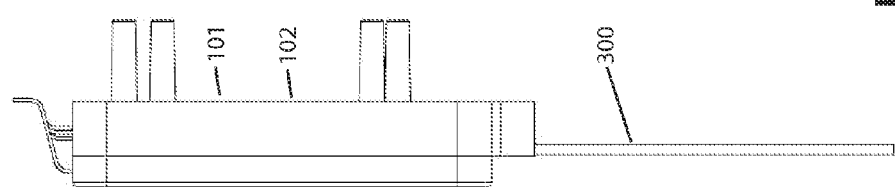
Figure 4A:
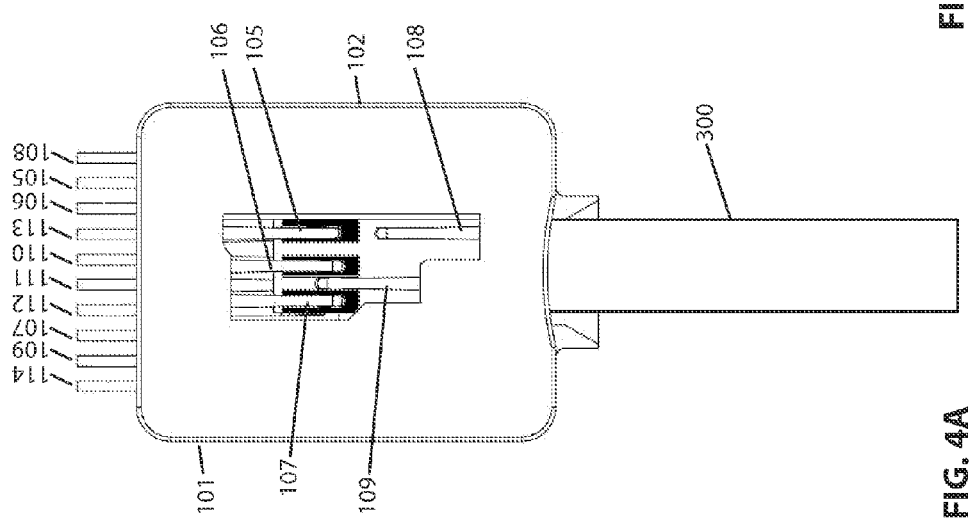

In addition, or alternatively, the sensor ports disclosed herein can include one or more sensor port contacts which function as assay determination contacts. Assay determination contacts allow an analyte meter 100 or other device including a sensor port 101 to determine that the analyte sensor is configured for a particular type of analyte measurement assay. For example, in one embodiment sensor port 101 includes optional sensor port contact 113 as depicted in FIGS. 4A-4C, which functions either alone or in combination with one of the other sensor port contacts, as an assay determination contact. Assay determination contact 113 is configured to contact a corresponding assay indicator contact 500 present on an analyte sensor configured to perform a particular type of analyte measurement assay, e.g., an analyte sensor 300 configured to perform a particular type of analyte measurement assay, e.g., a glucose measurement assay or a ketone measurement assay.

In some embodiments, an assay determination contact, e.g., an assay determination contact 113, works together with one of the other sensor port contacts of sensor port 101 to provide a particular functionality. For example, in one embodiment, as depicted in FIGS. 4A-4C, assay determination contact 113, together with sensor port contact 110, contact assay indicator contact 500 to complete an electrical circuit which indicates to a device including sensor port 101 that the analyte sensor is configured for a particular assay, e.g., a glucose measurement assay or a ketone measurement assay.

Assay determination contact 113 together with sensor port contact 110 can also facilitate determination of the assay configuration of an analyte sensor lacking an assay indicator contact 500. For example, failure to complete an electrical circuit between determination contact 113 and sensor port contact 110 due to the absence of indicator contact 500 can indicate one of two analyte sensor assay configurations, e.g., glucose measurement, while completion of the electrical circuit due to the presence of indicator contact 500 indicates the second analyte sensor assay configuration, e.g., ketone measurement. Accordingly, differently configured analyte sensors can be configured for identification by the sensor port by either including or not including an assay indicator contact such as assay indicator contact 500.

In some embodiments, an assay determination contact, either alone or in combination with another sensor port contact, functions as a turn-on monitor contact and vice versa. In other words, in some embodiments, an assay determination contact can provide a "turn-on" function, and, in some embodiments, a turn-on monitor contact can provide an "assay determination" function to a device which includes a sensor port 101, e.g., an analyte meter 100.

As discussed above, in some embodiments, detection of the turn-on monitor and/or the assay indicator contact is accomplished electrically. For example, a turn-on monitor and/or assay indicator contact can be configured to close or open an electrical circuit when the analyte sensor is inserted into the sensor port of an analyte meter. In some embodiments, closing or opening the electrical circuit in turn activates the analyte meter for testing. The turn-on monitor and/or the assay indicator contact can include a conductive material which facilitates electrical detection of the turn-on monitor and/or the assay indicator contact. For example, in the embodiment shown in FIG. 14A, turn-on monitor 400 includes a conductive material in the form of a conductive strip extending across an exterior surface of analyte sensor 200.

In some embodiments, the turn-on monitor and/or the assay indicator contact is designed such that it physically opens or closes an electric circuit in an analyte meter upon insertion. For example, the turn-on monitor and/or the assay indicator contact could be configured as a dimple or a protrusion which physically opens or closes an electric circuit upon insertion of the analyte sensor into the sensor port.

In other embodiments, detection of the analyte sensor and/or determination of the assay configuration of the analyte sensor is accomplished mechanically without the analyte sensor directly opening or closing an electrical circuit. For example, the turn-on monitor and/or the assay indicator contact may have a physical structure which engages with a corresponding physical structure in the sensor port, e.g., in a "lock and key" type configuration. The turn-on monitor and/or the assay indicator contact may include a first physical structure configured to engage with a second physical structure present in the sensor port, wherein the physical structure present on the analyte sensor includes at least one cutout and/or protrusion, wherein the shape, dimensions and/or number of the at least one cutout and/or protrusion engages with a corresponding physical structure in the sensor port. The forming of a particular cutout and/or protrusion shape may be accomplished by several methods. For example, the specific cutout and/or protrusion shape may be formed by cutting to a desired shape. The cutting may be done, by, for example, a laser such as a laser-ablation method. The sensor port can be configured such that this physical interaction in turn facilitates turn-on and/or assay configuration determination functions of the analyte meter as described above.

Turn-on monitors and/or assay indicator contacts may have any suitable configuration, including but not limited to, a stripe extending across the analyte sensor from a side edge to a side edge, such as the embodiment shown in FIGS. 14A and 14B; a stripe extending across the analyte sensor, although not the entire width; and an array of unconnected dots, strips, or other areas. In some embodiments, a turn-on monitor and/or assay indictor contact is configured to convey calibration information for the analyte sensor to a device including a sensor port 101. Suitable configurations which may be utilized for turn-on monitors and/or assay configuration contacts are provided in U.S. Patent Application Publication No. 2006/0091006; U.S. Patent Application Publication No. 2008/0267823; U.S. Pat. Nos. 6,592,745; 6,143,164; 6,071,391; 6,503,381; 6,616,819; 6,773,671 and 6,893,545; the disclosures of each of which are incorporated by reference herein.

Sensor Port Configured to Receive Analyte Sensors Having Different Widths

The present disclosure provides sensor ports configured to receive a plurality of analyte sensors having different widths e.g., a plurality of analyte test strips having different widths.

In one embodiment, in order to facilitate insertion and proper positioning of the analyte sensors in the sensor port, the sensor port includes an optional biasing mechanism configured to bias the analyte sensor against a side wall of the sensor port. Such a configuration allows for positioning of the analyte sensors against a common side wall of the sensor port regardless of the differing widths of the analyte sensors. This in turn facilitates positioning of the analyte sensors relative to the fixed sensor port contacts of the sensor port.

The biasing mechanism may be incorporated into a sensor port configured to receive analyte sensors having opposing and co-planar electrode configurations as described previously herein. Alternatively, the biasing mechanism may be incorporated into a sensor port configured to receive analyte sensors having only opposing or co-planer electrode configurations.

The biasing mechanism may be constructed of any suitable material, provided the material is sufficiently flexible to be deflected from the insertion path of the test strips to be inserted while exerting sufficient force against the inserted test strip to hold it in position against a wall of the test strip port. In some embodiments, the biasing mechanism is in the form of a spring. The spring may be formed from the same material used to form the housing of the test strip port, and, in some embodiments, may be a portion of the housing itself. Alternatively, the spring may be formed from a suitable metal, polymer, etc. and attached to and/or positioned in the sensor port housing. In some embodiments, the biasing mechanism is made from a conductive material. In such embodiments, it may be desirable to configure the biasing mechanism such that it is electrically grounded.

With reference to FIGS. 1, 3A-3C and 4A-4C, a sensor port 101 is provided which includes a biasing mechanism 114. In the context of FIGS. 3A-3C, biasing member 114 exerts sufficient force against analyte sensor 200 to bias analyte sensor 200 against the right side wall of sensor port 101. Similarly, in the context of FIGS. 4A-4C, biasing member 114 exerts sufficient force against analyte sensor 300 to bias analyte sensor 300 against the right side wall of sensor port 101. The sensor port contacts of sensor port 101 are positioned such that when a correctly biased analyte sensor 200 or a correctly biased analyte sensor 300 is inserted, the analyte sensor contacts the appropriate sensor port contacts as discussed previously herein. Accordingly, an analyte sensor port 101 having a fixed sensor port contact arrangement can be configured to accept both an analyte sensor 200 and an analyte sensor 300 despite the differing widths of the analyte sensors.

Although, the figures depict biasing member 114 as positioned on the left-hand side of sensor port 101, it should be understood that such a configuration is for illustration purposes only. For example, a biasing member could be positioned on the right-hand side of sensor port 101 in order to bias analyte sensors against the left side wall of sensor port 101. The sensor port contacts can be repositioned as needed to accommodate for a different positioning of the biasing member. Sensor port 101 could also include multiple biasing members, e.g., biasing members positioned on both the right and left sides of sensor port 101 to bias an inserted analyte sensor to a central position in sensor port 101. The sensor port contacts can be repositioned as needed to accommodate for the positioning of multiple biasing members.

Figure 15:
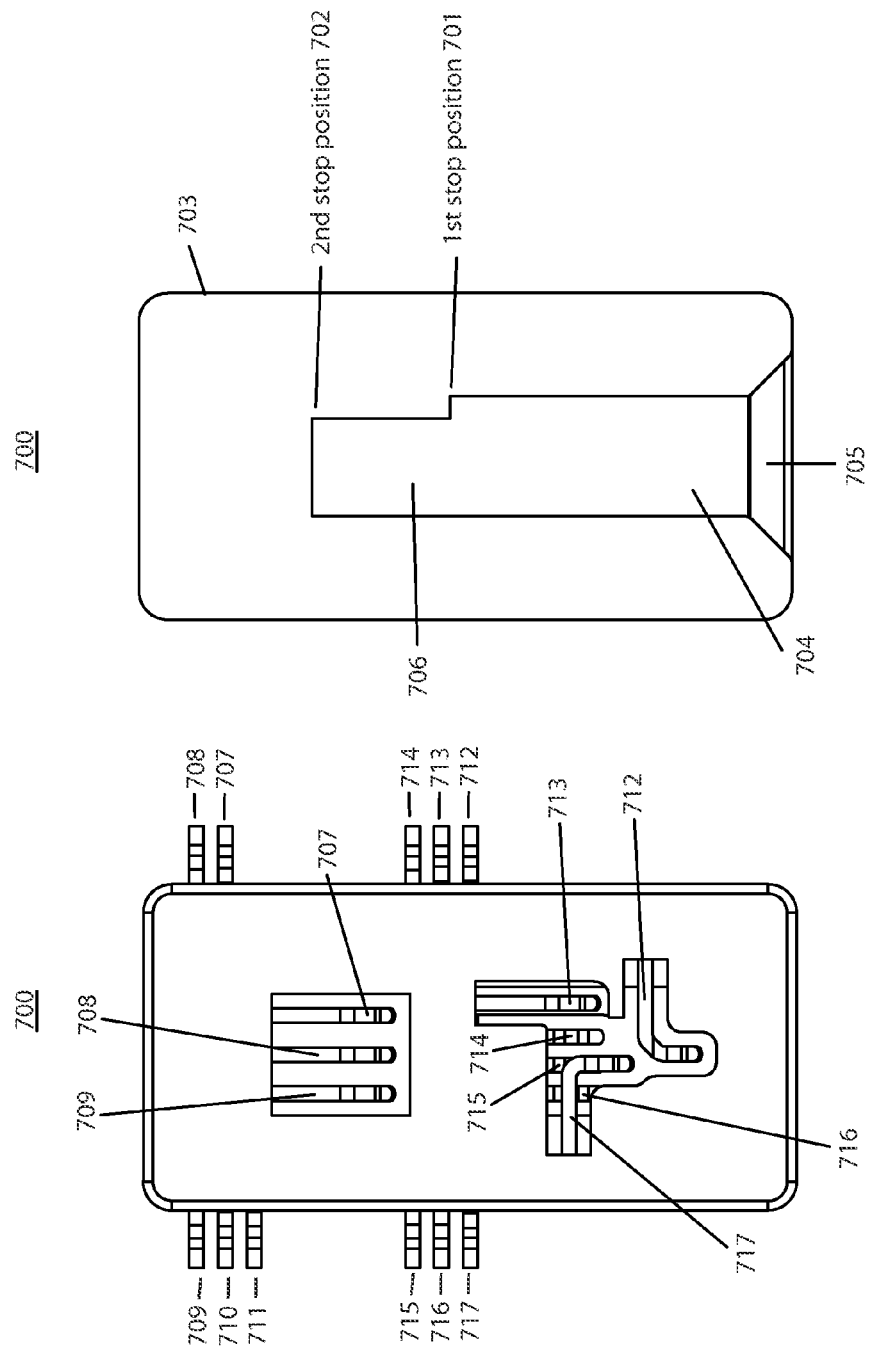
FIG. 15A shows a top view of an embodiment of a sensor port according to the present disclosure, wherein the sensor port is configured to accept analyte sensors having different widths.
FIG. 15B shows a view of the interior space of the sensor port embodiment shown in FIG. 15A. The sensor port contacts are not shown so as to provide a clear view of first and second stop positions.

In another embodiment, with reference to FIGS. 15A and 15B, a sensor port 700 is provided which includes a sensor port housing 703 which is configured to include first and second stop positions (701 and 702) in the interior of sensor port 700. Sensor port housing 703 is configured such that during the analyte sensor insertion process the forward progress of a first analyte sensor, e.g., an analyte sensor 200 (FIGS. 14A, 14B and 14D) is stopped when it reaches first stop position 701. Sensor port housing 703 is further configured such that during a second analyte sensor insertion process the forward progress of a second analyte sensor, e.g., an analyte sensor 300 (FIGS. 14C and 14E) is stopped when it reaches second stop position 702, positioned farther along the analyte sensor insertion path than first stop position 701. As depicted in FIG. 15B, this can be accomplished, for example, by configuring sensor port housing 703 such that insertion area 704 extending from sensor port opening 705 to first stop position 701 is wider than insertion area 706 extending from first stop position 701 to the second stop position 702. It should be noted that the dimensions of insertion areas 704 and 706 and the relative positioning of stop positions 701 and 702 in sensor port 700 may be modified based on the dimensions, e.g., length and width, of the analyte sensors which the sensor port 700 is configured to receive.

With reference to FIG. 15A, sensor port 700 is further configured to include two sets of sensor port contacts, a first set configured to make electrical contact with electrode contacts of a first analyte sensor, e.g., an analyte sensor 200, and a second set configured to make electrical contact with electrode contacts of a second analyte sensor, e.g., an analyte sensor 300. In the embodiment depicted in FIG. 15A, the first set of sensor port contacts is configured to make electrical contact with an analyte sensor having an opposing electrode configuration, and the second set of sensor port contacts is configured to make electrical contact with an analyte sensor having a coplanar electrode configuration. It should be noted, however, that the positioning of the first and second sets could be reversed depending on the relative widths and electrode configurations of the analyte sensors to be inserted. In addition, in some embodiments, the sensor port 700 may be configured to accept two analyte sensors of differing widths having coplanar electrode configurations or two analyte sensors of differing widths having opposing electrode configurations.

With reference to FIG. 15A, in one embodiment, the first set of sensor port contacts includes sensor port contacts 713, 714, 715 and 716 configured such that upon insertion of analyte sensor 200 (FIG. 14D) into sensor port 700, electrode contact 201 comes into contact with sensor port contact 713; electrode contact 202 comes into contact with sensor port contact 714; electrode contact 203 comes into contact with sensor port contact 715; and electrode contact 204 comes into contact with sensor port contact 716. Again, with reference to FIG. 15A, the second set of sensor port contacts includes sensor port contacts 707, 708 and 709. In this embodiment, sensor port 700 is configured such that upon insertion of analyte sensor 300 (FIG. 14C) into sensor port 700, electrode contact 301 comes into contact with sensor port contact 709; electrode contact 302 comes into contact with sensor port contact 708; and electrode contact 303 comes into contact with sensor port contact 707. Thus, a sensor port capable of receiving analyte sensors having different widths is provided.

In one embodiment, e.g., as depicted in FIG. 15A, sensor port 700 includes optional sensor port contacts 712 and 717, which function as turn-on monitor contacts as described previously herein. Turn-on monitor contacts 712 and 717 are configured to contact a corresponding turn-on monitor 400 present on an analyte sensor, e.g., an analyte sensor 200 as shown in FIG. 14D when the analyte sensor is inserted into insertion area 704 of sensor port 700.

In one embodiment, e.g., as depicted in FIG. 15A, sensor port 700 includes optional sensor port contacts 710 and 711, which function as assay determination contacts as described previously herein. Assay determination contacts 710 and 711 are configured to contact a corresponding assay indicator contact 500 present on an analyte sensor, e.g., an analyte sensor 300 as shown in FIG. 14C when the analyte sensor is inserted into insertion area 706 of sensor port 700. In FIG. 15A, the portions of assay determination contacts 710 and 711 which extend into insertion area 706 are positioned below sensor port contacts 708 and 709 respectively and are therefore obscured from view.

Sensor Port Configured to Receive Analyte Sensors Having Voltage-Driven Fill Indicator In some embodiments, the sensor ports disclosed herein are configured to receive analyte sensors, e.g., analyte test strips, configured to include a voltage-driven fill indicator. An analyte sensor configured to include a voltage-driven fill indicator can include a fill-indicator which is visible at an end of the analyte sensor, e.g., an end of the analyte sensor other than an end which is inserted into the analyte meter during the analyte measurement process. In one embodiment, the inclusion of a voltage-driven fill indicator can be implemented using a film which darkens or changes color when sufficient voltage is applied to it. An additional electrode can be included in the analyte sensor which is configured to make electrical contact with the film. The film can be variously positioned on the analyte sensor including, e.g., at an end of the analyte sensor.

An analyte meter configured to receive an analyte sensor including a voltage-driven fill indicator can be configured to sense when the analyte sensor is sufficiently full of liquid (e.g., blood). This can be accomplished, for example, through the use of sensor port contacts configured to contact a pair of fill-indicator electrodes. Additional description of fill-indicator electrodes is provided below and in the materials incorporated by reference herein. The analyte meter can be configured such that when the analyte meter senses that the analyte sensor is sufficiently full of liquid, it applies a voltage to an electrochromic film positioned between the additional electrode and a ground electrode. The film is selected such that the voltage applied by the analyte meter is sufficient to darken the film or effect a change in its color. A variety of films and other electrochromic materials capable of darkening and/or changing color in response to an applied voltage are known in the art, including, e.g., polyaniline, viologens, polyoxotungstates and tungsten oxide. Additional description of an electrochromic film is provided, for example, in U.S. Patent Application Publication No. 2007/0153355, the disclosure of which is incorporated by reference herein. Accordingly, a visual indication of analyte sensor fill can be provided.

Analyte Sensor Ejector

In some embodiments, the sensor ports disclosed herein includes an optional analyte sensor ejector configured to eject an analyte sensor, e.g., an analyte test strip, from the sensor port. An analyte sensor ejector may be useful, for example, where it is desirable to eject an analyte test strip containing a sample of bodily fluid, e.g., blood, following an analyte measurement conducted using an analyte meter including the sensor port. This allows a user of the analyte meter to dispose of the contaminated analyte test strip without touching the analyte test strip.

Figure 5A:
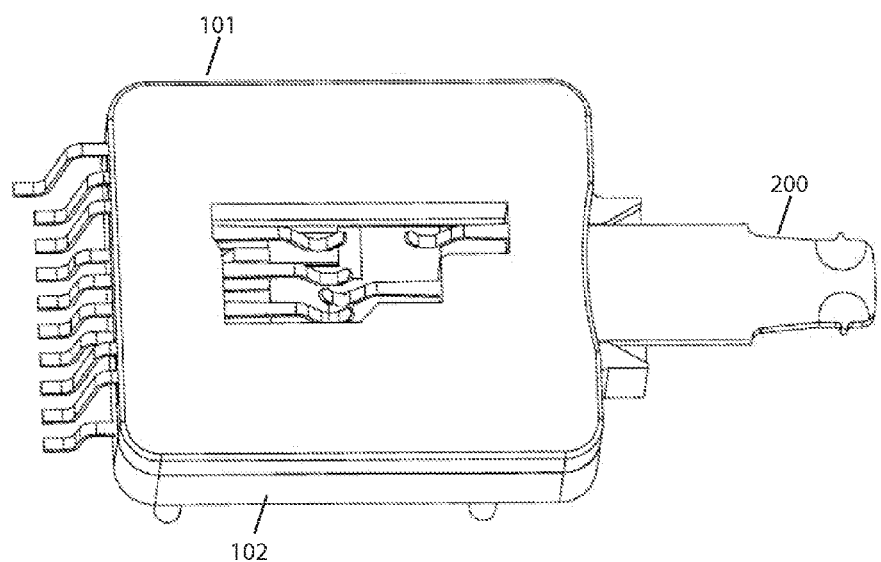
FIG. 5A and FIG. 5B show top and bottom perspective views respectively of an embodiment of a sensor port according to the present disclosure including an optional sensor ejector positioned in a first position with an analyte sensor inserted into the sensor port.
Figure 5B:
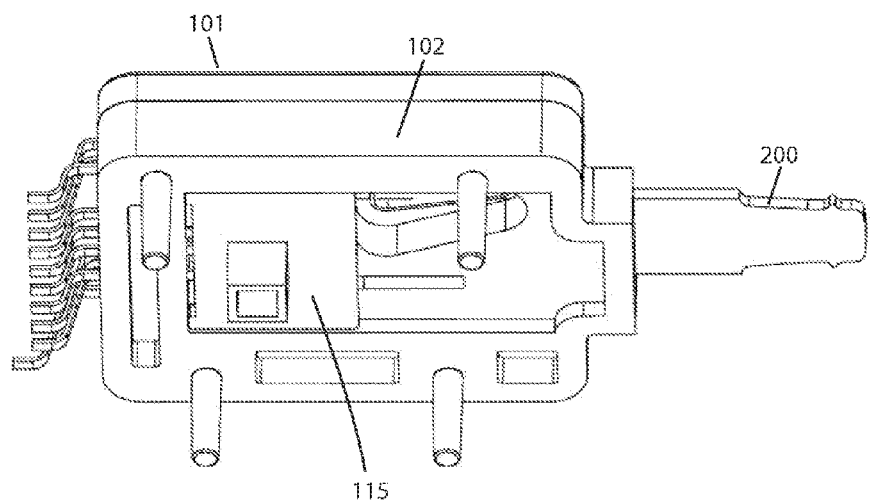
Figure 6A:
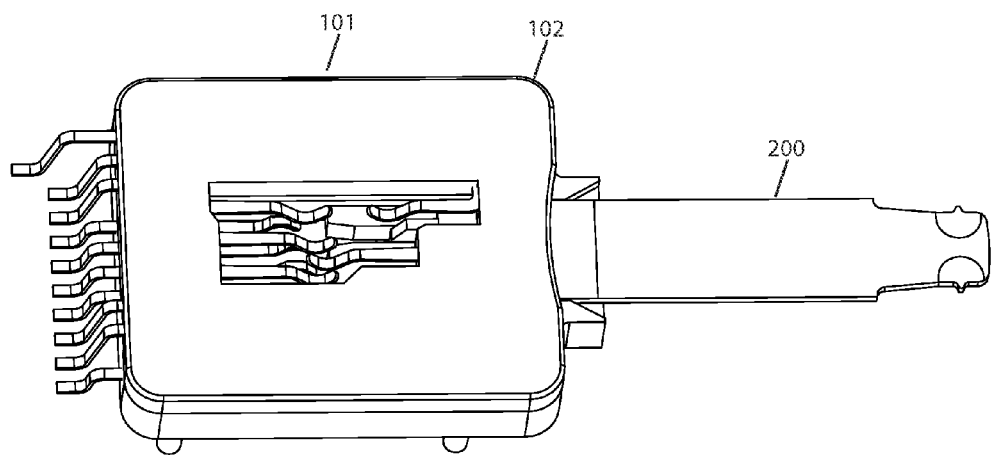
FIG. 6A and FIG. 6B show top and bottom perspective views respectively of the sensor port shown in FIG. 5A and FIG. 5B with the optional sensor ejector positioned in a second position for ejection of the analyte sensor from the sensor port.
Figure 6B:
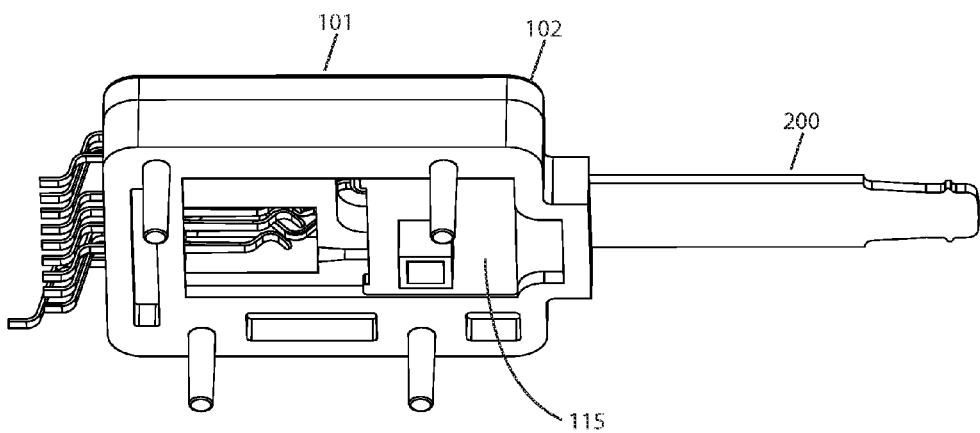

In some embodiments, as shown in FIGS. 1, 5A, 5B, 6A and 6B, an analyte sensor ejector 115 slidably engages bottom portion 104 of sensor port housing 102. The analyte sensor ejector 115 may be configured such that upon insertion of an analyte sensor, e.g., an analyte sensor 200, into sensor port 101, analyte sensor ejector 115 is moved rearward with respect to the sensor port and in the direction of insertion as shown in FIGS. 5A and 5B. In order to eject the analyte sensor, a user physically moves the analyte sensor ejector 115 forward with respect to the sensor port and in the opposite of the direction of insertion as shown in FIGS. 6A and 6B. This movement in-turn exerts force upon the analyte sensor expelling it from the sensor port 101. Alternatively, the analyte sensor ejector may be configured such that insertion of the analyte sensor into a sensor port of the analyte meter positions the analyte sensor ejector in a "cocked" position, e.g., by engaging a spring mechanism. The analyte meter may include a button, switch, or other suitable mechanism for releasing the cocked ejector from the cocked position such that it ejects the analyte sensor from the sensor port of the analyte meter.

Splash-Proof Sensor Port

In some embodiments, a sensor port as disclosed herein is optionally configured as a contamination resistant sensor port and/or a splash-proof sensor port. In one such embodiment, a sensor port includes one or more sealing members positioned so as to limit and/or prevent internal contamination of the sensor port with fluids and/or particles present in the environment outside the sensor port. In another embodiment, the sensor port includes an internal beveled face which can limit and/or prevent ingress of one or more external contaminants into the internal area of the sensor port.

Figure 10:
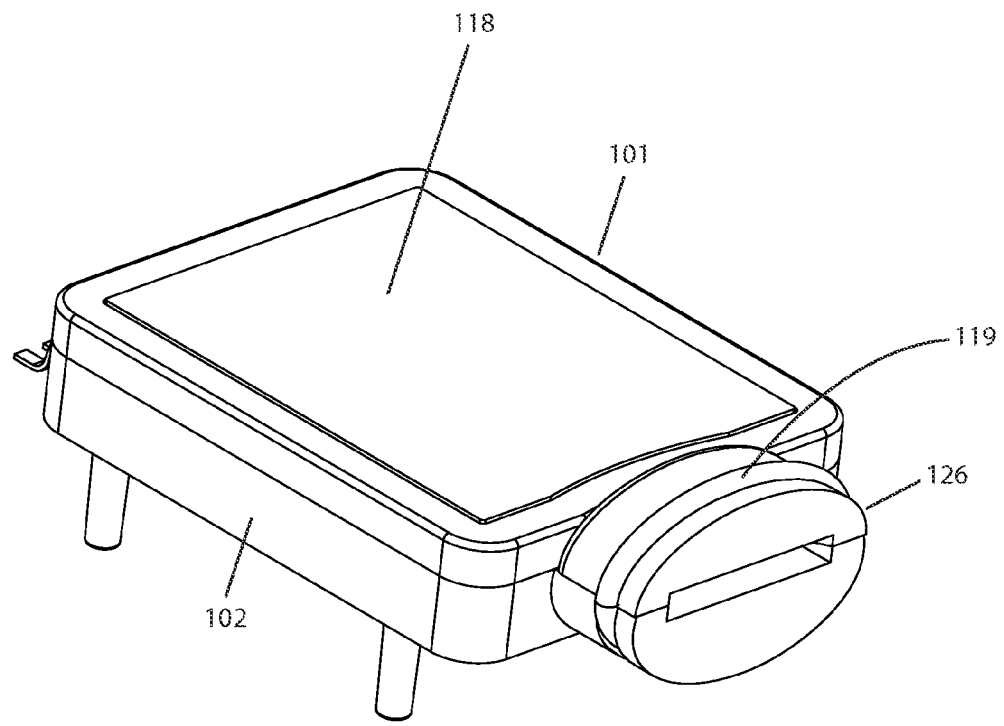
FIG. 10 shows an embodiment of a sensor port according to the present disclosure including optional sealing members.
Figure 11:
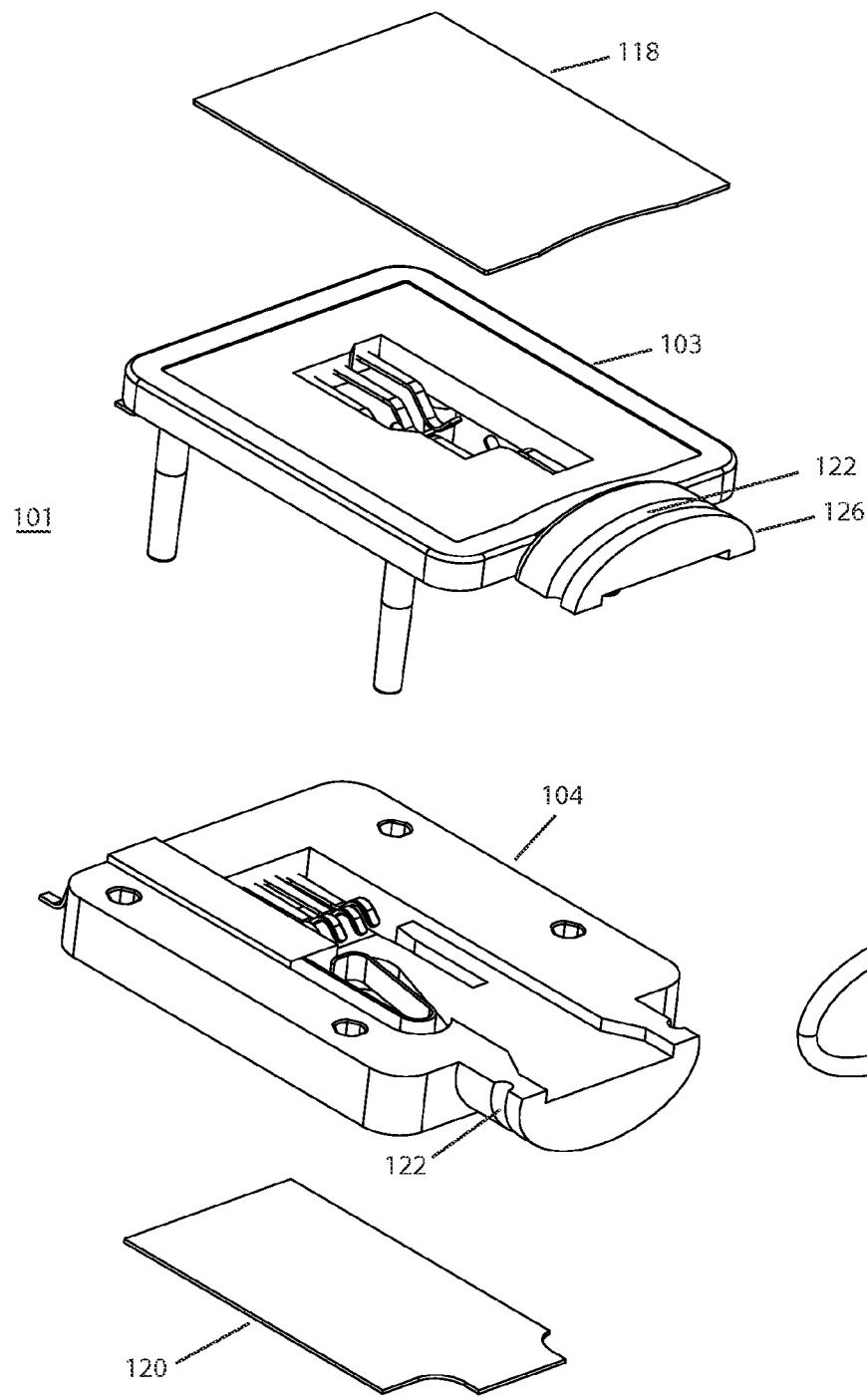
FIG. 11 shows an exploded view of the sensor port shown in FIG. 10.
Figure 12:
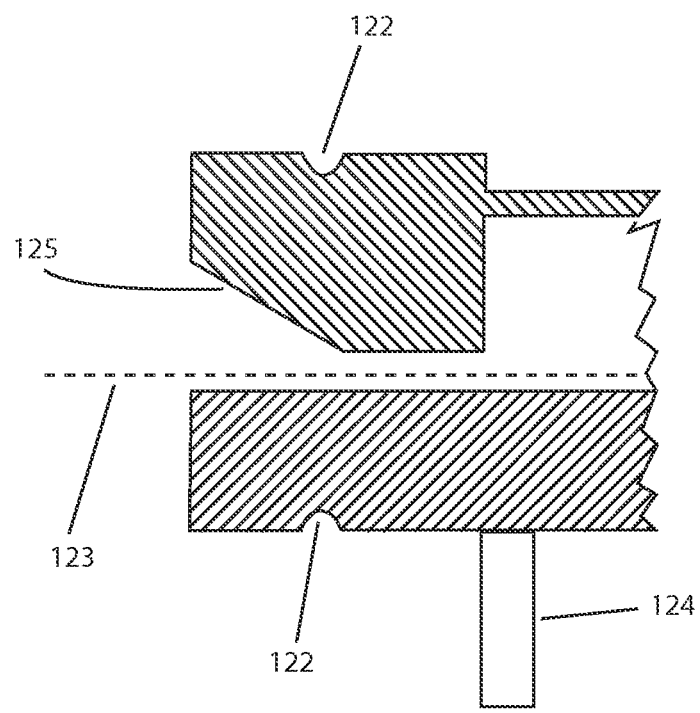
FIG. 12 shows a cross-section view of an embodiment of a sensor port according to the present disclosure including an optional internal beveled face.

With reference to FIGS. 10, 11, and 12, a sensor port 101 is provided which includes a protruding member 126, first sealing member 118, a second sealing member 120 and a third sealing member 119. Third sealing member 119 is positioned in channel 122 circumscribing protruding member 126. In some embodiments, sensor port 101 includes an internal beveled face 125, e.g., as shown in FIG. 12. The angle of the beveled face relative to the plane of insertion 123 can vary. For example, in some embodiments, the angle of the beveled face relative to the plane of insertion 123 is about 25° to about 45°, e.g., about 30° to about 40°. In one specific embodiment, the angle of the beveled face relative to the plane of insertion 123 is about 35°. Inclusion of such a beveled face in sensor port 100 can limit and/or prevent ingress of one or more external contaminants into the internal area of sensor port 101.

Additional disclosure and examples of contamination resistant sensor ports are provided in U.S. patent application Ser. No. 12/539,217, filed Aug. 11, 2009, and entitled "Analyte Sensor Ports," the disclosure of which is incorporated by reference herein.

In some embodiments, the sensor ports described herein can be configured to work with (e.g., engage with or operate in connection with) additional mechanisms and/or devices designed to limit and/or prevent contamination of the internal areas of the sensor ports themselves or the internal areas of the electrical devices into which the sensor ports can be integrated. For example, mechanisms, devices and methods of protecting sensor port openings are described in U.S. Patent Application Publication No. 2008/0234559, and U.S. Patent Application Publication No. 2008/0119709, the disclosure of each of which is incorporated by reference herein. Sensor ports according to the present disclosure can also be configured to be replaceable and/or disposable, and/or configured so as to limit and/or prevent contamination of an electrical device in which the sensor port is integrated. Additional description is provided, for example, in U.S. patent application Ser. No. 12/495,662, filed Jun. 30, 2009, entitled "Strip Connectors for Measurement Devices," the disclosure of which is incorporated by reference herein.

Fluid-Wicking Sensor Port Interface

In some embodiments, a sensor port as disclosed herein is optionally configured as a fluid-wicking sensor port interface. In some such embodiments, the sensor port is configured to include one or more hydrophilic and/or absorptive materials positioned in proximity to an opening in the sensor port, wherein the opening is configured to receive an analyte sensor, e.g., an analyte test strip. The hydrophilic and/or absorptive materials may be positioned, for example, surrounding or substantially surrounding the opening in the sensor port. In some embodiments, the one or more hydrophilic and/or absorptive materials are positioned above and/or below the sensor port opening. In other embodiments, the one or more hydrophilic and/or absorptive materials are positioned to the left and/or right of the sensor port opening. In some embodiments, the one or more hydrophilic and/or absorptive materials define at least a portion of the opening in the sensor port.

In certain embodiments, one or more, e.g., 2, rotating absorptive guards are positioned in relation to the sensor port opening (e.g., directly above and/or below the sensor port opening) such that during insertion of an analyte sensor, e.g., an analyte test strip, the absorptive guards each rotate while making contact with the analyte sensor. The rotating absorptive guards can be configured to engage the sensor port housing or the analyte meter housing, e.g., by engaging one or more shafts positioned on the sensor port housing or the analyte meter housing. The rotating action of the absorptive guards, e.g., about the one or more shafts, can mitigate added resistance which may be experienced by the user as a result of contact between the analyte sensor and the one or more absorptive guards as the user inserts the analyte sensor into the sensor port. In some embodiments, once the analyte sensor is inserted, the absorptive guards form a barrier at the point or points of contact with the analyte sensor such that unwanted or excess fluid is prevented or at least substantially inhibited from entering the sensor port opening. The one or more rotating absorptive guards may be disposable and/or replaceable. For example, the absorptive guards may be configured such that they can be easily removed from the sensor port for cleaning, disposal and/or replacement. In one embodiment, the rotating absorptive guards have a substantially cylindrical shape, however, an absorptive guard having any suitable shape may be utilized.

In some embodiments, a sensor port configured as a fluid-wicking sensor port interface includes one or more paths and/or channels sized for capillary action which are positioned relative to the opening in the sensor port such that they facilitate the wicking of fluid away from the opening in the sensor port. These one or more paths and/or channels may include a hydrophilic and/or absorptive material and/or coating. In some embodiments, the one or more paths and/or channels include a mechanism by which air, when displaced by fluid, can escape the one/or more paths and/or channels. For example, in one embodiment, the one/or more paths and/or channels connect to one/or more additional paths and/or channels which provide an opening to the external environment of an analyte meter which incorporates a sensor port as described herein. In some embodiments, the one or more paths and/or channels are positioned to facilitate flow of fluid in the general direction of a gravitational force applied during the insertion process. In some embodiments, the one or more paths and/or channels terminate in a reservoir positioned, for example, in the housing of the sensor port or the housing of an analyte meter configured to include the sensor port.

In some embodiments, a fluid-wicking sensor port interface is configured to provide one or more alternative paths for a fluid which are more energetically favorable than a path which would bring the fluid into the internal environment of the sensor port through the opening in the sensor port.

In some embodiments, the fluid-wicking portion of a fluid-wicking sensor port interface according to the present disclosure is separately disposable and/or replaceable. In other embodiments, the fluid-wicking portion is physically integrated with the sensor port housing and/or the housing of an analyte meter which includes a sensor port according to the present disclosure such that the fluid-wicking portion is not configured to be separately disposable and/or replaceable.

In additional embodiments, the hydrophilic and/or absorptive material and/or coating may include a material which changes color when contacted with a fluid. This may provide, for example, an indication that excess fluid was subject to wicking action by the hydrophilic and/or absorptive material and/or coating.

While the fluid-wicking sensor port interface has been described above with reference to the sensor ports disclosed herein, it should be noted that the features of the fluid-wicking sensor port interface may provide similar effects when used in connection with other openings in analyte meters, or openings in other devices. For example, the features of the fluid-wicking sensor port interface may be used to prevent or inhibit fluid ingress into a battery compartment or communication port of an analyte meter.

Protective Protrusion

In some embodiments, a sensor port as disclosed herein includes an optional protective protrusion configured to protect a sensor port contact of the sensor port. The protective protrusion may be formed from the same material used to form the housing of the sensor port, and, in some embodiments, may be a portion of the housing itself. Alternatively, the protective protrusion may be formed from a suitable metal, polymer, etc. and attached to and/or positioned in the sensor port housing.

Figure 7B:
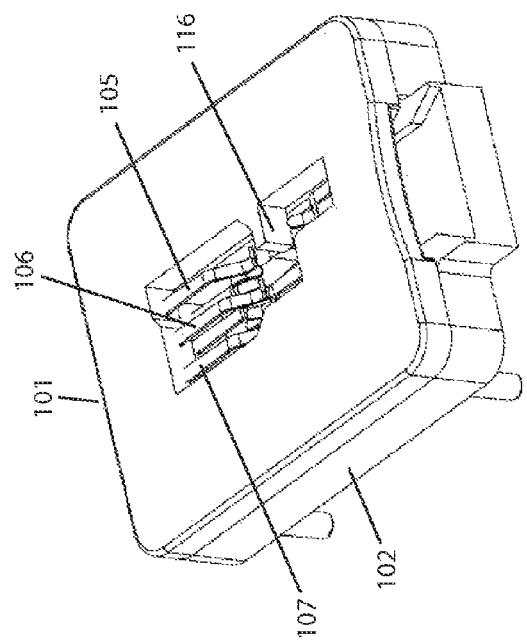
FIG. 7A and FIG. 7B show top and perspective views respectively of an embodiment of a sensor port according to the present disclosure including an optional protective protrusion for a sensor port contact.
Figure 7A:
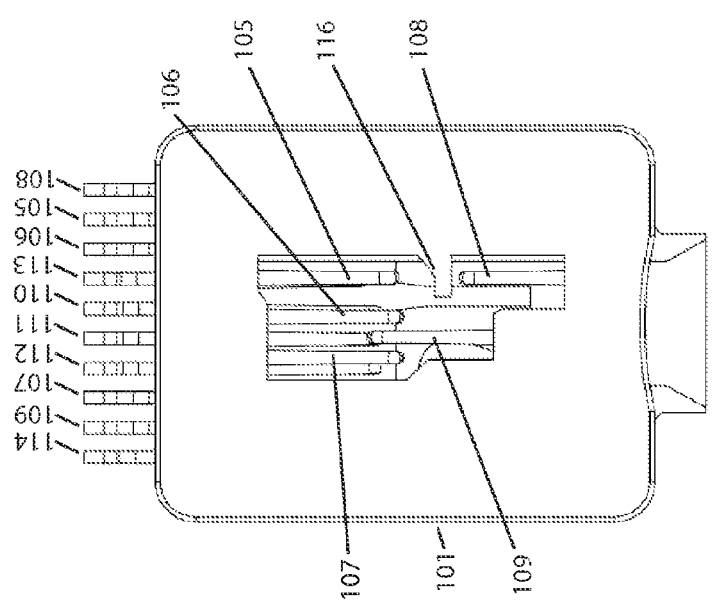
Figure 8A:
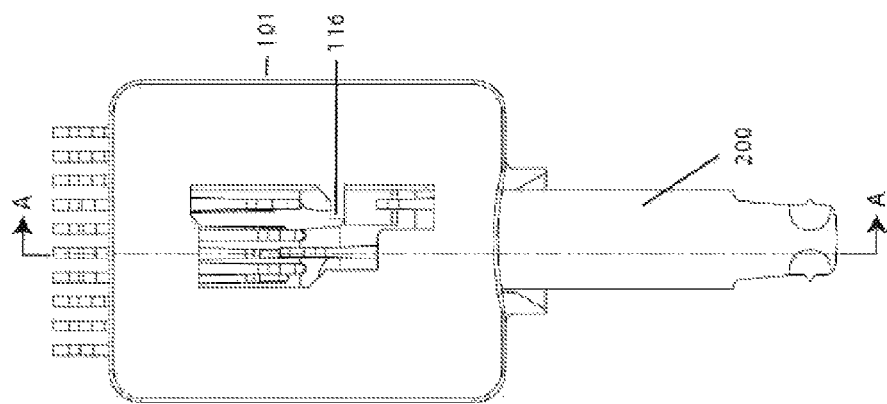
FIG. 8A, FIG. 8B and FIG. 8C show a top view, a cross-sectional view, and an expanded cross-sectional view respectively of an embodiment of a sensor port according to the present disclosure, including an optional protective protrusion for a sensor port contact and a damaged analyte sensor inserted into the sensor port, wherein the damaged analyte sensor is prevented from contacting and damaging a sensor port contact.
Figure 8B:
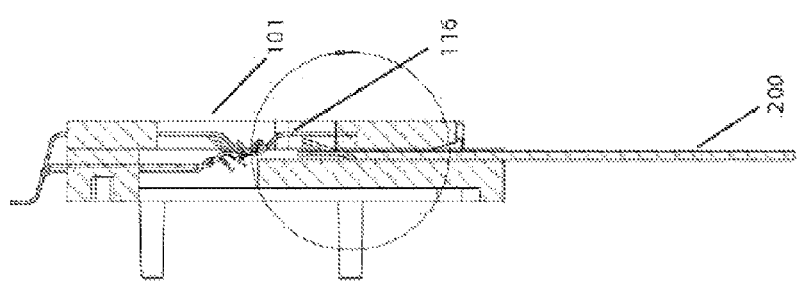
Figure 8C:
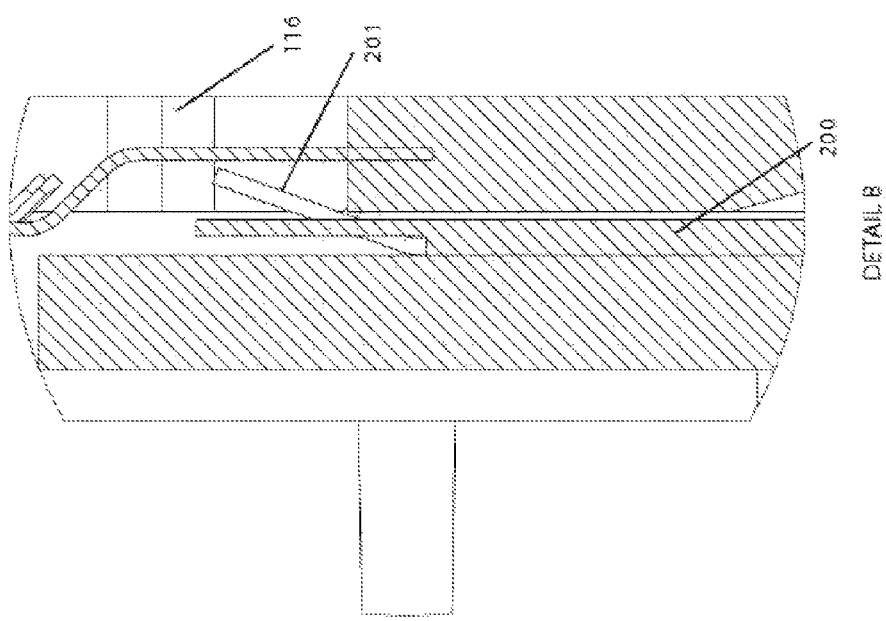
Figure 9B:
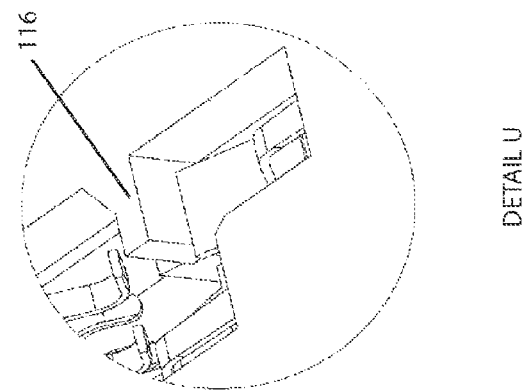
FIG. 9A and FIG. 9B show a top perspective view and an expanded detail view respectively of the sensor port shown in FIG. 8A, FIG. 8B and FIG. 8C.
Figure 9A:
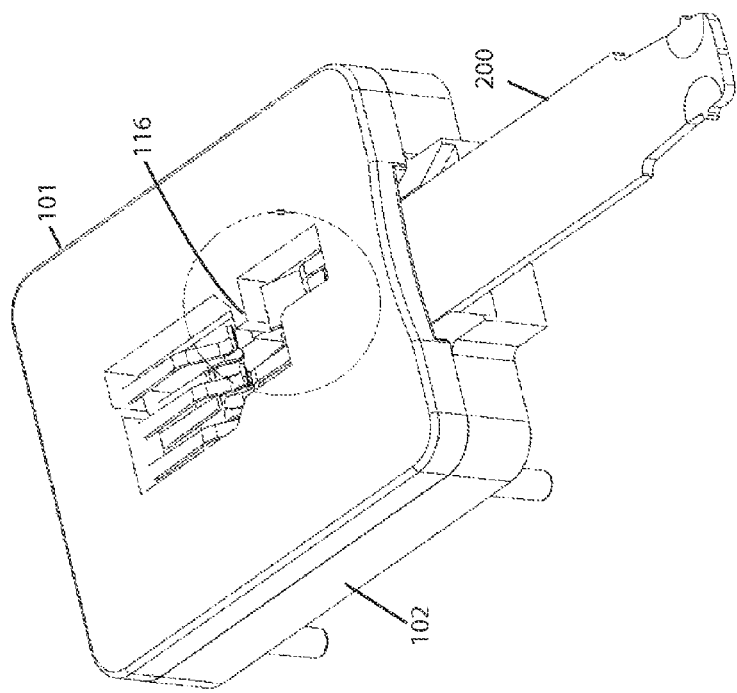

With reference to FIGS. 7A, 7B, 8A, 8B, 8C, 9A and 9B, a sensor port 101 is provided, which includes a protective protrusion 116. In some embodiments, protective protrusion 116 is formed from the same material used to form housing 102 of sensor port 101. Alternatively, protective protrusion 116 may be made from a material other than that used to form sensor port housing 102. As shown in FIG. 7A, in some embodiments the protective protrusion 116 extends from the side wall of the top portion 103 of sensor port housing 102 into the interior space of sensor port 101. Protective protrusion 116 is positioned relative to sensor port contact 105 such that sensor port contact 105 is protected from an improperly inserted and/or damaged analyte sensor, e.g., as shown in FIGS. 8A-8C. Improper insertion and/or insertion of a damaged analyte sensor can, in some cases, damage a sensor port contact, such as sensor port contact 105, by compressing or otherwise deforming the electrode contact from its intended positioning. For example, during the handling of an analyte sensor 200 a proximal portion of substrate 205 on which electrode contact 201 is positioned may become bent, e.g., as shown in FIG. 8C. If a user were to insert such a damaged analyte sensor, sensor port contact 105 could be compressed or otherwise deformed by contact with the damaged analyte sensor. Protective protrusion 116 is configured to prevent such contact between a damaged analyte sensor and a sensor port contact.

Illuminated Sensor Port

In one embodiment, analyte meter 100 and/or sensor port 101 includes an optional illumination device (not shown), e.g., a light emitting diode (LED), which may be configured to illuminate the sensor port 101 during the analyte sensor insertion process to assist the user in accurately inserting an analyte sensor into sensor port 101. Additional information regarding illuminated sensor ports and methods of powering same can be found in U.S. Patent Application Publication No. 2005/0009126, the disclosure of which is incorporated by reference herein.

Latch or Securement Mechanism

In a further embodiment of the present disclosure, the sensor port 101 may be configured with a physical latch or securement mechanism such that when an analyte sensor is inserted into the sensor port 101, the analyte sensor is retained in the received position within the sensor port 101 until the sample analysis is completed. Examples of such physical latches or securement mechanisms may include a uni-directionally biased anchor mechanism, or a pressure application mechanism to retain the analyte sensor in place by applying pressure on one or more surfaces of the analyte sensor within the sensor port 101. Additional information is provided in U.S. Patent Application Publication No. 2008/0119709, the disclosure of which is incorporated by reference herein.

Analyte Sensors

As discussed previously herein, in some embodiments, the disclosed sensor ports are configured such that they are capable of receiving at least two different types of analyte sensors, e.g., a first type having an opposing electrode configuration and a second type having a co-planar electrode configuration. Examples of these analyte sensor types are now described in greater detail with reference to the figures. In FIGS. 14A, 14B, and 14D, analyte sensors 200 having an opposing electrode configuration are depicted which include a first substrate 205, a second substrate 206, and a spacer (not shown) separating first substrate 205 and second substrate 206. Analyte sensors 200 also include a working electrode, a reference and/or counter electrode, a first fill-indicator electrode and a second fill-indicator electrode. As used herein, the term "reference and/or counter electrode" refers to an electrode that functions as a reference electrode, a counter electrode or both a reference and counter electrode. In the embodiment depicted in FIGS. 14A, 14B and 14D, the working electrode includes electrode contact 201 for providing an electrical connection between the working electrode and a sensor port contact of sensor port 101, the reference and/or counter electrode includes electrode contact 203 for providing an electrical connection between the reference and/or counter electrode and a sensor port contact of sensor port 101, and the first and second fill-indicator electrodes include electrode contacts 202 and 204 respectively for providing an electrical connection between the fill-indicator electrodes and sensor port contacts of sensor port 101. As shown in FIGS. 14A, 14B and 14D, analyte sensors 200 include a proximal end 207 for insertion into a sensor port 101 and a distal end 208 for receiving a liquid sample.

In FIGS. 14C and 14E, analyte sensors 300 having a co-planar electrode configuration are depicted which include a first substrate 304 with working, reference and/or counter, and fill indicator electrodes position thereon. The working electrode includes electrode contact 303 for providing an electrical connection between the working electrode and a sensor port contact of sensor port 101, the reference and/or counter electrode includes electrode contact 301 for providing an electrical connection between the reference and/or counter electrode and a sensor port contact of sensor port 101, and the fill-indicator electrode includes electrode contact 302 for providing an electrical connection between the fill-indicator electrode and a sensor port contact of sensor port 101. As shown in FIGS. 14C and 14E, analyte sensors 300 include a proximal end 305 for insertion into a sensor port 101 and a distal end 306 for receiving a liquid sample. Analyte sensor 300 also includes at least a second substrate 307 positioned over a portion of first substrate 304, such that electrode contacts 301, 302, and 303 are exposed at the proximal end of the sensor. One or more spacer layers may also be included in analyte sensor 300.

In certain embodiments, an analyte sensor suitable for use in the sensor ports disclosed herein has a generally rectangular shape, i.e., the sensor's length is greater than its width, although other shapes are possible as well. In one embodiment, the analyte sensor is in the form of a strip.

Analyte sensors suitable for use with the sensor ports described herein can include a plurality of electrodes, e.g., 2, 3, 4 or more electrodes.

In addition to the embodiments specifically disclosed herein, the sensor ports and analyte meters of the present disclosure can be configured to work with a wide variety of analyte sensors, e.g., those disclosed in U.S. patent application Ser. No. 11/461,725, filed Aug. 1, 2006; U.S. Patent Application Publication No. 2007/0095661; U.S. Patent Application Publication No. 2006/0091006; U.S. Patent Application Publication No. 2006/0025662; U.S. Patent Application Publication No. 2008/0267823; U.S. Patent Application Publication No. 2007/0108048; U.S. Patent Application Publication No. 2008/0102441; U.S. Patent Application Publication No. 2008/0066305; U.S. Patent Application Publication No. 2007/0199818; U.S. Patent Application Publication No. 2008/0148873; U.S. Patent Application Publication No. 2007/0068807; U.S. Pat. Nos. 6,616,819; 6,143,164; and 6,592,745; the disclosures of each of which are incorporated by reference herein. Additional analyte sensors are described in U.S. patent application Ser. No. 12/102,374, filed Apr. 14, 2008, and U.S. Patent Application Publication No. 2009/0095625, the disclosures of each of which are incorporated by reference herein.

Integration with Analyte Meters and/or Analyte Monitoring Systems

The present disclosure provides analyte meters which include one of the sensor ports described herein. The analyte meters are configured to process a signal received from an analyte sensor inserted into the sensor port and determine the concentration of an analyte based on the received signal.

The analyte meters may be small portable devices designed to be palm-sized and/or adapted to fit into, for example, a pocket or purse of a patient. The analyte meter may be incorporated into a personal electronic device, such as a mobile phone (e.g., iPhone®) or personal digital assistant (PDA).

In some embodiments, the analyte meter may be a larger unit for home use and designed to sit on a shelf or nightstand. In yet other embodiments, the analyte meters may be designed for use in a hospital or doctor's office.

Additional description of analyte meters and/or analyte monitoring systems and features thereof which may be utilized in connection with a sensor port as described herein can be found, for example, in U.S. Pat. Nos. 6,526,298 and 7,041,468, the disclosure of each of which is incorporated by reference herein.

Figure 13:
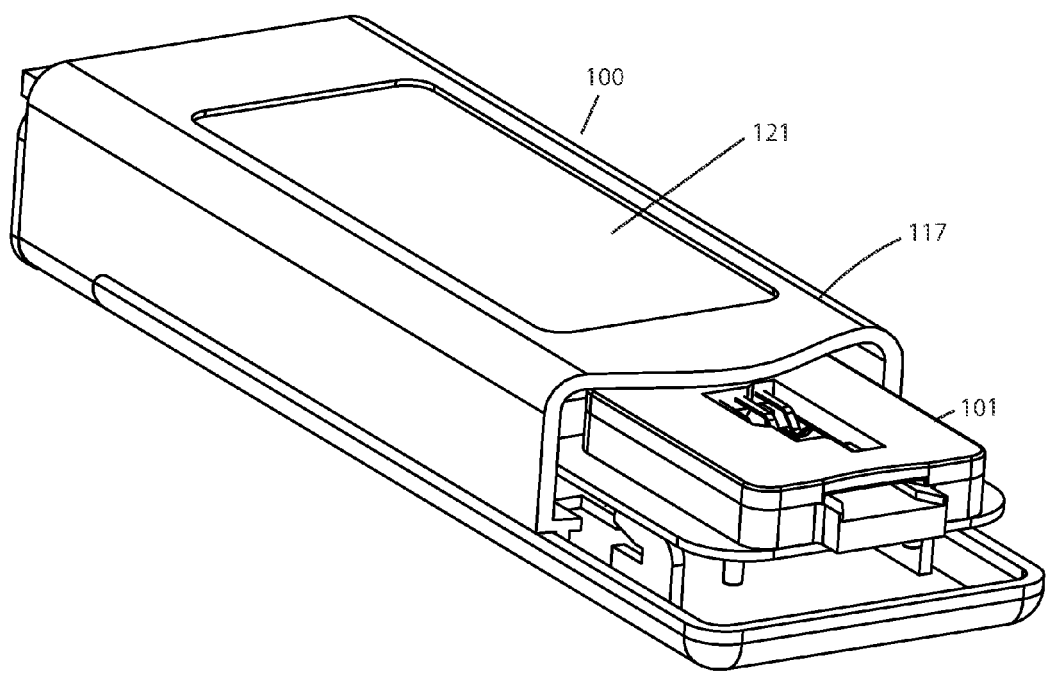
FIG. 13 shows an embodiment of an analyte meter accordingly to the present disclosure which includes a sensor port according to the present disclosure; a cut-out view is shown such that the sensor port is visible.

In one embodiment, as shown in FIG. 13, an analyte meter 100 is provided, which includes a meter housing 117 and a sensor port 101 coupled to the housing, wherein the sensor port is configured to receive a first analyte sensor, e.g., an analyte sensor 200, having an opposing electrode configuration and a second analyte sensor, e.g., an analyte sensor 300, having a co-planar electrode configuration. The analyte meter 100 also includes a processing unit 600 (not shown in FIG. 13) coupled to the housing, wherein the processing unit is configured to receive from the first and second analyte sensors one or more signals indicative of an analyte concentration in a sample and thereby determine the analyte concentration in the sample. The processing unit 600 is depicted as a system component in FIG. 16. For reference, the terms "processing unit," "processor," and "control unit" are used interchangeably herein.

As indicated above, in certain embodiments, sensor ports according to the present disclosure are integrated with analyte meters and/or analyte monitoring systems. For example, a sensor port according to the present disclosure may be integrated with a FreeStyle® blood glucose monitoring meter or a Precision® brand blood monitoring meter capable of monitoring glucose and ketones, or other such analytes. In addition, the disclosed sensor ports may find use in meters designed for use in a hospital or similar clinic environment where a single meter may be used for a plurality of patients. Such systems include, but are not limited to, Precision PCx® meters, FreeStyle Connect™ meters and Precision Xceed Pro™ meters manufactured by Abbott Diabetes Care Inc. (Alameda, Calif.).

In certain embodiments, the sensor ports may be integrated with an analyte monitoring system including an implanted or partially implanted analyte sensor, e.g., a system including an implanted or partially implanted glucose sensor (e.g., a continuous glucose sensor). A system including an implanted or partially implanted glucose sensor may include a component that receives analyte data from the implanted or partially implanted glucose sensor, which component may be configured to communicate analyte results to the user, e.g., audibly or visually by way of a display, or by communicating with a stand-alone analyte meter or other portable processing device (e.g., a mobile phone) configured to display analyte results. The analyte monitoring system receiver may include a conventional blood glucose meter configured to incorporate a sensor port 101 as described herein for accepting a glucose sensor, e.g., a glucose test strip. The conventional meter and test strip may be used to calibrate the system, e.g., using one point calibration or other calibration protocol. For additional information, see U.S. Pat. No. 6,175,752, the disclosure of which is incorporated by reference herein. In some embodiments, the receiver and/or meter may be configured to communicate with the implanted or partially implanted analyte sensor via RFID and provide for intermittent or periodic interrogation of the implanted analyte sensor.

It should be understood that description of sensor ports in connection with analyte meters includes stand-alone meters, as well those operably connected to, e.g., integrated with, analyte monitoring systems including implanted or partially implanted analyte sensors (e.g., continuous analyte monitoring systems). Exemplary sensors and meters and continuous analyte monitoring systems (sometimes referred to as in vivo systems) that may be utilized in connection with the disclosed sensor ports include sensors and meters such as those described in U.S. Pat. Nos. 7,041,468; 5,356,786; 6,175,752; 6,560,471; 5,262,035; 6,881,551; 6,121,009; 7,167,818; 6,270,455; 6,161,095; 5,918,603; 6,144,837; 5,601,435; 5,822,715; 5,899,855; 6,071,391; 6,120,676; 6,143,164; 6,299,757; 6,338,790; 6,377,894; 6,600,997; 6,773,671; 6,514,460; 6,592,745; 5,628,890; 5,820,551; 6,736,957; 4,545,382; 4,711,245; 5,509,410; 6,540,891; 6,730,200; 6,764,581; 6,299,757; 6,461,496; 6,503,381; 6,591,125; 6,616,819; 6,618,934; 6,676,816; 6,749,740; 6,893,545; 6,942,518; 6,514,718; 5,264,014; 5,262,305; 5,320,715; 5,593,852; 6,746,582; 6,284,478; 7,299,082; U.S. Patent Application No. 61/149,639, entitled "Compact On-Body Physiological Monitoring Device and Methods Thereof", U.S. patent application Ser. No. 11/461,725, filed Aug. 1, 2006, entitled "Analyte Sensors and Methods"; U.S. patent application Ser. No. 12/495,709, filed Jun. 30, 2009, entitled "Extruded Electrode Structures and Methods of Using Same"; U.S. Patent Application Publication No. 2004/0186365; U.S. Patent Application Publication No. 2007/0095661; U.S. Patent Application Publication No. 2006/0091006; U.S. Patent Application Publication No. 2006/0025662; U.S. Patent Application Publication No. 2008/0267823; U.S. Patent Application Publication No. 2007/0108048; U.S. Patent Application Publication No. 2008/0102441; U.S. Patent Application Publication No. 2008/0066305; U.S. Patent Application Publication No. 2007/0199818; U.S. Patent Application Publication No. 2008/0148873; and U.S. Patent Application Publication No. 2007/0068807; the disclosures of each which are incorporated by reference herein.

Processing Unit

Analyte meter 100 includes a processing unit, e.g., a processing unit 600 coupled to housing 117, wherein the processing unit is configured to receive from an analyte sensor one or more signals indicative of an analyte concentration in a sample and thereby determine the analyte concentration in the sample.

Details relating to the receipt of an analyte signal from an analyte sensor and the determination of a concentration of analyte are described, for example, in U.S. Pat. Nos. 7,041,468; 5,356,786; 6,175,752; 6,560,471; 5,262,035; 6,881,551; 6,121,009; 7,167,818; 6,270,455; 6,161,095; 5,918,603; 6,144,837; 5,601,435; 5,822,715; 5,899,855; 6,071,391; 6,120,676; 6,143,164; 6,299,757; 6,338,790; 6,377,894; 6,600,997; 6,773,671; 6,514,460; 6,592,745; 5,628,890; 5,820,551; 6,736,957; 4,545,382; 4,711,245; 5,509,410; 6,540,891; 6,730,200; 6,764,581; 6,299,757; 6,461,496; 6,503,381; 6,591,125; 6,616,819; 6,618,934; 6,676,816; 6,749,740; 6,893,545; 6,942,518; 6,514,718; 5,264,014; 5,262,305; 5,320,715; 5,593,852; 6,746,582; 6,284,478; 7,299,082; U.S. patent application Ser. No. 10/745,878 filed Dec. 26, 2003 entitled "Continuous Glucose Monitoring System and Methods of Use"; U.S. Patent Application No. 61/149,639 entitled "Compact On-Body Physiological Monitoring Device and Methods Thereof", U.S. patent application Ser. No. 11/461,725, filed Aug. 1, 2006; U.S. Patent Application Publication No. 2007/0095661; U.S. Patent Application Publication No. 2006/0091006; U.S. Patent Application Publication No. 2006/0025662; U.S. Patent Application Publication No. 2008/0267823; U.S. Patent Application Publication No. 2007/0108048; U.S. Patent Application Publication No. 2008/0102441; U.S. Patent Application Publication No. 2008/0066305; U.S. Patent Application Publication No. 2007/0199818; U.S. Patent Application Publication No. 2008/0148873; and U.S. Patent Application Publication No. 2007/0068807; the disclosures of each which are incorporated by reference herein.

In some embodiments, the analyte meter 100 includes a data storage unit, e.g., a data storage unit 601 (not shown in FIG. 13) operably connected to the processing unit, e.g., as described in U.S. patent application Ser. No. 11/396,182, filed Mar. 31, 2006, titled "Analyte Monitoring Devices and Methods Therefor," the disclosure of which is incorporated by reference herein. Data storage unit 601 is depicted as a system component along with processing unit 600 in FIG. 16.

Dosage Calculation Function

In some embodiments, the processing unit is configured to perform medication dosage calculation functions, such as a single-dose calculation function for injection of rapid acting insulin and/or long acting insulin. Analyte meters which include medication dosage calculation functions and methods of performing the dosage calculation functions are described, for example, in U.S. patent application Ser. No. 11/396,182, filed Mar. 31, 2006, entitled "Analyte Monitoring Devices and Methods Therefor," in the U.S. patent application entitled "Multi-Function Analyte Test Device and Methods Therefor," listing Mark K. Sloan as the first named inventor and designated by, and in the U.S. patent application entitled "Multi-Function Analyte Test Device and Methods Therefor," listing Mark K. Sloan as the first named inventor and designated by, the disclosure of each of which is incorporated by reference herein.

In one embodiment, the processing unit is configured to perform a bolus calculation function. For example, the processing unit may be configured to determine a bolus dosage, e.g., an insulin bolus dosage, based on the signal received from an analyte sensor.

In one embodiment the processing unit is configured to perform an algorithm to determine a medication dosage based on a determined concentration of analyte.

The analyte meter 100 may be configured to automatically enter into a medication dosage calculation mode to, for example, calculate and/or select a medication dosage amount based on information stored in the analyte meter 100 (such as the patient's insulin sensitivity, for example), and/or prompt the patient to provide additional information, such as the amount of carbohydrate to be ingested by the patient for determination of, for example, a carbohydrate bolus dosage determination. The patient may operate an input unit (described in greater detail below) to provide the appropriate information.

In another embodiment, the analyte meter 100 may be configured to prompt the patient to select whether to retrieve a predetermined or preprogrammed medication dosage amount such as, for example, a correction bolus or a carbohydrate bolus, following the display of the determined analyte concentration from the analyte sensor. In this manner, in one embodiment of the present disclosure, analyte meter 100 may be configured to automatically prompt the user or patient to select whether a medication dosage determination is desired following analyte testing using an analyte sensor.

In one embodiment of the present disclosure, the analyte meter 100 may be configured to execute different types of medication dosage calculations based on the patient specified parameters. For example, the analyte meter 100 may be configured to perform a carbohydrate bolus determination when the analyte sensor sample analysis is performed within a predetermined time period of a meal event. For example, the analyte meter 100 may be programmed by the patient to automatically select the carbohydrate bolus determination if the analyte sensor fluid sample analysis is performed within one hour prior to a meal time (which may be programmed into the analyte meter 100).

In some embodiments, a processing unit of an analyte meter or another portable electronic processing device is configured to prompt a user to enter the delivery time of a medication dosage, e.g., a medication dosage calculated by the processing unit. For example, following a bolus dosage calculation, e.g., an insulin bolus dosage calculation, the processing unit may automatically prompt the user, e.g., using the display unit, to enter the time at which the calculated bolus dosage was administered.

In some embodiments, the processing unit may be further configured to automatically prompt the user, following entry of the administration time, to enter the time at which a subsequent meal is started. Such information may then be utilized by the processing unit or an external processing device to optimize future medication dosage calculations.

Bolus Calculator Safety Features

In some embodiments, a processor of an analyte meter device or another portable electronic processing device is configured to provide one or more bolus calculator safety features. As discussed herein, an analyte meter according to the present disclosure may be configured to communicate with and receive analyte measurements from an external analyte monitoring device and/or system, e.g., a continuous glucose monitoring (CGM) device and/or system or a "glucose on demand" (GoD) monitoring device and/or system.

Where an analyte meter is configured to communicate with and receive analyte measurements from a CGM device and/or system (e.g., a device and/or system including an implanted or partially implanted analyte sensor configured to automatically measure glucose levels at predetermined intervals), the processor may be configured to automatically (or in response to a user input) initiate a process to specifically monitor a user's glucose response to a bolus dose of insulin. For example, in some embodiments, the processor is configured to provide an expected glucose profile over a period of time using a physiological model associated with one or more of the user's insulin action time, glucose trajectory, meal input data, insulin input data, exercise data, health data, and time-of-day. The process may provide a "minimum" acceptable profile where the predicted glucose has a minimum value at a predetermined low glucose safety limit. The process may also provide a "maximum" acceptable profile where the predicted glucose has a maximum value at a predetermined high glucose safety limit.

These profiles may be determined in a number of ways. For example, they may be determined by increasing and decreasing carbohydrate intake until the point that the profile limits are reached. Alternatively, meal timing or one or more of the other physiological model parameters may be varied.

The processor may then monitor using the CGM device and/or system received real-time data to determine if it falls within the minimum and maximum profiles indicated at that point in time. If a predetermined number of glucose readings (e.g., one or more) fall outside the profile range, then the processor can be configured to communicate an alarm and/or alert to the user and indicated that the glucose reading was lower or higher than expected. In some embodiments, the processing device may then communicate to the user a recommended course of action.

Where an analyte meter is configured to communicate with and receive analyte measurements from a GoD device and/or system (e.g., a glucose monitoring device and/or system including an implanted or partially implanted analyte sensor and requiring user initiation to receive a glucose reading), the processor may be configured to prompt the user to obtain a glucose measurement from the GoD device and/or system at predetermined time points relative to a bolus administration, e.g., at 20 min and 45 min following the bolus administration. These measurements may then be compared to a predetermined glucose profile or profiles. If a predetermined number of glucose readings (e.g., one or more) fall outside the profile range, then the processor can be configured to communicate an alarm and/or alert to the user and indicated that the glucose reading was lower or higher than expected. In some embodiments, the processing device may then communicate to the user a recommended course of action.

Additional description of glucose-on-demand devices and/or systems can be found in US Patent Application Publication Nos. 2008/0319296, 2009/0054749, 2009/0294277, 2008/0319295; in U.S. patent application Ser. No. 12/393,921, filed Feb. 26, 2009, and entitled "Self-Powered Analyte Sensor"; and Ser. No. 12/625,524, filed Nov. 24, 2009, and entitled "RF Tag on Test Strips, Test Strip Vials and Boxes"; and in U.S. Provisional Patent Application Nos. 61/247,519, filed Sep. 30, 2009, and entitled "Electromagnetically-Coupled On-Body Analyte Sensor and System"; 61/155,889, filed on Feb. 26, 2009, and entitled "Analyte Measurement Sensors And Methods For Fabricating The Same"; 61/238,581, filed on Aug. 31, 2009, and entitled "Analyte Monitoring System with Electrochemical Sensor"; 61/163,006, filed on Mar. 24, 2009, and entitled "Methods Of Treatment And Monitoring Systems For Same"; 61/247,508, filed on Sep. 30, 2009, and entitled "Methods and Systems for Calibrating On-Demand Analyte Measurement Device"; 61/149,639, filed on Feb. 2, 2009, and entitled "Compact On-Body Physiological Monitoring Devices and Methods Thereof"; and 61/291,326, filed on Dec. 30, 2009, and entitled "Ultra High Frequency (UHF) Loop Antenna for Passive Glucose Sensor and Reader"; the disclosures of each which are incorporated by reference herein.

Bolus calculator safety features may also be incorporated into analyte meters which are not in communication with external analyte monitoring devices and/or systems, but which are instead configured for self monitoring of blood glucose (SMBG). For example, such an analyte meter may include a processor configured to issue an alarm, alert or reminder to a user to perform an additional glucose reading at a predetermined time, e.g. 5 min, following an initial glucose reading and an associated bolus calculation. This allows the processor to determine a rate factor based on the two glucose values separated in time. This rate factor may then be taken into account by the processor in performing a new bolus calculation or providing an adjustment to a previous bolus calculation. In some embodiments, the processor may determine that an initial bolus which was fully delivered was too high and that corrective action, e.g., ingestion of carbohydrate, should be taken to avoid overdelivery.

In some embodiments, a portion (e.g., 70%) of the calculated bolus dose is delivered or recommended for delivery based on an initial glucose reading. Subsequently, some, all or none of the remaining portion of the calculated bolus may be delivered or recommended for delivery based on a second calculated bolus taking into account the glucose rate determined following the second glucose reading.

Communication Unit

In some embodiments, an analyte meter 100 as described herein includes an optional communication unit 602 (not shown in FIG. 13), e.g., a receiver and/or transmitter for communicating with a network and/or another device, e.g., a medication delivery device and/or a patient monitoring device, e.g., a continuous glucose monitoring device. The communication unit may be configured for one or two way communication of data, software, etc. between the analyte meter 100 and an external device, system, etc. In some embodiments, the communication unit is configured for communication with a health management system, such as the CoPilot™ system available from Abbott Diabetes Care Inc., Alameda, Calif. In one embodiment, the communication unit is coupled to the housing 117 of analyte meter 100 and is in communication with the processing unit. Communication unit 602 is depicted as a system component in FIG. 16.

The communication unit can be configured for wired or wireless communication, including, but not limited to, radio frequency (RF) communication (e.g., Radio-Frequency Identification (RFID), Zigbee communication protocols, WiFi, infrared, wireless Universal Serial Bus (USB), Ultra Wide Band (UWB), Bluetooth® communication protocols, and cellular communication, such as code division multiple access (CDMA) or Global System for Mobile communications (GSM). In one embodiment, analyte meter 100 includes a wireless communication unit, wherein the wireless communication unit is configured for bi-directional radio frequency (RF) communication with other devices to transmit and/or receive data to and from the analyte meter 100.

In one embodiment, the communication unit is configured to include one or more communication ports, e.g., physical ports or interfaces such as a USB port, an RS-232 port, or any other suitable electrical connection port to allow data communication between the analyte meter 100 and other external devices such as a computer terminal (for example, at a physician's office or in hospital environment), an external medical device, such as an infusion device or including an insulin delivery device, or other devices that are configured for similar complementary data communication.

In one embodiment, the communication unit is configured for infrared communication, Bluetooth® communication, or any other suitable wireless communication protocol to enable the analyte meter 100 to communicate with other devices such as infusion devices, analyte monitoring devices, computer terminals and/or networks, communication enabled mobile telephones, personal digital assistants, or any other communication devices which the patient or user of the analyte meter may use in conjunction therewith, in managing the treatment of a health condition, such as diabetes.

In one embodiment, the communication unit is configured to provide a connection for data transfer utilizing Internet Protocol (IP) through a cell phone network, Short Message Service (SMS), wireless connection to a personal computer (PC) on a Local Area Network (LAN) which is connected to the internet, or WiFi connection to the internet at a WiFi hotspot.

In one embodiment, the analyte meter is configured to wirelessly communicate with a server device via the communication unit, e.g., using a common standard such as 802.11 or Bluetooth® RF protocol, or an IrDA infrared protocol. The server device could be another portable device, such as a smart phone, Personal Digital Assistant (PDA) or notebook computer; or a larger device such as a desktop computer, appliance, etc. In some embodiments, the server device has a display, such as a liquid crystal display (LCD), as well as an input device, such as buttons, a keyboard, mouse or touchscreen. With such an arrangement, the user can control the meter indirectly by interacting with the user interface(s) of the server device, which in turn interacts with the meter across a wireless link.

In some embodiments, the communication unit is configured to automatically or semi-automatically communicate data stored in the analyte meter, e.g., in the optional data storage unit, with a network or server device using one or more of the communication protocols and/or mechanisms described above.

Figure 16:
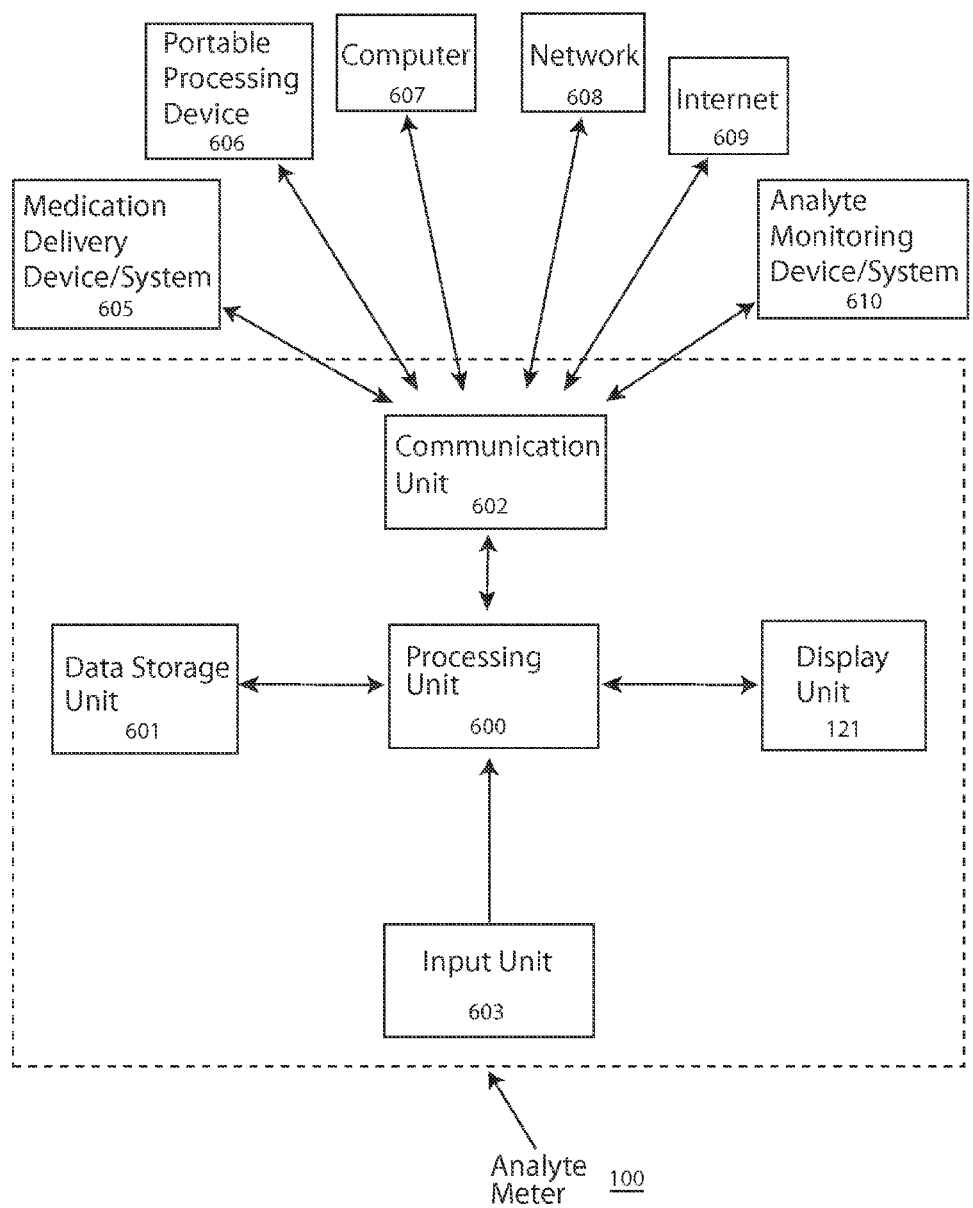
FIG. 16 provides a diagram showing data flow within a health management system, e.g., a diabetes management system, including an embodiment of an analyte meter according to the present disclosure.
Figure 17:
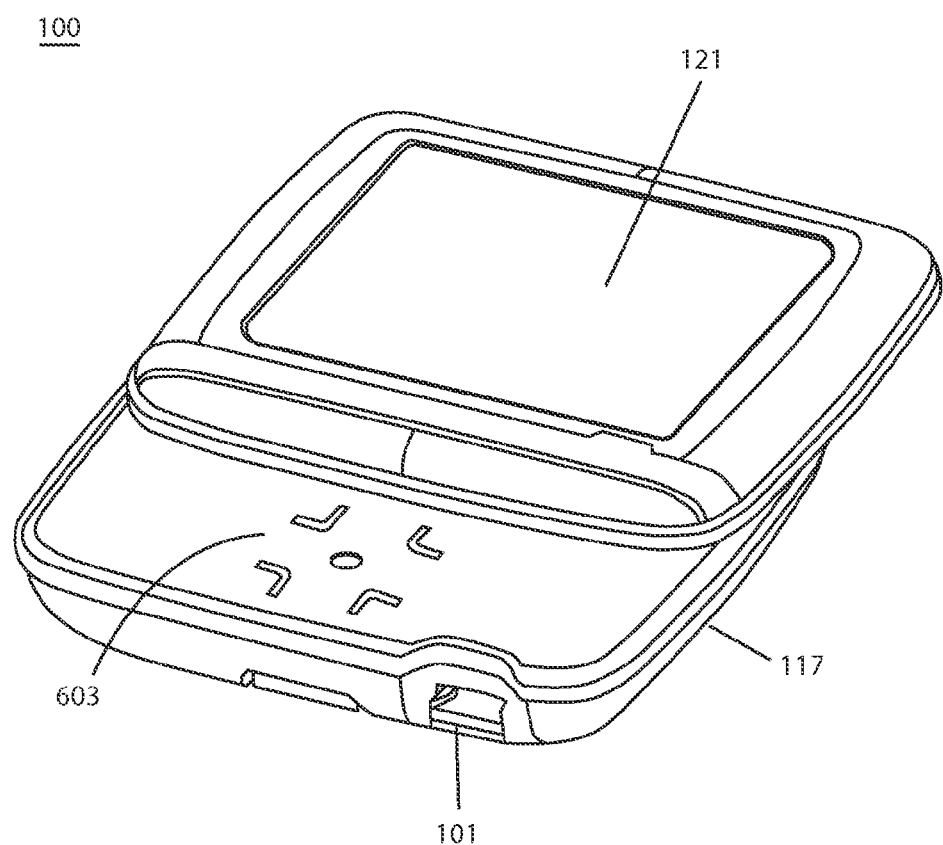
FIG. 17 shows a perspective view of an additional embodiment of an analyte meter accordingly to the present disclosure which includes a sensor port according to the present disclosure. The analyte meter is depicted in a "slider" configuration in which a portion of the meter housing including a display can be slid to an open or closed position to respectively expose or cover a portion of the meter housing including an input unit.
Figure 18:
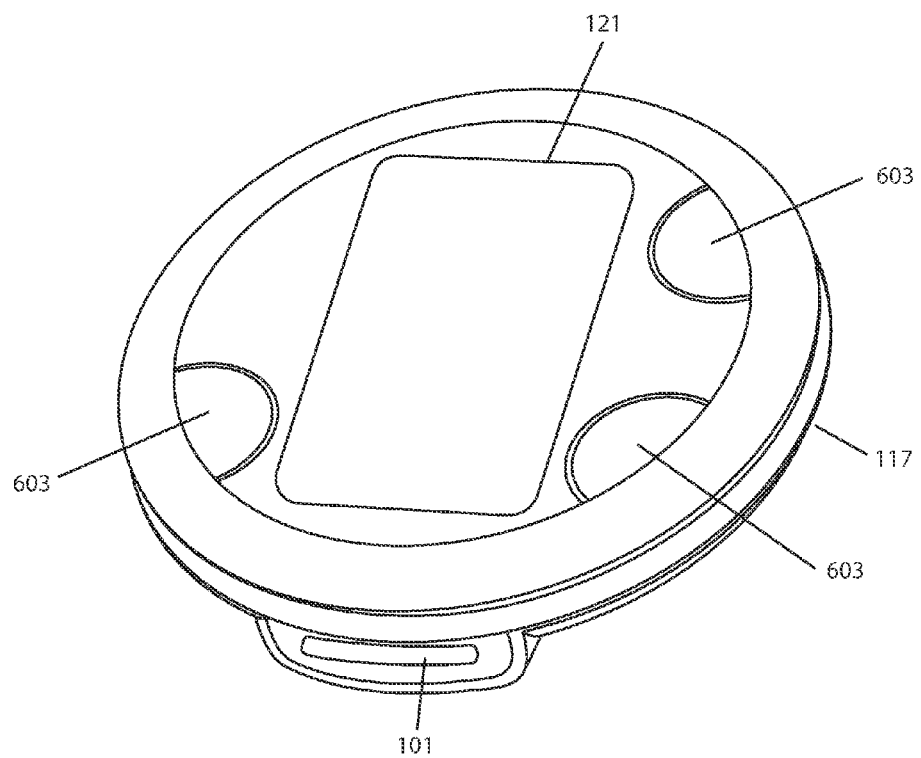
FIG. 18 shows a perspective view of an additional embodiment of an analyte meter accordingly to the present disclosure which includes a sensor port according to the present disclosure. The analyte meter is depicted in a substantially disk-shaped configuration with input units positioned peripherally to a display unit on the meter housing.
Figure 19:
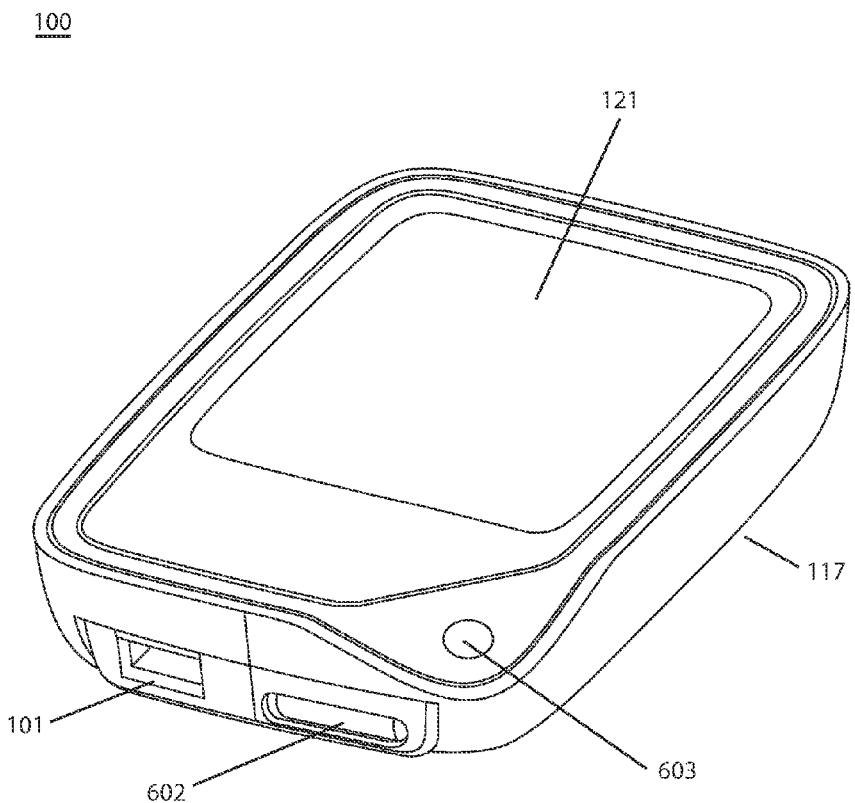
FIG. 19 shows a perspective view of an additional embodiment of an analyte meter accordingly to the present disclosure which includes a sensor port according to the present disclosure. The analyte meter is depicted in a configuration including a touch screen, an input unit and a communication port.

In one embodiment, the present disclosure provides a system, e.g., a diabetes management system, of which analyte sensor 100 is a component thereof. In such an embodiment, e.g., as shown in FIG. 16, communication unit 602 can be configured to communicate with one or more of a medication delivery device and/or system 605, a portable processing device 606, a computer 607, a network 608, an internet 609 and an analyte monitoring device and/or system 610 (e.g., a system including an implanted or partially implanted analyte sensor).

Input Unit

In some embodiments, an analyte meter 100 includes an optional input unit 603 coupled to the meter housing 117 and in communication with the processing unit. The input unit can be configured to include one or more input buttons, a jog wheel, capacitive sensing slider inputs, or combinations thereof. In one embodiment, a user or patient can operate the input unit to perform calculations and determinations associated with one or more medication dose calculation functions, such as a bolus dose calculation function, of the analyte meter 100. Input unit 603 is depicted as a system component in FIG. 16.

In one embodiment, the input unit includes one or more input buttons and/or keys, wherein each input button and/or key is designated for a specific task. Alternatively, or in addition, the input unit may include one or more input buttons and/or keys that can be "soft buttons" or "soft keys". In the case where one or more of the input buttons and/or keys are "soft buttons" or "soft keys", these buttons and/or keys may be used for a variety of functions. The variety of functions may be determined based on the current mode of the analyte meter 100, and may be distinguishable to a user by the use of button instructions shown on optional display unit 121 of analyte meter 100. Yet another input method may be a touch-sensitive display unit, as described in greater detail below.

In some embodiments, an input unit 603 functions to turn the analyte meter 100 on and/or off.

In addition, in some embodiments, the input unit is configured such that a user can operate the input unit to adjust time and/or date information, as well as other features or settings associated with the operation of analyte meter 100.

Voice Tagging

In one embodiment, the optional input unit includes a microphone (not shown). Such a microphone can be utilized in connection with a voice-tagging function of analyte meter 100. For example, analyte meter 100 can be configured to include a digital voice recorder which receives input from the microphone and stores digital voice files, e.g., as MP3 or WAV files. These digital voice files can be correlated with particular analyte measurement events to provide additional information which can be later reviewed, e.g., by the end user or a health care provider. For example, a user of analyte meter 100 may choose to record a brief message regarding his/her state of health or food intake activity in proximity to (e.g., within a predetermined time period of) the time of a particular analyte measurement.

Display

In some embodiments, an analyte meter according to the present disclosure includes an optional display unit, e.g., an optional display unit 121 as shown in FIG. 13 or a port (not shown) for coupling an optional display unit to the analyte meter 100. The display unit is in communication with the processing unit and displays the sensor signals and/or results determined from the sensor signals including, for example, analyte concentration, rate of change of analyte concentration, and/or the exceeding of a threshold analyte concentration (indicating, for example, hypo- or hyperglycemia).

Display unit 121 can be a dot-matrix display, e.g., a dot-matrix LCD display. In some embodiments, the display unit 121 includes a liquid-crystal display (LCD), thin film transistor liquid crystal display (TFT-LCD), plasma display, light-emitting diode (LED) display, seven-segment display, E-ink (electronic paper) display or combination of two or more of the above. The display unit 121 can be configured to provide, an alphanumeric display, a graphical display, a video display, an audio display, a vibratory output, or combinations thereof. The display can be a color display. In some embodiments, the display is a backlit display.

The display unit can also be configured to provide, for example, information related to a patient's current analyte concentration as well as predictive analyte concentrations, such as trending information.

In some embodiments an input unit and a display unit are integrated into a single unit, for example, the display unit 121 can be configured as a touch sensitive display, e.g., a touch screen display, where the user may enter information or commands via the display area using, for example, the user's finger, a stylus or any other suitable implement, and where, the touch sensitive display is configured as the user interface in an icon driven environment, for example.

In some embodiments, the optional display unit does not include a screen designed to display results visually. Instead, in some embodiments the optional display unit is configured to communicate results audibly to a user of the analyte meter, e.g., via an integrated speaker, or via separate speakers through a headphone jack or Bluetooth® headset.

Expanding Menu Item for Improved Readability

In some embodiments, the display unit 121 includes a graphical user interface including a plurality of menu items, wherein the display unit is configured to provide clarification with respect to the meaning of a menu item based on a user's response speed with respect to a user input for the menu item. The menu item could take any of a variety of forms, e.g., text, icon, object or combination thereof.

In one embodiment, the graphical user interface includes a menu which in turn includes a plurality of selectable menu items. As a user navigates through the menu, e.g., by highlighting or scrolling through individual menu items, a menu item that is either unreadable or incomprehensible to the user could cause the user to pause over a menu item to be selected. In one embodiment, a choice can be presented to the user, e.g., using a dedicated physical button on an input unit, or a soft key on the menu, that offers further explanation of the item to be selected without actually selecting the item. For example, the graphical user interface can be configured such that after a pre-determined period of time a soft key offers an explanation of the menu item to be selected, e.g., by displaying a soft key with the word "MORE", "ADDITIONAL INFORMATION", "EXPAND", "MAGNIFY", "HELP" or a variation thereof displayed thereon.

The pre-determined period of time may be based on a fixed factory preset value, a value set by the user or a health care provider, or through an adaptive mechanism based on an analysis of the user's speed of navigation from past interactions with the graphical user interface. In one embodiment, the pre-determined period of time is from about 5 to about 20 seconds, e.g., from about 10 to about 15 seconds.

If the offer for clarification and/or additional information is selected, e.g., by pressing the softkey, then the menu item to be selected can be displayed in a "high emphasis" mode, e.g., where the item is displayed as if a magnifying lens is held on top of the selected item. In some embodiments, additional emphasis of the menu item to be selected can be provided, e.g., by making the menu item change color, blink, or increase in size to a pre-determined maximum limit.

Alternatively, or in addition to, displaying the menu item in a "high emphasis" mode, a more descriptive explanation of what the menu item is could be provided in response to the selection of the offer for clarification and/or additional information. In some embodiments, the more descriptive explanation may be provided in response to the user pressing the soft key a second or additional time. In one embodiment, a more descriptive explanation of the menu item is provided in the form of scrolling text. Alternatively, or in addition, a pop-up window may be displayed which provides a more detailed explanation and/or animation of the menu item's function.

In another embodiment, pausing on a menu item beyond a pre-determined period of time results in display of a soft key as discussed above. Selection of the soft key by the user results in an audible communication to the user of the menu item's identity, e.g., using a built-in speaker (not shown) included in analyte meter 100. Selection of the soft key a second time results in an audible communication to the user which includes a descriptive explanation of the menu item's function.

In another embodiment, rather than utilizing a dedicated hardware button or a soft key, the graphical user interface can be configured to automatically display a menu item in a "high emphasis" mode and/or display additional information regarding the menu item's function once a user has paused for a pre-determined period of time with respect to a particular menu item. In such embodiments, the analyte meter 100 may include an optional hardware button or soft key which when depressed returns the display to a normal display mode from the "high emphasis" mode.

Modular Meter

In some embodiments, an analyte meter according to the present disclosure is configured as a modular meter or otherwise includes aspects of a modular meter or modular meter system. For example, an analyte meter including a sensor port according to the present disclosure may be configured to accept various hardware modules which may be removably attached to the analyte meter, wherein the various hardware modules are capable of providing various additional functionalities to the analyte meter once attached thereto. In some embodiments, the hardware modules include firmware configured to alter an existing functionality of the analyte meter and/or provide an additional functionality to the analyte meter. Additional disclosure of a modular analyte meter and associated hardware modules is provided in the U.S. patent application entitled "Modular Analyte Meter", listing Jean- Pierre Cole as the first named Inventor, the disclosure of which is incorporated by reference herein.

Support for on-Demand Analyte Determination Using an Analyte Sensor

In some embodiments, an analyte meter according to the present disclosure is further configured to receive analyte concentration data and/or signals indicative of an analyte concentration from an analyte sensor, e.g., an implanted or partially implanted analyte sensor or a radio-frequency (RF)-powered measurement circuit coupled to an implanted or partially implanted analyte sensor. In some embodiments, the analyte sensor is a self-powered analyte sensor. An analyte meter according to the present disclosure may include software configured to analyze signals received from the analyte sensor. Additional information related to self-powered analyte sensors and methods of communicating therewith are provided in U.S. patent application Ser. No. 12/393,921, filed on Feb. 26, 2009, entitled "Self-Powered Analyte Sensor", the disclosure of which is incorporated by reference herein.

Analyte Meter Including Pedometer

In some embodiments, an analyte meter as described herein is configured to include an integrated pedometer. The analyte meter may be configured, for example, to physically engage and communicate electronically with a commercially available pedometer device. The pedometer device may be positioned completely within the analyte meter housing. Alternatively, the pedometer device may engage, e.g., via snap-fit engagement, to a portion of the analyte meter housing. The pedometer device may be an electromechanical activity monitor or may utilize global positioning system (GPS) technology. Where the analyte meter is a modular meter as described herein, the pedometer functionality may be provided by a pedometer module configured to engage a base meter.

As an alternative to a physically integrated pedometer, the analyte meter may be configured to communicate with, e.g., via wired or wireless technology, and receive data from an external pedometer device which is not physically integrated with the analyte meter.

Where the analyte meter is physically integrated with or otherwise configured to communicate with a pedometer device, the analyte meter may include software and/or firmware designed to receive, store, analyze, display and/or communicate data received from the pedometer device. In some embodiments, such software and/or firmware may be stored on a pedometer module and configured to be run by an analyte meter processor in communication with the pedometer module.

Software and/or firmware which may be utilized include software and/or firmware designed to measure and/or display daily activity information for a user of the analyte meter, e.g., miles walked, stairs climbed, etc. Additional software features may include intensity of activity measurement (e.g., corresponding to the rate of user activity); daily, weekly and/or monthly activity targets which may be set by the user or a health care professional; display of current and/or previous activity level with respect to a targeted activity level; historical log of daily activity level (e.g., including trending information); integration with a health management system as described herein; and/or automatic logging of exercise data.

Analyte Meter with Selectively Activatable Features

Certain features and/or functionalities of an analyte meter may require or benefit from user-training prior to operation or use, e.g., a bolus dosage calculation function. For such features and/or functionalities, it may be desirable to initially provide the analyte meter with these features and/or functionalities in a disabled, but selectively activatable state. Once user-training is verified, e.g., by a health care professional, the features and/or functionalities may be activated. In other words, an analyte meter device may be provided with certain features and/or functionalities disabled "out of the box."

In some embodiments, a user interface, e.g., a touch screen display and/or input unit of the analyte meter provides a mechanism for entry of an activation code, which when entered, enables or "unlocks" one or more of the disabled features and/or functionalities. The activation code may be provided, for example, by a physician via a prescription. A unique activation code may be provided which corresponds to a serial number for a particular analyte meter device. Alternatively, a single activation code may be provided which is capable of activating features and/or functionalities of multiple analyte meter devices. A manufacturer of the analyte meter device may provide a service to accept and confirm a prescription of a physician and provide the activation code to a user of the analyte meter device.

The activation code may be transmitted and entered into the analyte meter in a number of ways. For example, a manufacturer or a manufacturer's representative may provide the code explicitly, e.g., via telephone or e-mail, to a user who then enters the code into the analyte meter using an input unit of the analyte meter. Alternatively, the activation code may be communicated and entered into the device from a remote location, e.g., using a communication unit of the analyte meter. This may occur, for example, when the analyte meter is in communication with a wireless data network.

In some embodiments, following entry of an activation code, the analyte meter displays available features and/or functionalities in a set-up menu from which a user of the analyte meter can then select particular features and/or functionalities to enable. In some embodiments, this set-up menu can also be utilized by the user to disable particular features and/or functionalities.

The activation of particular features and/or functionalities may also be provided for based on payment of a fee or a paid subscription service. For example, an analyte meter device may be provided with a variety of features and/or functionalities disabled, which features and/or functionalities may be enabled upon entry of an activation code, which activation code is provided based on payment an activation or subscription fee.

Analyte Meter Device Incorporated into Protective Skin or Case

In some embodiments, the present disclosure provides an analyte meter device, for example, an analyte meter as described herein, which is incorporated into a protective "skin" or case designed to fit a portable electronic processing device, e.g., a PDA, smart phone, etc. Such devices include for example, BlackBerry®, iPhone®, iPod®, and iTouch® devices as well as a wide variety of other portable electronic processing devices known in the art. Where the protective "skin" or case is designed to fit a portable electronic processing device, the analyte meter device itself does not need to physically engage the housing of the portable electronic processing device. Instead, the analyte meter device may be positioned in the protective "skin" or case such that when the protective "skin" or case is fit to the portable electronic processing device a convenient portable integrated device combination is provided. In addition, the protective "skin" or case may provide structural support for the integrated device combination.

As used herein the term "skin" refers to a flexible material, e.g., a flexible polymer material, configured to cover at least a portion of a portable electronic processing device. In some embodiments, a skin is sized and shaped to fit one or more external dimensions of a portable electronic processing device, while providing access to one or more features of the portable electronic processing device, e.g., one or more input units, displays, speakers, microphones, headphone jacks, cameras, communication ports, etc. For example, a skin may be configured to cover greater than 40%, e.g., greater than 50%, greater than 60%, greater than 70%, greater than 80% or greater than 90% of the exposed surface of a portable electronic device.

As used herein with reference to a portable electronic processing device, use of the term "case" as opposed to the term skin refers to a relatively rigid covering for a portable electronic processing device. As with the skin, in some embodiments, a case is sized and shaped to fit one or more external dimensions of a portable electronic processing device, while providing access to one or more features of the portable electronic processing device, e.g., one or more input units, displays, speakers, microphones, headphone jacks, cameras, communication ports, etc. For example, a case may be configured to cover greater than 40%, e.g., greater than 50%, greater than 60%, greater than 70%, greater than 80% or greater than 90% of the exposed surface of a portable electronic device.

The analyte meter device may be configured as one or more of a discrete analyte measurement device (e.g., a glucose meter configured to receive a glucose test strip), a component of an analyte measurement system including an implanted or partially implanted analyte sensor (e.g., a component of a continuous glucose measurement system), a component of an on-demand analyte measurement system and a component of a medication delivery system (e.g., an insulin delivery system including an insulin pump).

The analyte meter device which is incorporated into the protective skin or case is configured for one or two-way communication with a processor and/or control unit of the portable electronic processing device. The communication may be wired or wireless, e.g., using one or more of the wireless communication protocols described herein.

In specific embodiments, communication between processor and/or control unit of the portable electronic processing device and the analyte meter device is accomplished using a "wired" connection between a communication unit and/or communication port of the analyte meter device and a hard-wired communication port positioned on the portable electronic processing device (e.g., a USB port or a proprietary serial interface such as that found in the iPhone®). For example, the communication unit and/or communication port of the analyte meter may include a male USB connector while the portable electronic processing device includes a corresponding female USB connector. Connection of the two connectors provides a physical and electrical connection between the analyte meter device and the portable electronic processing device.

In some embodiments, where the analyte meter device is configured as a discrete analyte measurement device, it may include a sensor port, e.g., a sensor port as described herein. In such embodiments, the discrete analyte measurement device may or may not include a display unit which is separated from a display unit of the portable electronic processing device. Where the discrete analyte measurement device does not include a separate display unit, analyte measurement results obtained using the discrete analyte measurement device may be displayed on the display unit of the portable electronic processing device.

In some embodiments, where the analyte meter device is configured as a component of an analyte measurement system including an implanted or partially implanted analyte sensor (e.g., a continuous analyte sensor), the analyte meter device in combination with the portable electronic processing device coupled thereto provide a portable hand-held component of the measurement system. In such embodiments, the analyte meter device may be configured to include a communication unit which provides for wireless, e.g., RF, communication with an on-body portion of the analyte measurement system, e.g., an implanted or partially implanted analyte sensor or an RF-powered measurement circuit coupled to an implanted or partially implanted analyte sensor.

In some embodiments, where the analyte meter device is configured as a component of an on-demand analyte measurement system, the analyte meter device in combination with the portable electronic processing device coupled thereto provide a portable hand-held component of the measurement system. In such embodiments, the analyte meter device may be configured to include a communication unit which provides for wireless, e.g., RF, communication with an on-body portion of the on-demand analyte measurement system when the portable hand-held component is positioned in proximity to the on-body portion of the on-demand analyte measurement system. In this manner, periodic or intermittent analyte readings may be obtained and communicated to a user. In some embodiments, a button or other input device on the analyte meter device may be utilized by a user to initiate the on-demand acquisition of measurement data. Alternatively, the acquisition of measurement data may be initiated using a user interface of the portable electronic processing device.

In some embodiments, where the analyte meter device is configured as a component of a medication delivery system, e.g., an insulin delivery system, the analyte meter device in combination with the portable electronic processing device coupled thereto provide a portable hand-held component of the medication delivery system. In such embodiments, the analyte meter device may be configured to include a communication unit which provides for wireless, e.g., RF, communication with a medication delivery device, e.g., an insulin pump.

In some embodiments, the analyte meter device is configured to be powered by a portable electronic processing device to which the analyte meter device is coupled, e.g. via a USB connection. Alternatively, or in addition, the analyte meter device may include a separate power source, e.g., a disposable or rechargeable battery. Additional information related to the powering of an analyte meter device coupled to a portable electronic processing device is provided in U.S. Pat. No. 7,041,468, the disclosure of which is incorporated by reference herein.

The analyte meter device may include a memory for storing one or more software applications designed to be uploaded and/or run by a processor or controller unit of a portable electronic processing device to which the analyte meter device is coupled.

Software and/or Firmware

The analyte meters or other devices disclosed herein may include software and/or firmware configured to be executed by an internal and/or external processing unit. In some embodiments, an analyte meter is configured such that one or more programs are launched automatically, e.g., utilizing a plug and play standard, when the meter is connected to an external processing device, e.g., a computer or portable electronic processing device. The one or more programs may be configured to run on a variety of common hardware platforms (e.g., PC, MAC) and operating systems (e.g., Windows, MAC OS, Linux). The one or more programs may be stored in the analyte meter, e.g., within a machine-readable storage medium (e.g., flash memory or other non-volatile memory) and executed by one or more general-purpose or special-purpose programmable microprocessors and/or microcontrollers. Alternatively, one or more programs may be stored in one or more removable hardware modules as discussed above. Examples of functions which may be implemented by software and/or firmware include, but are not limited to those discussed below and elsewhere herein.

Creating an Event Log

Various events (e.g., measurement readings, nutritional intake information (e.g., carbohydrate intake information), insulin dosage and times, exercise records, meal-time records, note records, medication-time records, etc.) may be recorded along with date/time tags. Events may be recorded automatically by the analyte meter (e.g., upon measurement reading). Alternatively, or in addition, input elements on the analyte meter may be used by a user to input event data and/or non-event data.

In some embodiments, entry of carbohydrate intake data may be facilitated by providing for the utilization of bar code scanner technology in combination with a database which links product bar codes to carbohydrate information for the product. For example, an analyte meter device such as an analyte meter 100 as described herein or another portable electronic processing device may include an integrated bar code reader. In addition, the analyte meter or portable electronic processing device may be configured to include, e.g., in a data storage unit, a database which links a product's bar code to its nutritional content (e.g., its carbohydrate content). Alternatively, such a database could be stored on a remote device and/or system which may be accessed by the analyte meter device or portable electronic processing device, e.g., using a communication unit as described herein. In this manner, when a user scans a bar code associated with a food item he or she intends to consume, the nutritional information (e.g., carbohydrate content), can be automatically entered into an event log and/or database for later analysis.

In another embodiment, where a bar code and/or corresponding nutritional information are not available, a user may utilize digital camera technology, e.g., a digital camera incorporated into an analyte meter device or another portable electronic processing device to capture a digital image of a food item to be consumed. Such digital images may then be compared to images of food items having a known nutritional content, e.g., using image recognition technology. Alternatively, or in addition, such digital images may be utilized, e.g., by a health care professional, in connection with user training designed to assist the user in assessing the carbohydrate content of a food item.

In some embodiments, an analyte meter, portable electronic processing device, and/or health management software may be configured to enable a user to "tag" or link one or more bar code readings or digital images with additional information entered by the user, e.g. information related to a subsequent analyte measurement or measurements.

Visually Representing Data

Collected and/or analyzed data may be represented visually to the user (e.g., on the display unit of the analyte meter and/or a remote device). For example, data from the event log may be presented in various formats and/or further manipulated and presented. Data may be used to generate graphs and reports that help a user such as a diabetic to track glucose and other related information. The test data may be graphed in many ways according to various default or pre-programmed graphs or according to filtering and preferences inputs from a user. The graphs may be generated and displayed on the analyte meter and/or a remote device, e.g., a remote device configured to communicate with the analyte meter.

Remote devices configured to communicate with the analyte meters disclosed herein may be configured for printing the graphs and/or reports. The remote devices may also be configured to receive data from a storage unit of the analyte meter and enter such data into a database located on the remote device. A remote device could also be utilized for backing-up data and for downloading applications programs to the analyte meter and for communicating with other computers over one or more networks, e.g., for viewing of data by the user, a physician, and/or a third party.

Trend Calculation

Data from the event log may also be used to perform trending calculations. For example, an analyte meter according to the present disclosure may be capable of displaying a graph of the analyte level over a period of time. Examples of other graphs that may be useful include graphs of the rate of change or acceleration in the rate of change of the analyte level over time (i.e., trending data). Trending data may be used by other applications, e.g., in bolus calculations and/or alerts.

Trending data may also be presented via a display unit on the analyte meter. The display unit may contain symbols, e.g., directional arrows, or other indicators that are activated under certain conditions (e.g., a particular symbol may become visible on the display when a condition, such as hyperglycemia, is indicated by signals from the sensor). Other indicators may be activated in the cases of hypoglycemia, impending hyperglycemia, impending hypoglycemia, etc.

Additional information regarding the use of logs and trending by analyte meters can be found within U.S. Pat. Nos. 7,041,468, and 6,175,752, disclosures of which are incorporated herein by reference.

Alerts, Alarms and/or Reminders

An alert may be activated by the analyte meter and conveyed to the user, e.g., via the display unit. An alarm may be activated if an analyte sensor, for example, indicates a value that is beyond a measurement range of the analyte sensor. An alarm system may also, or alternatively, be activated when the rate of change or acceleration of the rate of change in analyte level increase or decrease reaches or exceeds a threshold rate or acceleration, e.g., to indicate a hyperglycemic or hypoglycemic condition is likely to occur.

An alarm system may be configured to activate when a single data point meets or exceeds a particular threshold value. Alternatively, the alarm may be activated only when a predetermined number of data points spanning a predetermined amount of time meet or exceed the threshold value. As another alternative, the alarm may be activated only when the data points spanning a predetermined amount of time have an average value which meets or exceeds the threshold value.

The alarm system may contain one or more individual alarms. Each of the alarms may be individually activated to indicate one or more conditions of the analyte. The alarms may be, for example, auditory or visual. Other sensory-stimulating alarm systems may be used including alarm systems which heat, cool, vibrate, or produce a mild electrical shock when activated.

Dynamic Scheduling of Therapy Reminders

The present disclosure provides software and/or firmware configured to perform one or more active scheduling algorithms. An active scheduling algorithm can provide a user of an analyte meter a recommended time and/or date for a subsequent therapy administration (e.g., by displaying such information on display 121 of analyte meter 100), wherein the recommended time and/or date is determined based on a retrospective analysis of previously administered therapies as compared to a recommended therapy sequence and/or profile. As used herein, the term "therapy" includes analyte measurement as well as the administration of a medication.

The therapy reminders can be determined and configured by a qualified health care provider, such as a physician, clinical specialist or nurse. An analyte meter 100 can then be configured with an appropriate scheduling algorithm directly by the health care provider using an optional input unit incorporated into the analyte meter 100, via a data management system that interfaces with the analyte meter 100, and/or via another portable device configured to communicate with the analyte meter 100. In this manner, a health care provider can update therapy recommendations electronically and communicate the therapy recommendations to an end user.

In one embodiment, a suitable scheduling algorithm provides a reminder to the user based on an analysis of the history of analyte measurements, e.g., blood glucose measurements, made by the user and compared to scheduled analyte measurements yet to be completed. The scheduling algorithm updates the reminder during the course of the day, such that the user is presented with the next scheduled time conforming to the scheduling profile. The dynamic scheduling can continue over multiple days until the user has completed all measurements conforming to the schedule. After the therapies are completed according to the recommended schedule, the scheduling algorithm can be configured to reset and start again, or alternatively a different scheduling algorithm may be activated.

The scheduling algorithm can be configured to provide feedback to the user at any time during the scheduled therapy administration period. For example, the scheduling algorithm can be configured to provide the user with an indication of how much of the schedule has been completed, and/or how many recorded measurement times did not conform to the recommended measurement time profile.

A non-limiting example of a dynamic scheduling procedure according to the present disclosure is as follows: (A) The measurement profile is defined to include the recording of 7 analyte readings before and after lunch, with 30 minute separation, starting at 1 hour prior to lunch (11:00 am). The recommended times are 11:00 am, 11:30 am, 12:00 pm, 12:30 pm, 1:00 pm, 1:30 pm, and 2:00 pm. (B) If the user's first analyte measurement is at 12:00 pm, the algorithm would recommend that the next measurement be performed at 12:30 pm. (C) If the user does not perform an analyte measurement at 12:30 pm, the algorithm would suggest 1:00 pm, and so on. (D) If the user does perform an analyte measurement later in the day, e.g., 8:00 pm, this measurement is not considered as advancing the completion of the measurement profile. (E) If the user on the second day performs an analyte measurement at 12:00 pm, this measurement is also not considered as advancing the completion of the measurement profile, as it was already completed on the previous day. (F) If the user on the second day then samples at 1:00 pm, this measurement is considered to advance the completion of the measurement profile. Based on the above, the analyte meter would display, for example, a summary report that 29% (2/7) of the therapy reminders have been completed, and that 2 of the 4 readings did not conform to the scheduled reminders. (G) In addition, the analyte meter would report the outstanding measurement times, e.g., 11:00 am, 11:30 am, 12:30 pm, 1:30 pm and 2:00 pm.

Control of a Drug Administration System

An analyte meter 100 may be configured to control a drug administration system based on, for example, measurement readings. The analyte meter 100 may provide (or communicate with a remote device to provide) a drug to counteract the high or low level of the analyte in response to a measurement reading and/or continuous measurement reading (e.g., with an implanted or partially implanted sensor). In one embodiment, the drug administration system includes an insulin pump. See, e.g., FIG. 16.

Implement an Application Programming Interface

An analyte meter 100 may be configured to implement an Application Programming Interface (API) to enable interaction with other devices and/or software, e.g., medication delivery pumps.

Dosage Calculation

The processing unit may be configured to determine a dosage, e.g., an insulin bolus dosage, based on one or more signals received from the analyte sensor as discussed above. Accordingly, in some embodiments, the analyte meter includes a software program which may be implemented by the processing unit to perform one or dosage determination algorithms. In some embodiments, the one or more dosage determination algorithms are modifiable by a user of the analyte meter, e.g., using the optional input unit coupled to the meter housing. Alternatively, or in addition, the one or more dosage determination algorithms may be modified via a computer or other suitable device in communication with the analyte meter. In some embodiments, an analyte meter according to the present disclosure is provided with software including a preset dosage determination algorithm which is set prior to providing the analyte meter to an end user. Such a preset dosage determination algorithm may be configured based on information provided by an end user or a health care provider to a provider, e.g., a manufacturer, of the analyte meter.

Smart Health Port

Figure 20:
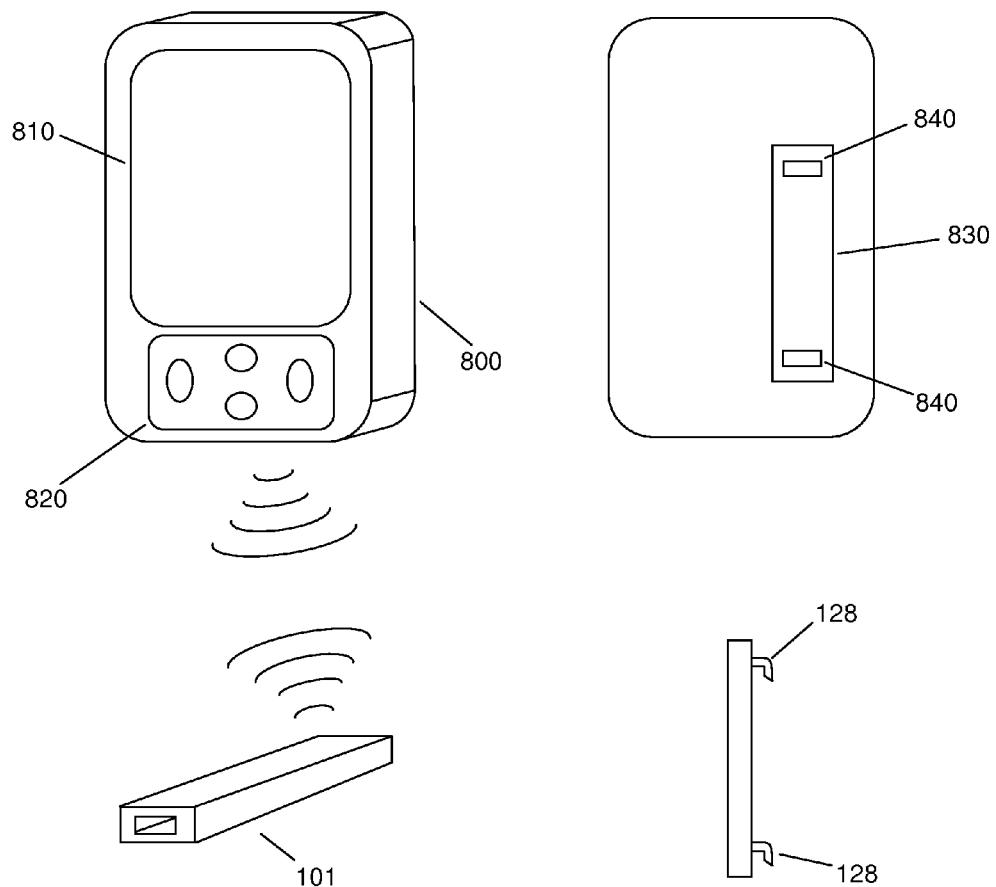
FIG. 20 shows a portable electronic processing device according to one embodiment of the present disclosure (top left—perspective view, top right—rear view) configured to releasably engage a sensor port according to one embodiment of the present disclosure (bottom right—perspective view, bottom right—side view)

In some embodiments, a sensor port 101 according to the present disclosure is not incorporated into an analyte meter 100, but is instead configured as a self-contained unit. In such embodiments, the sensor port 101 can be configured to communicate with an external electronic device configured to process and/or display an analyte measurement based on information received from the sensor port 101 (e.g., a portable electronic processing device 800 as shown in FIG. 20. For example, the external electronic device may be a mobile phone, i-Pod™; computer, or any other suitable electronic device capable of processing and/or displaying an analyte measurement.

The communication between the sensor port 101 and the external electronic device can be via wireless (e.g., Bluetooth® or any other suitable wireless communication method described herein) or wired (e.g., USB) technology. In some embodiments, the sensor port 101 is configured to include a communication unit as described previously herein.

In some embodiments, the sensor port 101 may be configured to detachably connect to a portable electronic processing device 800 (See, e.g., FIG. 20). In other words, the sensor port 101 may be configured to releasably engage a portable electronic processing device 800. Portable electronic processing device 800 is shown with optional display unit 810 and optional input unit 820. In some embodiments, sensor port 101 is configured to detachably connect to portable electronic processing device 800. For example, sensor port 101 may includes optional protrusions 128 which are configured to mate with recesses 840 located in a sensor port dock 830 so as to detachably connect sensor port 101 to portable electronic processing device 800. The sensor port 101 may be configured such that when connected to the portable electronic processing device 800, the sensor port 101 can communicate with the portable electronic processing device 800. Such communication may be wireless or wired and may utilize one or more of the communication methods discussed herein.

The sensor port 101 may or may not include a display as described previously herein for displaying an analyte measurement to a user of the sensor port 101.

In some embodiments, the external electronic device is configured to analyze and/or interpret signals received from an analyte sensor inserted into sensor port 101 using software downloaded from a server and/or network. For example, the external electronic device can be configured to connect via an internet connection to a webpage and/or domain and download a software application configured to analyze and/or interpret signals received from the analyte sensor. An internet connection can also be utilized to download updates to existing software located on the external electronic device.

Additional Functional Units

A variety of analyte meters are known in the art, many of which include additional components and functionalities which can be readily incorporated into the analyte meters described herein. Disclosure of such additional components and functionalities can be found, for example, in U.S. Patent Application Publication No. 2008/0119702, U.S. Patent Application Publication No. 2008/0114280, and U.S. Patent Application Publication No. 2008/0119710, the disclosure of each of which is incorporated by reference herein.

Power for Analyte Meter

The analyte meter 100 may be configured to include an internal power unit (not shown) coupled to meter housing 117. In another embodiment, the analyte meter does not include an internal power unit and is instead powered by an attachment module coupled to the analyte meter, wherein the attachment module includes a power unit. In one embodiment, the analyte meter does not include an internal power unit and is operationally powered by an attachment module, but does include a smaller back-up power unit to preserve data measurements, user settings, date/time settings, etc. The power unit may include, for example, button or AAA-size batteries.

Methods of Using Analyte Meter

The analyte meters described herein find use in methods for determining the concentration of an analyte in a fluid sample from a subject. Generally, these methods include inserting an analyte sensor into an analyte meter 100; contacting a fluid sample e.g. a blood sample, with the analyte sensor; generating a sensor signal at the working electrode; and determining the concentration of the analyte using the generated sensor signal. Examples of specific electrochemical reactions which can be utilized to produce a sensor signal are described in detail in U.S. Pat. No. 6,592,745, the disclosure of which is incorporated by reference herein.

In one embodiment, the analyte sensor is an analyte sensor 200 or an analyte sensor 300 as described herein. However, it is contemplated that analyte sensors other than those specifically described herein may be configured to operate with the analyte meters 100 disclosed herein. Furthermore, analyte meters as described herein can be configured to be compatible with a variety of analyte sensors.

In one embodiment, the determining step includes determining the concentration of the analyte by amperometry, coulometry, potentiometry, and/or voltametry, including square wave voltametry, using the analyte sensor.

In one embodiment, the method includes a medication dosage determination step. For example, where the analyte is glucose, the method can include a determination step in which the processing unit performs an algorithm to determine an insulin dose, e.g., a bolus insulin dose, based on the concentration of glucose in the sample.

In another embodiment, the method includes an administering step wherein a medication dose, e.g., an insulin dose, determined according to the method is administered to the subject via a medication delivery device, e.g., a needle, syringe, pump, catheter, inhaler, transdermal patch, or combination thereof.

In another embodiment, the administering step includes administering a medication dose, e.g., an insulin dose, determined according to the method to the subject via a medication delivery device positioned at a distance from the analyte meter and in communication with the analyte meter.

A medication dose, e.g., a bolus dose, determined according to the above methods can be displayed to the user via optional display unit 121 of analyte meter 100.

Integration with Medication Delivery Devices and/or Systems

In some embodiments, the sensor ports and/or analyte meters disclosed herein may be included in a medication delivery device and/or system, e.g., an insulin pump module, such as an insulin pump or controller module thereof. In some embodiments the sensor port and/or meter is physically integrated into a medication delivery device (See, e.g., FIGS. 22 and 23 for physically integrated sensor ports). In other embodiments, the sensor port and/or meter is configured to detachably connect to a medication delivery device (See, e.g., FIGS. 21A and 21B for detachable sensor ports). In still other embodiments, a sensor port or an analyte meter or other device including a sensor port as described herein may be configured to communicate with a remote medication delivery device or another component of a medication delivery system (See, e.g., FIG. 16).

Figure 21A:
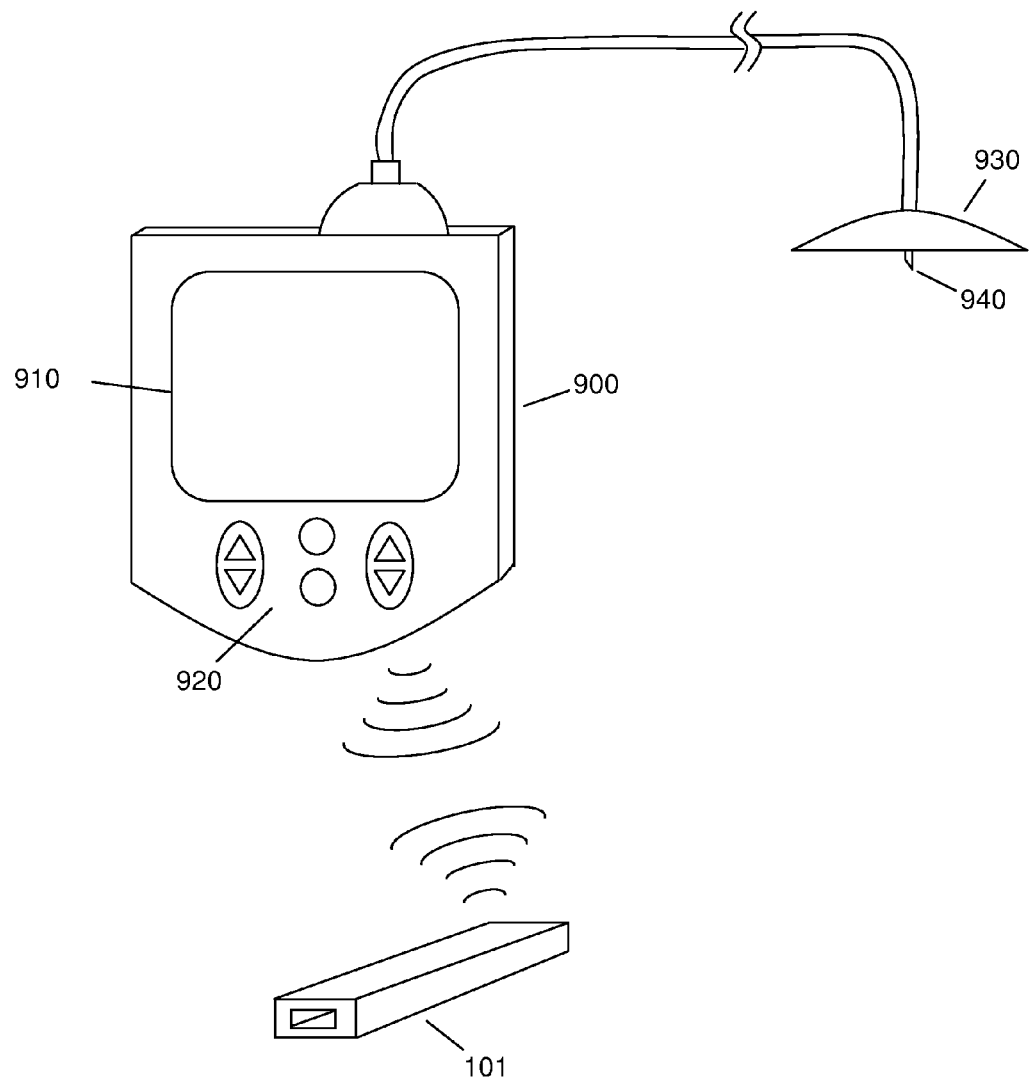
FIG. 21A shows a medication delivery device according to one embodiment of the present disclosure (top) configured to releasably engage a sensor port according to one embodiment of the present disclosure (bottom)

In some embodiments, a sensor port 101 according to the present disclosure is configured to communicate with a medication delivery device 900, e.g., an insulin pump (See, e.g., FIGS. 21A and 21B). With reference to FIGS. 21A and 21B, sensor port 101 may be configured to detachably connect to medication delivery device 900. In other words, the sensor port 101 may be configured to releasably engage a medication delivery device 900. Medication delivery device 900 is shown with optional display unit 910 and optional input unit 920. Medication delivery device 900 is also shown connected to an on-body pump element 930, which includes infusion needle 940. Sensor port 101 may includes optional protrusions 128 which are configured to mate with recesses 940 located in a sensor port dock 930 so as to detachably connect sensor port 101 to medication delivery device 900. The sensor port 101 may be configured such that when connected to the medication delivery device 900, the sensor port 101 can communicate with the medication delivery device 900. Such communication may be wireless or wired and may utilize one or more of the communication methods discussed herein.

Figure 22:
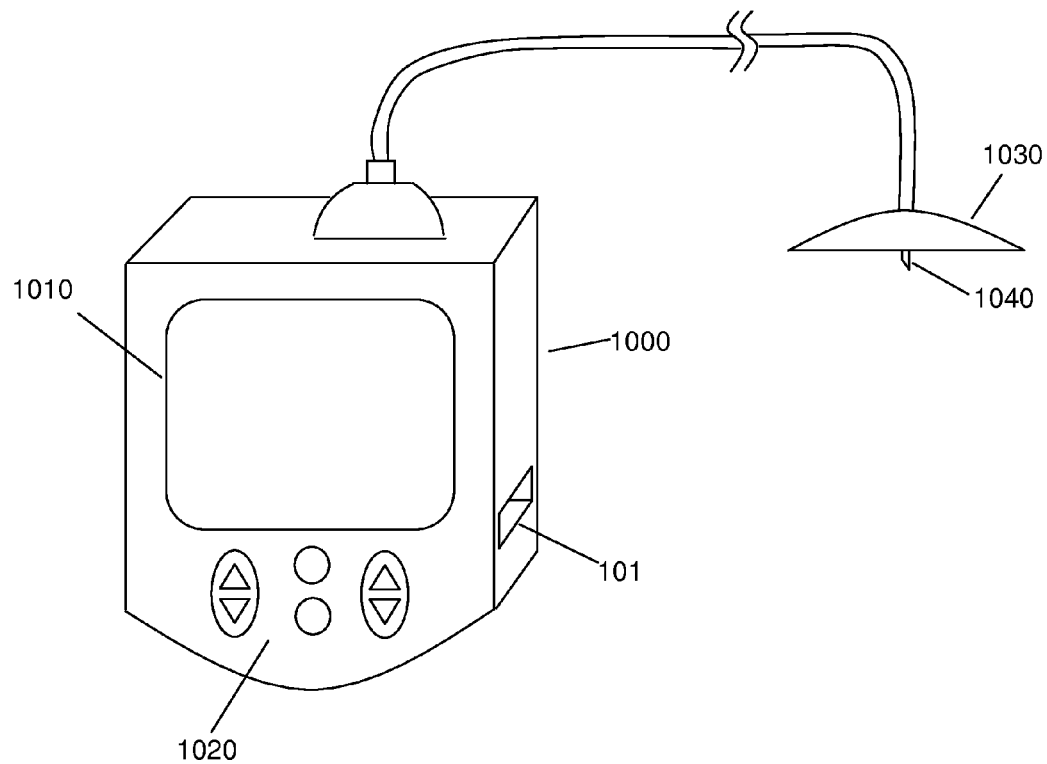
FIG. 22 shows a medication delivery device according to one embodiment of the present disclosure including a physically integrated sensor port according to one embodiment of the present disclosure.

In some embodiments, a sensor port 101 according to the present disclosure is physically integrated into a medication delivery device. With reference to FIG. 22, a medication delivery device 1000 is provided which includes a sensor port 101 physically integrated into the housing of the medication delivery device 1000. As shown in FIG. 22, medication delivery device 1000 may also include optional display unit 1010 and optional input unit 1020. Medication delivery device 1000 is also shown connected to an on-body pump element 1030, which includes infusion needle 1040.

Figure 23:
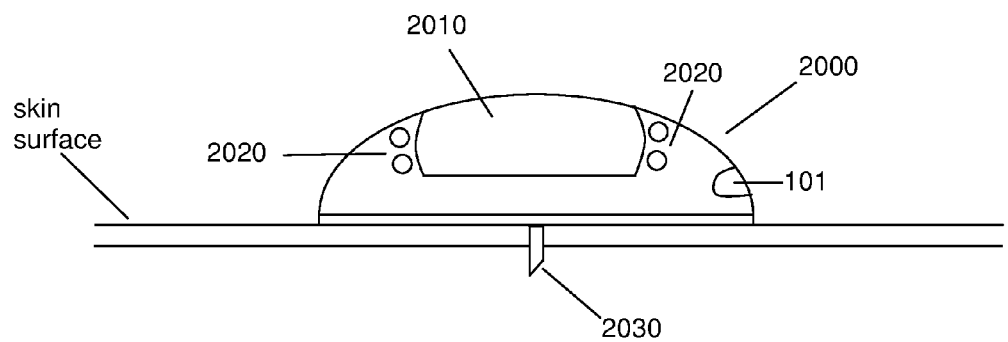
FIG. 23 shows a disposable on-body medication delivery device according to one embodiment of the present disclosure including a physically integrated sensor port according to one embodiment of the present disclosure.

In some embodiments, a sensor port 101 according to the present disclosure is physically integrated into a disposable on-body medication delivery device. With reference to FIG. 23, a medication delivery device 2000 is provided which includes a sensor port 101 physically integrated into the housing of the medication delivery device 2000. As shown in FIG.

23, medication delivery device 2000 may also include optional display unit 2010 and optional input unit 2020. Medication delivery device 2000 is configured as a disposable on-body medication delivery device which includes infusion needle 2030.

Additional information regarding medication delivery devices and/or systems, such as, for example, integrated systems, is provided in U.S. Patent Application Publication No. 2006/0224141, published on Oct. 5, 2006, entitled "Method and System for Providing Integrated Medication Infusion and Analyte Monitoring System", and U.S. Patent Application Publication No. 2004/0254434, published on Dec. 16, 2004, entitled "Glucose Measuring Module and Insulin Pump Combination," the disclosure of each of which is incorporated by reference herein. Medication delivery devices which may be provided with an analyte meter which in turn includes a sensor port as described herein include, e.g., a needle, syringe, pump, catheter, inhaler, transdermal patch, or combination thereof. In some embodiments, the medication delivery device or system may be in the form of a drug delivery injection pen such as a pen-type injection device incorporated within the housing of an analyte meter. Additional information is provided in U.S. Pat. Nos. 5,536,249 and 5,925,021, the disclosure of each of which is incorporated by reference herein.

The medication delivery system may be used for injecting a dose of medication, such as insulin, into a patient based on a prescribed medication dosage, and may be automatically updated with dosage information received from an analyte meter. In another embodiment, the medication dosage of the medication delivery system may include manual entry of dosage changes made through, for example, an optional input unit coupled to the housing of an analyte meter. Medication dosage information associated with the medication delivery system may be displayed on an optional display unit disposed on a housing of an analyte meter.

Analyte Detection Systems

An analyte meter 100 as described herein can be a component of one or more analyte detections systems. For example, an analyte detection system according to the present disclosure can include an analyte meter 100 as described herein in addition to one or more sample acquisition and/or testing elements known in the art. In one embodiment, an analyte detection system according to the present disclosure includes an analyte sensor, e.g., an analyte sensor 200 or an analyte sensor 300 as described herein, and a lancet. In some embodiments, the analyte sensor 200 and the analyte sensor 300 are in the form of test strips.

In some embodiments, a lancet and an analyte sensor 200 or an analyte sensor 300 in the form of a test strip are integrated into the housing of the analyte meter 100. In specific embodiments, a plurality of analyte sensors and a plurality of lancets are integrated into the housing of an analyte meter 100. In other embodiments, the lancet and the test strip are not integrated into the housing of the analyte meter, but are instead included in the system as separate components.

Where the test strip is integrated into the housing of an analyte meter 100, the housing can be configured to hold one or more cartridges or magazines containing test strips to be used in the operation of the system. Similarly, where the lancet is integrated into the housing of an analyte meter 100, the housing can be configured to hold one or more cartridges or magazine containing lancets to be used in the operation of the system.

Additional systems incorporating the analyte meters described herein will be readily apparent to those of ordinary skill in the art upon reading the present disclosure.

Analytes

A variety of analytes can be detected and quantified using the disclosed analyte sensors and meters. Analytes that may be determined include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones (e.g., ketone bodies), lactate, oxygen, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be determined. Assays suitable for determining the concentration of DNA and/or RNA are disclosed in U.S. Pat. No. 6,281,006 and U.S. Pat. No. 6,638,716, the disclosures of each of which are incorporated by reference herein.

Health Management System

An analyte meter or other device including a sensor port as described herein can be configured to operate as one component of a health management system. For example, in one embodiment, an analyte meter or other device including a sensor port as described herein is configured to communicate, e.g., via a communication unit as described herein, with a central data repository which is in turn configured to analyze and store user-specific data in a user-specific therapy management database. The communication between the analyte meter or other device including a sensor port as described herein and the central data repository may be initiated by the user or may occur automatically, e.g., when the analyte meter or other device is in range of a wireless network.

In one embodiment, the analyte meter or other device including a sensor port as described herein is one of multiple devices utilized by the user and configured to communicate with the central data repository. In such an embodiment, the central data repository can be configured to integrate incoming data from multiple devices. For example, the central data repository can be configured to integrate data received from one or more Personal Digital Assistants (PDAs), mobile phones, iPhone®(s), etc. The central data repository may be located on a server and/or computer network and may include a variety of software and/or hardware components as appropriate.

The data may be transmitted from the devices in a variety of ways, e.g., via text messaging, e-mail, micro-blogging services (e.g., Twitter™), voicemail, or any other suitable messaging format. Depending on the transmission form, data may be sent by a user to, e.g., a phone number, text number, e-mail address, Twitter™ account, etc. The received data can include a variety of health related information depending on the health condition being managed. For example, in the context of diabetes, the data received by the central data repository can include, e.g., meal data, exercise data, insulin administration data, blood glucose data, blood ketone data, etc.

User-specific data received from one or more of these devices can be merged with data received from an analyte meter or other device including a sensor port as described herein. Once the data is received, the central data repository interprets the message as containing, e.g., meal data exercise data, insulin administration data, blood glucose data, blood ketone data, etc., and populates the user-specific therapy management database accordingly.

The user-specific therapy management database can be configured such that it is accessible by the user, a health care provider, or other suitable party, for viewing and/or editing. For example, access to the user-specific therapy management database may be provided via a website, e.g., a secure website. In one embodiment, the user-specific therapy management database is hosted on a server and the system is configured such that a health care provider can access the user-specific therapy management database from a computer via a wired or wireless IP connection to the server hosting the user-specific therapy management database.

Health Management System-Associated Software and/or Firmware

In one embodiment, the present disclosure provides one or more software applications which facilitate specific functionalities of a health management system, e.g. a diabetes management system. Such software applications may reside, for example, in the memory of an analyte meter as described herein. Alternatively, or in addition, such software may be located on a computer, server, and/or network located external to an analyte meter as described herein.

In one embodiment, such software resides in the memory of an analyte meter as described herein and is configured to launch automatically, e.g., via a "Plug and Play" standard, on an external processing device such as a desktop computer or laptop computer when the analyte meter is connected to the external processing device, e.g. via a USB connection.

In another embodiment, such software resides in memory of an external processing device such as a desktop computer or laptop computer and is configured to launch automatically on the external processing device when an analyte meter is connected to the external processing device, e.g. via a USB connection.

In another embodiment, such software resides in memory of an analyte meter as described herein and is configured to run on the analyte meter itself.

In another embodiment, such software resides in memory of a processing device other than an analyte meter and is configured to run on the processing device itself.

Instant Messaging

One such software application is one which in addition to providing data display and analysis tools for health management also provides Instant Messaging (IM) functionality.

For example, in one embodiment health management software, e.g., diabetes management software, is provided which allows a health care provider using the health management software to review data related to a user's health, e.g., diabetes related data, and send comments, therapy recommendations, and/or scheduling information via IM to an interface accessible by the user. The interface could be, e.g., a user's personal computer, a portable electronic device, or an analyte meter with communication functionality as described previously herein.

In one embodiment, health management software, e.g., diabetes management software, is provided which allows an end user to utilize the health management software to review data related to the end user's health, e.g., diabetes related data, and send comments, questions, and/or analyte measurement results via IM to an interface accessible by a health care provider.

The above functionalities may be combined in a single software application such that the health care provider and the end user are capable of reviewing data related to the end user's health and communicating with each other via IM functionality built in to the software application.

Health management software having integrated, i.e., "built in", IM functionality can also be utilized to allow communication between an end user and a customer support representative in order to provide the end user with product support information, e.g. for the software itself or an analyte meter or other product utilized in connection with the health management system.

In one embodiment, the health management software is configured to prompt the end user to select an IM recipient among, e.g., product support specialists; health management specialists; e.g., diabetes management specialists; and product sales specialists.

The mode of communication utilized by the IM feature of the health management software may be text-based, voice-based and/or video-based. It should be noted that responses to the IM communications need not be in real-time.

A software application configured to provide IM functionality may be stored in and/or run from an analyte monitoring device, e.g., an analyte meter as described herein. Alternatively, the software application may be stored in and/or run from a processing device such as a smart phone device, PDA, server device, laptop or desktop computer.

Report Plug-In for Health-Management Software

In one embodiment, the present disclosure provides a stand-alone health management software application capable of incorporating a report plug-in application which provides for full integration of new reports into the stand-alone health management software application. Such a health management software application may be stored in and/or run from an analyte monitoring device, e.g., an analyte meter as described herein. Alternatively, the software application may be stored in and/or run from a processing device such as a smart phone device, PDA, server device, laptop or desktop computer.

The report plug-in application can be made available to a user at start-up of the stand-alone health management software application and/or via a menu action. For example, in one embodiment, a health management software application is provided to a user with certain reports "built-in." At a later time point, the set of built-in reports can be augmented with one or more newly published reports. The user can be made aware of the additional reports by, e.g., a message displayed upon start up of the health management software application.

In one embodiment, when the new report is accepted by the user, the new report is fully integrated into the stand-alone health management software application, i.e., the new report includes all of the functionalities that are common to the existing set of reports. Such functionalities may include, e.g.: (A) inclusion of reports in existing or new dashboards, (B) relaying user event data to other application components, e.g., other reports displayed on the dashboard, (C) receiving user event data from other application components, e.g., other reports displayed on the dashboard, (D) printing of a report using the application print engine, (E) the report can be uninstalled by the user, and (F) multiple versions of the same report are supported by implementing a versioning scheme.

As used herein, the term "dashboard" is used to refer to a visualization component of a health management software application which includes multiple component reports. The health management software application may be configured to provide multiple dashboards having different combinations and or arrangement of displayed reports.

Health-management software is well known in the art and includes, e.g., the CoPilot™ Health Management System and the PrecisionWeb™ Point-of-Care Data Management System available through Abbot Diabetes Care Inc., Alameda, Ca.

In one embodiment, the health management software application provided by the present disclosure is a diabetes management software application. Such an application may be configured to run one or more reports relevant to diabetes management, e.g., a diary list report, glucose modal day report, glucose line report, glucose average report, glucose histogram report, glucose pie chart report, logbook report, lab and exam record report, statistics report, daily combination view report, weekly pump review report, and an HCP group analysis report. See, e.g., the CoPilot™ Health Management system Version 4.0 User's Guide, available online at the web address located by placing "www." immediately preceding "abbottdiabetescare.com/static/content/document/ART12542_Rev-A_US_English.pdf", the disclosure of which is incorporated by reference herein.

Customizable Dashboards for Health Management Software

In one embodiment, the present disclosure provides a stand-alone health management software application including customizable dashboards for the management of a health condition, e.g., diabetes. Such a health management software application may be stored in and/or run from an analyte monitoring device, e.g., an analyte meter as described herein. Alternatively, the software application may be stored in and/or run from a processing device such as a smart phone device, PDA, server device, laptop or desktop computer.

The health management software can be configured such that an end user can create a new dashboard, e.g., using a "Create Dashboard Wizard" functionality which presents dashboard options to a user for selection, and/or modify an existing dashboard of the health management software. In one embodiment, the health management software is configured to allow an end user or health care provide to name or rename a dashboard so that it may be readily identifiable.

In another embodiment, the health management software is configured such that reports contained within a particular dashboard, e.g., a user configured dashboard, are dynamically refreshed in concert, as a result of a user changing the view on any individual report contained within the dashboard. For example, if the user changes a view period for a glucose modal day report included in a dashboard, the health management software can be configured such that each of one or more additional reports included in the dashboard are refreshed using the same time period as that selected for the glucose modal day report.

Reports within a dashboard can be refreshed with the same time period (exact time alignment) or each additional report may represent a previous or subsequent time period (sequential time alignment). Additional alignment relationships are also possible.

In another embodiment, the health management software is configured to allow a user to publish and/or distribute a dashboard to other users of the health management software and/or a health care provider, e.g., via an internet connection. Similarly, a health care provider could develop a dashboard and distribute the dashboard to one or more users (e.g., a primary care giver distributing a dashboard to his/her patients).

In one embodiment, the health management software is configured to automatically check for updates upon launch of the application. Alternatively, or in addition, such a check may be initiated by the user. Updates can include, e.g., new dashboards developed by the manufacturer of the health management software, its business partners, or a health care provider.

Meal Intake Reminder for Diabetes Management Meters and Application Software

In one embodiment, the present disclosure provides a diabetes management software application which includes a reminder algorithm for meal intake data entry.

In one such embodiment, the algorithm results in presentation to the user of a reminder to enter meal intake data on, e.g., an analyte meter, portable processing device (e.g., smart phone, iPhone®, laptop or PDA), and/or computer. Meal intake data can include, e.g., time of meal intake, meal composition, and meal-component quantification (e.g., carbohydrates in grams).

The algorithm may present the reminder based on one or more of (a) a "reminder profile" including frequency of data entry and meal content established by the user and/or by an HCP, (b) the number of data entries, and meal composition for each entry, that have already been entered within the day and within a time period, (c) a recommendation on the type of meal(s) to be consumed for the remainder of the day or time period.

In one embodiment, the reminder algorithm is configured to provide a reminder to the user based on an analysis of the history of meal-intake data entries made by the user and compared to a reminder profile configured by the user or HCP.

The algorithm may generate summary results from the data entries made by the user that indicate how many days have a full set of data, how many days have partial or incomplete data, and how many days have no data at all. In addition, the algorithm may generate data associated with meal composition for each day, and generate cumulative summaries for defined time intervals (e.g., each week in the current month).

The reminder profile may be configured by the user or by a qualified health care provider, such as a physician, clinical specialist or nurse.

In one embodiment, where the algorithm is configured to be run on an analyte meter, e.g., a glucose meter, the analyte meter may be configured with the reminder profile either (a) directly by the health care provider using the meter's user interface, (b) via a data management system that interfaces with the analyte meter, or (c) via another portable processing device.

The reminder algorithm may be configured to provide feedback to the user at any time regarding how many meal-intake entries have been made and how much of the schedule or reminder profile has been completed.

It should be noted that while the above reminder algorithm is discussed in the context of a meal-intake data entry reminder, additional algorithms and associated reminders may be configured for use with the analyte meters and/or health management systems described herein, e.g., analyte measurement reminders or other therapy reminders.

Recommendation for Analyte Monitor Type Based on Simulations

In some embodiments, the present disclosure provides methods for selecting for a user an analyte monitor and/or system among multiple analyte monitors and/or systems based on simulation data. CGM, GoD and SMBG analyte monitoring devices and/or systems are discussed previously herein and in the materials incorporated by reference herein. In one embodiment, the present disclosure provides a method for selecting a glucose monitoring device and/or system from among a CGM device and/or system, a GoD device and/or system and a SMBG device and/or system. The method includes running a simulation for each device and/or system, taking into account multiple meal and/or correction events that have been recorded for a particular user. The method utilizes glucose history, meal information and insulin delivery information in connection with these events as available for a particular device and/or system to calculate the optimal parameters specific to the user for the particular device and/or system.

For example, in one embodiment, a simulation for a SMBG device and/or system assumes that for each meal bolus event, the bolus is based on the meal information and the glucose level, but not on glucose trending information. In one embodiment, a simulation for a GoD device and/or system includes information similar to that for the SMBG device and/or system except that trending information is also taken into account for the bolus calculation. In one embodiment, a simulation for a CGM device and/or system assumes that whenever the glucose measurement exceeds a high or low threshold, that a correction bolus occurs based on glucose level and trending information. Alternatively, or in addition, the CGM simulation may take into account that a correction is triggered based on projected high or low thresholds. Metrics based on the simulation results may be used to provide an indication of acceptable glucose control. The method may be utilized by a health care professional in order to determine the appropriate device for a particular patient and/or user.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and aspects of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary aspects shown and described herein. Rather, the scope and spirit of present invention is embodied by the appended claims.

What is claimed is:

1. A method of determining the concentration of an analyte in a biological sample, comprising:
   inserting an analyte sensor in a sensor port of an analyte monitoring device, the sensor port comprising:
     a first set of contacts positioned along a top portion and a bottom portion of the sensor port for contacting a first analyte sensor having an opposing electrode contact configuration;
     a second set of contacts positioned on the top portion or the bottom portion of the sensor port for contacting a second analyte sensor having a co-planar electrode contact configuration;
     wherein the analyte monitoring device comprises a processor programmed to:
       receive a signal indicative of the concentration of the analyte from the first set of contacts, and
       receive a signal indicative of the concentration of the analyte from the second set of contacts; and
   depositing the biological sample on the analyte sensor;
   receiving, by the processor, the signal from either the first set of contacts or the second set of contacts; and
   determining the concentration of the analyte in the biological sample based on the signal.

2. The method of claim 1, wherein the first analyte sensor is a glucose sensor and the second analyte sensor is a ketone sensor.

3. The method of claim 1, wherein both the first and second analyte sensors are glucose sensors.

4. The method of claim 1, further comprising a communication unit.

5. The method of claim 4, wherein the communication unit is configured to provide two-way communication between the sensor port and a device and/or network external to the sensor port.

6. The method of claim 4, wherein the communication unit is configured to provide two-way communication between the sensor port and a network external to the sensor port.

7. The method of claim 6, wherein the network is a computer network.

8. The method of claim 4, wherein the communication unit is configured to provide wireless communication between the sensor port and an external device.

9. The method of claim 8, wherein the external device is a medication delivery device or an implanted or partially implanted analyte sensor.

10. The method of claim 8, wherein the external device is an insulin pump.

11. The method of claim 4, wherein the communication unit comprises a Universal Serial Bus (USB) connector.

12. The method of claim 4, wherein the communication unit is configured to provide wireless communication between the sensor port and an external device and/or network.

13. The method of claim 12, wherein the communication unit utilizes a wireless communication protocol selected from a radio frequency (RF) protocol and an infrared (IR) protocol.

14. The method of claim 12, wherein the communication unit is configured to provide wireless communication between the sensor port and an external device, the external device comprises a Radio-Frequency Identification (RFID) tag, and the communication unit utilizes an RF wireless communication protocol to communicate with the Radio-Frequency Identification (RFID) tag.

15. The method of claim 12, wherein the communication unit utilizes a wireless communication protocol selected from code division multiple access (CDMA) and Global System for Mobile communications (GSM).

16. The method of claim 1, wherein the sensor port is configured to receive analyte sensors having different widths.

17. The method of claim 16, wherein the sensor port comprises a side wall and a biasing mechanism configured to position the analyte sensors against the sidewall during insertion of the analyte sensors.

18. The method of claim 16, wherein the first analyte sensor has a width which is greater than that of the second analyte sensor.

19. The method of claim 16, wherein the first analyte sensor has a width which is less than that of the second analyte sensor.

20. The method of claim 1, wherein the sensor port comprises an analyte sensor ejector slidably engaged therewith.

21. The method of claim 1, wherein the sensor port comprises at least four sensor port contacts configured to contact the first analyte sensor upon insertion of the first analyte sensor into the sensor port, and at least three sensor port contacts configured to contact the second analyte sensor upon insertion of the second analyte sensor into the sensor port.

22. The method of claim 21, wherein the sensor port comprises at least seven different sensor port contacts.

23. The method of claim 22, wherein the sensor port comprises at least nine different sensor port contacts.

24. The method of claim 21, wherein one of the at least four sensor port contacts is attached to the top portion of the sensor port and three of the at least four sensor port contacts are attached to the bottom portion of the sensor port.

25. The method of claim 21, wherein the at least three sensor port contacts are attached to the top portion of the sensor port.

26. The method of claim 21, wherein the sensor port comprises a protective protrusion extending from the top portion of the sensor port into the interior of the sensor port.

* * * * *